(12) United States Patent
Chelak et al.

(10) Patent No.: US 7,651,512 B2
(45) Date of Patent: *Jan. 26, 2010

(54) LANCER

(75) Inventors: Todd M. Chelak, Waldwick, NJ (US);
Jonathan B. Gabel, Randolph, NJ (US);
Robert E. West, Basking Ridge, NJ
(US); William J. Allen, Stratford, CT
(US); Alan Bachman, Woodbridge, CT
(US); Scott W. Reed, Monroe, CT (US);
Ray Adams, Ansonia, CT (US)

(73) Assignee: Becton, Dickinson and Company,
Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/400,739

(22) Filed: Mar. 27, 2003

(65) Prior Publication Data
US 2003/0187470 A1   Oct. 2, 2003

Related U.S. Application Data

(63) Continuation of application No. 09/366,149, filed on Aug. 3, 1999, now Pat. No. 6,558,402.

(51) Int. Cl.
*A61B 17/14* (2006.01)
(52) U.S. Cl. ...................................... 606/181; 606/182
(58) Field of Classification Search ................. 606/181, 606/182, 183, 184, 185; 600/573, 583
See application file for complete search history.

(56) References Cited

U.S. PATENT DOCUMENTS

| RE32,922 | E | 5/1989 | Levin et al. |
|---|---|---|---|
| 4,976,724 | A | 12/1990 | Nieto et al. |
| 4,990,154 | A | 2/1991 | Brown et al. |
| 5,074,872 | A | 12/1991 | Brown et al. |
| 5,282,822 | A | 2/1994 | Macors et al. |
| 5,318,584 | A | 6/1994 | Lange et al. |
| 5,324,303 | A * | 6/1994 | Strong et al. ................. 606/181 |
| 5,350,392 | A | 9/1994 | Purcell et al. |
| 5,423,847 | A | 6/1995 | Strong et al. |
| 5,476,101 | A | 12/1995 | Schramm et al. |
| 5,554,166 | A | 9/1996 | Lange et al. |
| 5,569,286 | A | 10/1996 | Peckham et al. |
| 5,613,978 | A * | 3/1997 | Harding ...................... 606/181 |
| 5,730,753 | A | 3/1998 | Morita |
| 5,741,288 | A | 4/1998 | Rife |

(Continued)

FOREIGN PATENT DOCUMENTS

EP  0 137 975   10/1990

(Continued)

*Primary Examiner*—Darwin P Erezo
(74) *Attorney, Agent, or Firm*—Fitzpatrick, Cella, Harper & Scinto

(57) ABSTRACT

A lancer device that enables a user to draw blood from a patient and discard the used lancet without touching it. The device also has an adjustable tip for selecting the depth of stylet penetration into the patient and a triggering mechanism that utilizes a yoke latch and a leaf spring to discharge the lancet. The lancer also has a dampening feature to reduce vibrations when the lancet is moving.

7 Claims, 49 Drawing Sheets

U.S. PATENT DOCUMENTS

| | | |
|---|---|---|
| RE35,803 E | 5/1998 | Lange et al. |
| 5,873,887 A | 2/1999 | King et al. |
| 5,879,367 A | 3/1999 | Latterell et al. |
| 5,916,230 A * | 6/1999 | Brenneman et al. .......... 606/172 |
| 5,984,940 A * | 11/1999 | Davis et al. ................. 606/181 |
| 6,022,366 A * | 2/2000 | Schraga ...................... 606/181 |
| 6,045,567 A | 4/2000 | Taylor et al. |
| 6,210,420 B1 * | 4/2001 | Mauze et al. ................ 606/182 |
| 6,558,402 B1 * | 5/2003 | Chelak et al. ............... 606/182 |
| 6,811,557 B2 * | 11/2004 | Schraga ...................... 606/182 |

FOREIGN PATENT DOCUMENTS

| | | |
|---|---|---|
| EP | 0 885 590 | 12/1998 |
| EP | 0 904 731 | 3/1999 |

\* cited by examiner

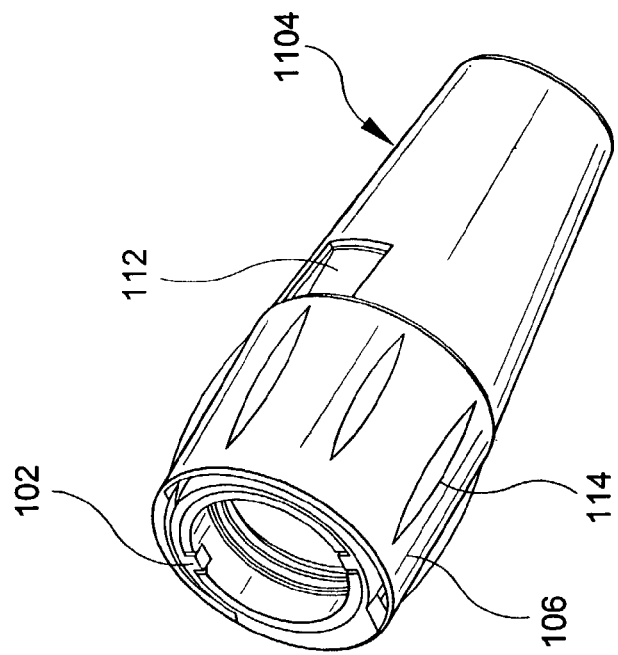
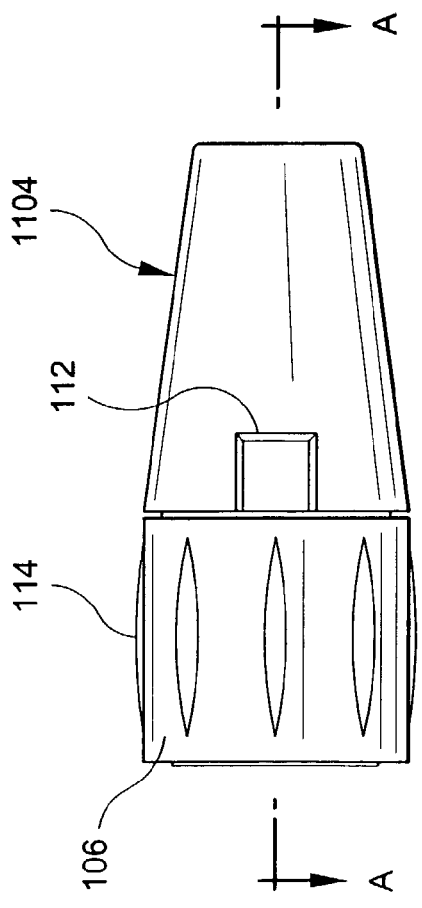
FIG. 4B
FIG. 4A

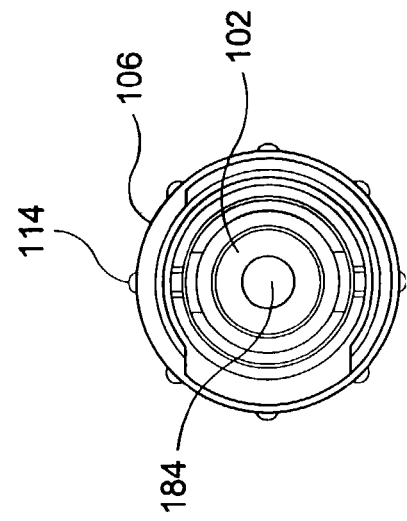
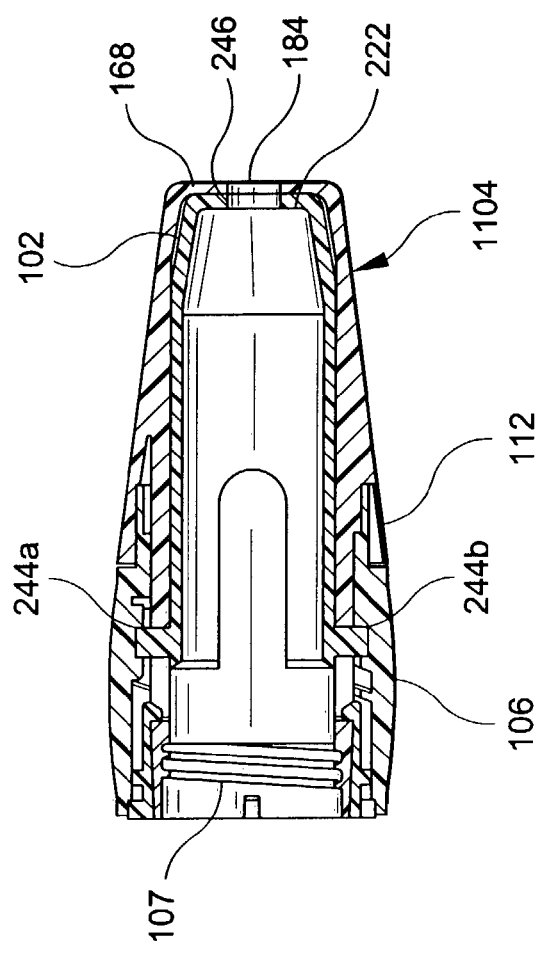
FIG. 4D
FIG. 4C

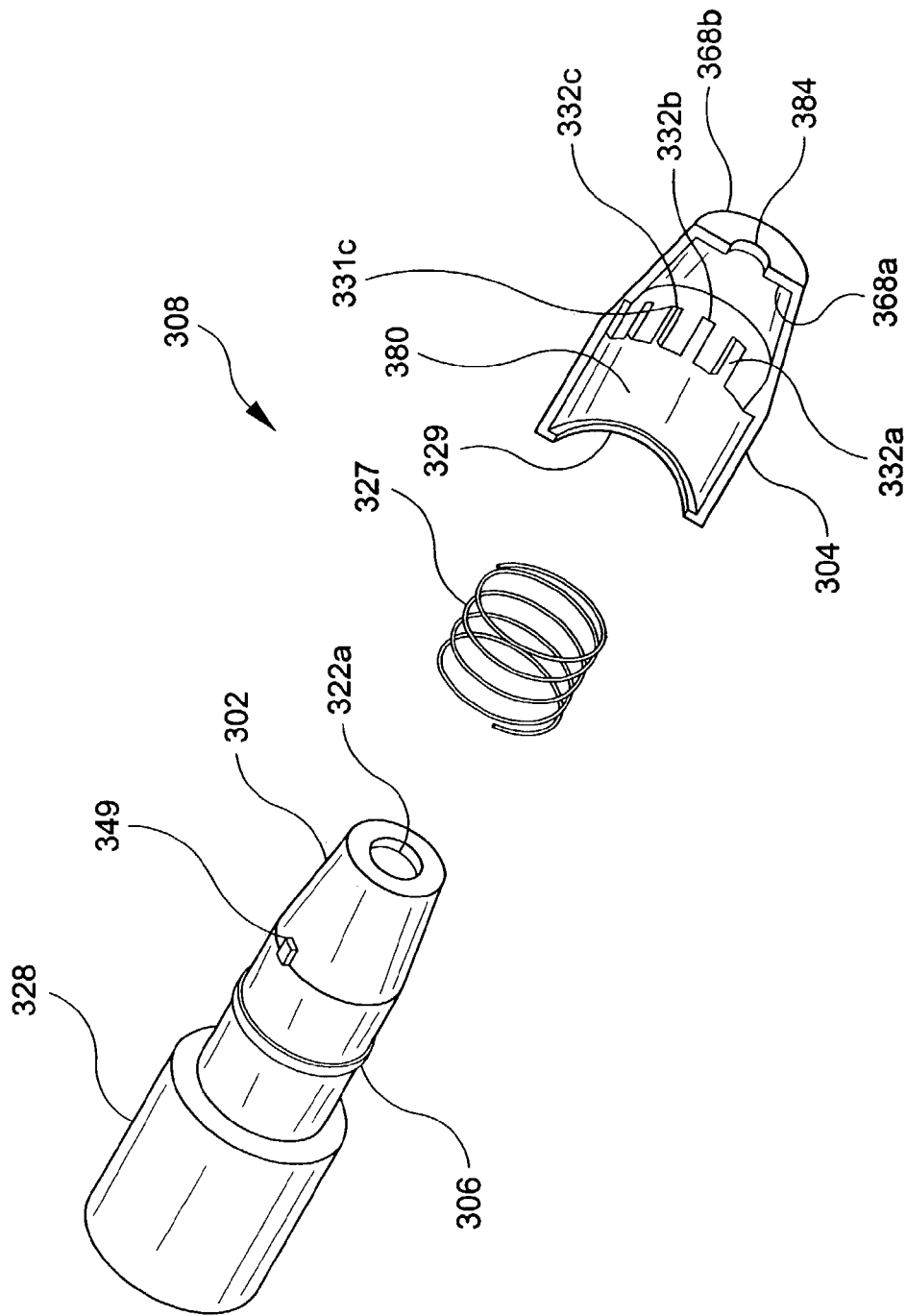

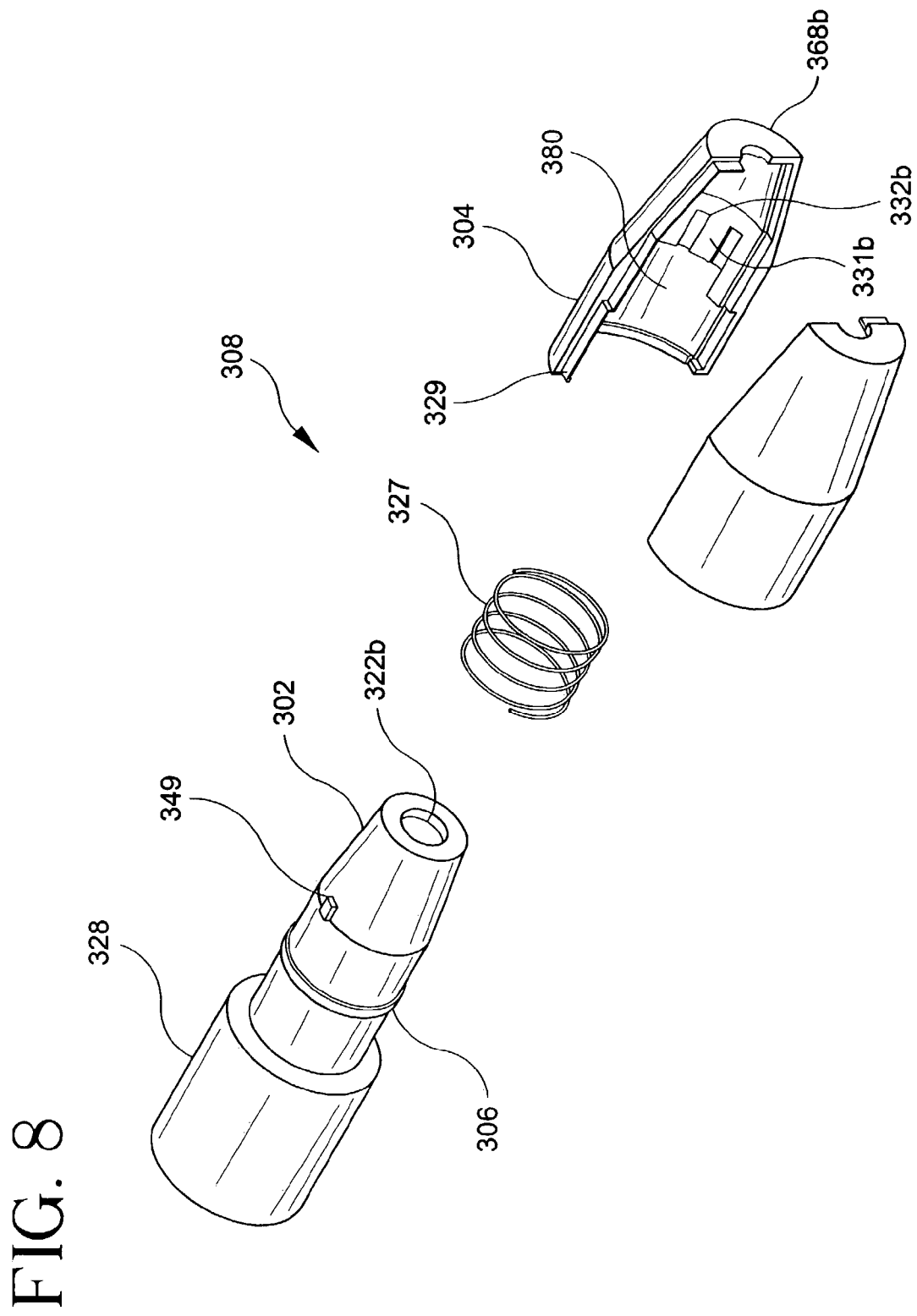

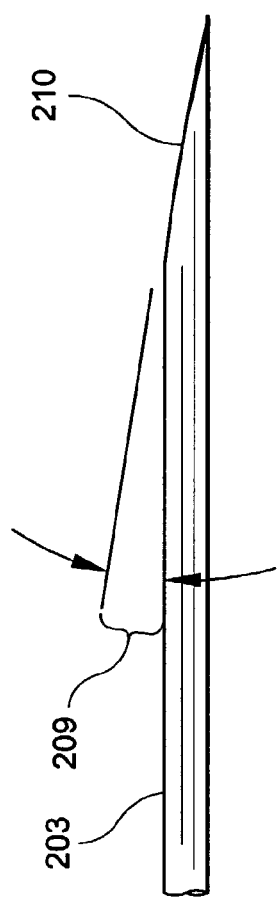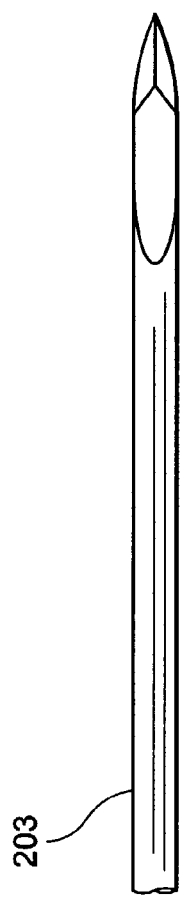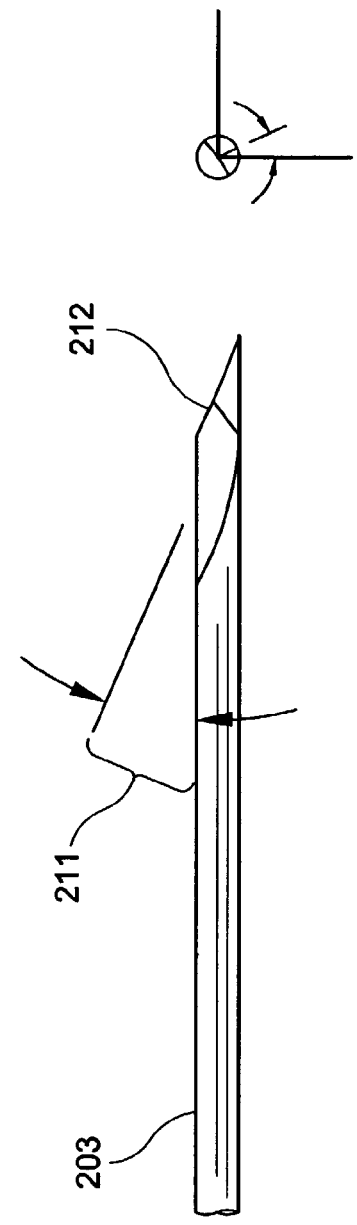
FIG. 35A
FIG. 35B
FIG. 35C

LANCER

This is a continuation of U.S. application Ser. No. 09/366,149, filed Aug. 3 1999, now U.S. Pat. No. 6,558,402.

BACKGROUND OF THE INVENTION

1. Field of the Invention

The present invention relates to a lancer for withdrawing a sample of blood from a patient via a lancet. More particularly, the invention is drawn to a lancer having a latch triggering mechanism for actuating the device. The lancer optionally has an adjustable tip for setting the depth of penetration of the lancet into the patient's skin by moving a lancet stop back and forth. The lancer may further include an ejection mechanism for automatically causing the release of the lancet from the lancer without the need to handle the lancet. Moreover, the lancer may include a dampening mechanism, such as a wisp, for reducing vibrations in the lancet, thus increasing patient comfort. The lancet may further include a centering mechanism to decrease undesired motions of the lancet perpendicular to the axial direction, when the lancet is fired.

2. Brief Description of the Art

Ballistic-type lancers are commonly used devices in the medical field for making a small puncture in a patient's skin to obtain a blood sample. One such lancer comprises a hollow lancer body and a lancet containing a sharpened needle, also known as a stylet. The lancet is mounted by the user onto a plunger within the lancer body. The plunger is capable of moving axially (back and forth) within the lancer body. The plunger is surrounded by a coil spring, which becomes compressed when the plunger is pulled back or "armed" by the user. The plunger is held in place by a trigger with the compressed spring exerting a force against the plunger. The lancer is now said to be in an armed state. The armed lancer is grasped by the user and its bottom is pressed against the patient's skin. When the plunger is released by the user by actuating the trigger, the spring decompresses, driving the plunger, and the attached lancet, toward the bottom of the lancer. As the propelled lancet hits a stop at the bottom of the lancer, its projecting stylet is pushed through a hole in the stop, which in turn swiftly pierces the patient's skin so that a drop of blood can be removed therefrom. That drop of blood may then be used for testing, such as blood glucose testing for diabetics. This lancer, however, does not completely meet the needs of patients and other users, such as medical personnel who employ the lancers to obtain samples from patients, for reasons described below.

To hold the plunger in the armed state, the conventional lancer, described above, uses a pawl-like trigger integrally attached to the bottom end of the plunger. When the plunger is cocked, the tip of the pawl-like trigger is received into an opening in the lancer body, thereby holding the spring-loaded plunger in place. A small button is positioned over the lancer body opening to allow the user to actuate the trigger, i.e., push the pawl tip out of the receiving hole and back into the lancer body. This pawl-like or detent-based trigger, however, can be actuated with relatively little force, which may result in an inadvertent firing of the lancet and the accidental piercing of the patient's or user's skin. Therefore, an improved triggering mechanism is desired that reduces the likelihood of accidental firing by actuating only when sufficient and intended pressure is applied thereto.

Also, because the pawl-like trigger is integral to the plunger, it places a bias force on the plunger. That bias force, however, is not in the same direction of the spring force on the plunger, and may adversely affect the operation of the plunger by causing it to deviate from its axial path of motion. This in turn can reduce patient comfort upon penetration of the stylet. Consequently, it is also desired that the improved triggering mechanism minimize introduction the of non-axial motion to the plunger so that it can have a more linear path of motion, thus increasing patient comfort.

The penetration depth of the stylet into the patient's skin is another important consideration in patient comfort, as well as being a major factor in determining the amount of blood that will be obtained from the patient (stylet gauge being the other major factor). Generally, as the stylet penetration depth increases, the amount of blood increases, as well as the patient discomfort. However, the required depth of penetration will differ from patient to patient, because skin thickness varies depending on the patient's age, gender, the extent to which it has been previously lanced, and other factors. If the penetration depth is set by the lancer design to be too shallow for the specific patient, the stylet may not adequately pierce the patient's skin, and repeated lancing attempts or smaller gauge (larger diameter) stylets may be required to extract the required amount of blood, which in turn wastes time and/or lancets, and in any event increases patient discomfort. On the other hand, if the lancer is designed to cause the stylet to penetrate too deeply for a specific patient, unnecessary discomfort will be incurred by that patient, as well as a longer recovery time.

A certain conventional lancer has been designed to have an adjustable stylet firing depth, wherein the distance that the plunger moves is precisely controlled to achieve the desired penetration depth of the stylet. However, to achieve this precise plunger control, complicated drive mechanisms involving many low tolerance and expensive components are required, as well as time-consuming and labor-intensive assembly.

Other conventional lancers allow for imprecise plunger movement, but instead accommodate cap (or tip) assemblies to permit the patient or other user to set for himself or herself a desired stylet penetration depth. The bottom of the cap assembly stops the movement of the lancet, and the stylet passes through a hole in the bottom of the cap to pierce the skin. For example, one type of lancer is designed to receive interchangeable caps. Each cap has, at its bottom, an annular stop portion, to stop the lancet. The lancet stop surrounds the hole that lets the stylet pass through. The bottom of the cap assemblies are each made to have a different thickness. Thicker bottoms provide a shallower stylet penetration depth, and thinner bottoms provide a deeper stylet penetration depth. The user selects the desired depth of penetration by placing one of the set of interchangeable caps onto the lancer. This adjustment technique, however, requires the manufacture, stocking and purchase of many various cap assemblies of differing thickness.

Another type of depth penetration adjusting assembly works by placing the lancet stop portion within the assembly itself. The bottom (distal) portion of the assembly has a hole that corresponds to the hole within the lancet stop, and the stylet passes through both the lancet and bottom holes. In this type of adjustable cap, the bottom of the cap is caused to move back and forth to provide respectively a smaller or larger space between the lancet stop and the bottom of the cap, which in turn respectively increases and decreases the stylet penetration depth.

One such depth penetration adjustment assembly includes three elements. The first is a cap element having its near end coupled to the lancer. At the distal end of the cap element is the lancet stop and an opening through which the stylet passes. The assembly secondly includes a cover element forming its bottom. The cover element also has an opening through which the stylet passes that corresponds to the opening in the cap element. The assembly has a third adjusting element disposed between, and engaging, the cap and cover elements. The adjusting element has a recessed portion on its outside to engage the cover element, which permits the adjusting element to rotate with the cover element when engaged. The adjusting element/cover element subassembly are engaged to the cap element via a threaded fitting, which allows the adjusting element/cover element subassembly to turn like a screw with respect to the cap element, which translates into axial movement of the bottom of the cover element with respect to the lancet stop of the cap element. This causes a variation of the stylet penetration depth. However, this device requires the manufacture and assembly of three discrete elements. Moreover, because the bottom cover element moves to achieve a variation in depth, the overall length of the lancer will vary depending on the adjustment setting, inhibiting easy storage and use of the lancer. Also, the depth setting can change since the tip may be rotated while being assembled on the device.

Another conventional depth penetration adjustable cap assembly also uses three elements: an inner sleeve having the lancet stop, an intermediate ring having a first helical incline camming surface, and an outer sleeve, having the bottom opening and a second helical incline camming surface. This assembly is likewise coupled to the lancer. The camming surfaces of the combined assembly capture a cam on the inner sleeve. When the outer sleeve is rotated, the cam forces the outer sleeve to move away from the lancer, thus increasing the distance between the lancet stop and the bottom of the outer sleeve, which in turn decreases the depth penetration. This assembly, however, suffers from the same problems as the previously described one.

Although all of the above-described adjustable depth penetration assemblies regulate the amount of skin penetration, and to a certain extent allow for easy adjustment, it is desired to have one that minimizes resetting errors when removing and replacing the cap.

In another aspect of conventional lancer operation, after the lancet has been used to draw blood from a patient it becomes contaminated with blood and, thus, poses a potential health hazard to anyone else who might be stuck by its stylet. Conventional lancers with ejection capabilities typically utilize a control member that is held by an operator. Unfortunately, if the operator removes a finger from the control member prior to complete separation, an accidental lancet ejection can result. In an attempt to prevent this, one conventional type of ejection mechanism utilizes a retention recess that retains the control member to permit ejection. This solution is less than optimal since there is still a possibility of accidental ejection. Other known ejection mechanisms tend to be cumbersome and require complicated manipulations, which are difficult for blind or disabled diabetics to accomplish, and increase the likelihood of accidental needle stick injury. In order to overcome the problems associated with the known lancet ejection mechanisms, it is desirable for the lancer to be capable of easily and automatically ejecting the contaminated lancet with the patient or other user using motions already known or familiar to the user.

In another aspect of conventional lancers, the spring-loaded plunger/lancet assembly may produce vibrations upon it being fired. In particular, the release of the compressed spring exerts a force on a plunger/lancet assembly to accelerate the same. The lancer's system dynamics, due primarily to the main spring that accelerates the plunger, are such that the plunger may vibrate in the axial direction after the lancet has rebounded from its stopping component. These vibrations may thus reduce the optimum propulsion of the lancet and reduce the comfort of the patient, because even small vibrations can be sensed by the patient upon lancing of the skin. It thus would be desirable to provide a lancer having a mechanism for dampening these vibrations and frictional dampening of axial movement, and thereby increase the comfort of the patient.

It would also be desirable to provide a lancer that has a mechanism to reduce radial movements of the plunger and thereby increase patient comfort by reducing radial forces introduced by the lancet stylet when it is penetrating the patient's tissue.

SUMMARY OF THE INVENTION

The present invention is drawn to an improved lancer having features that improve the safety of the device and increase the comfort of the patient. The lancer can include a triggering mechanism that will be actuated when a user deliberately applies the required force to fire the lancet. A swift release and retraction of the lancet provides improved operation of the lancer. The lancer also optionally has an adjustable tip portion that permits a user to select a desired depth of stylet penetration from a number of depth-penetration choices. This feature facilitates an adequate, reproducible lancing for the user or patient. The lancer may also optionally include an ejection mechanism that releases a used lancet without the user or patient touching the used lancet. The lancer optionally includes a vibration-reducing and dampening mechanism to increase patient comfort. These features provide an improvement over conventional lancer devices.

Accordingly, an embodiment is directed to an apparatus for propelling a lancet. This apparatus includes a body assembly that has a proximal portion, a distal portion, and an orifice disposed at the distal portion of the body. A guiding member is disposed in the body assembly and guides the lancet. A latch is disposed in the body assembly and engages the guiding member. The latch has at least one notch for engaging the guide member when the guide member is retracted. Upon actuation, the latch causes the guide member to disengage from the notch and propel the lancet toward the orifice at the distal portion of the body assembly.

The actuation is suitably facilitated by tangs moving past an inclined surface of the notch(es) of the latch.

Another embodiment is directed to an adjustment assembly, attachable to a lancer having an outer member and an inner member. The outer member has a distal portion, and a proximal portion, the distal portion having an exterior surface and an interior surface and an orifice from which a portion of the lancet emerges. The inner member has exterior and interior surfaces and is positioned relative to the outer member such that when the outer member is rotated, the inner member moves relative to the body assembly. This motion of the inner member is axially (forward and backward) and adjusts the distance between the inner member exterior surface and outer member interior surface.

Yet another embodiment is directed to an apparatus for propelling a lancet. This apparatus includes a body assembly, which has a proximal portion, a distal portion, and an orifice. A guide member is disposed in the body assembly, for guiding the lancet. An ejection mechanism is disposed in the body assembly, for preventing retraction of a lancet, when the guide member is rearwardly moved beyond a latching position, thereby detaching the lancet from the guide member following rearward positioning of the guide member. This rearward positioning of the guide member is facilitated by detachment of the nose portion.

Yet still another embodiment is directed to an apparatus for actuating a lancet. This apparatus includes means for guiding the lancet, disposed in the apparatus. It also includes means for actuating the guiding means, the actuating means having at least one notch. The actuating means engages the guiding means when the guiding means is retracted, and releases the guiding means from the actuating means when actuated.

Yet still another embodiment is directed to an apparatus for propelling a lancet. A body assembly has a proximal portion, a distal portion, and an orifice disposed at the distal portion. A guide member is disposed in the body section, for guiding the lancet. A latch, for actuating the guide member, is disposed in the body assembly. A means for dampening vibration is disposed on the guide member for reducing vibration of the guide member.

Yet still another embodiment of the instant invention is directed to a lancer having a yoke latch wherein actuation of the yoke latch causes it to move substantially perpendicular to the axis of the device.

Yet still another embodiment is directed to a method for ejecting a lancet, from a device having proximal and distal portions, and the device having a body assembly, a guide member and a cap portion, comprising the steps of:.
loading the lancet onto a guide member;
retracting the guide member proximally to a first position;
actuating the guide member to propel the lancet;
retracting the guide member proximally to a second position, the second position being beyond the first position in the proximal direction;
exerting a force, in the distal direction, on the lancet sufficient to detach the lancet from the guide member.

Additionally, a cap portion can be attached to the body assembly after the lancet is loaded and detached prior to retracting the guide member.

Yet still another embodiment is directed to a lancer device having a retention mechanism for preventing the device from inadvertently becoming armed when a user is attempting to load or unload a lancet. This device includes a guide member, disposed in a body assembly, for guiding the propelled lancet. A latch is disposed in the housing assembly and has at least one notch for engaging the guide member when the guide member is retracted. Actuation of the latch causes the guide member to disengage from the notch and propel the lancet toward the orifice at the distal portion of the body assembly. A retention mechanism, disposed in parallel with the longitudinal axis of the apparatus abuts a portion of the lancet and thereby prevents axial motion of the lancet. Thus, after firing, a portion of the latch prevents retraction of the guide member in the proximal direction.

Yet still another embodiment is directed to an apparatus for propelling a lancet. This apparatus has a body assembly, having a proximal portion, a distal portion, and an orifice disposed at the distal portion. A guide member is disposed in the body assembly, for guiding the propelled lancet. The apparatus also has means for reducing radial instability of the guide member while the guide member is propelling the lancet.

Yet still another embodiment is directed to a lancet having a base member and a stylet with an outer diameter of 31 gauge or smaller (i.e., higher gauge, such as 32, 33 etc.).

Yet still another embodiment is directed to an adjustment apparatus attachable to a lancer body assembly. This apparatus includes an outer member, having a distal surface, an orifice through the distal surface, and a plurality of slots disposed on an interior surface of the outer member, each slot having a distinct axial depth. An inner member has a distal surface, an orifice through the distal surface, and a protrusion, or a plurality of protrusions, extending from an exterior surface of the inner member. The protrusion(s) is insertable into one of the plurality of slots on the interior surface of the outer member so as to establish a distance between the distal surface of the inner member and the distal surface of the outer member. A biasing means is disposed around the inner member and is used to bias the outer member toward the inner member.

Yet still another embodiment is directed to an adjustment apparatus having an interior member with a plurality of slots, and an interior member with at least one protrusion, for insertion into a selected slot.

Yet still another embodiment is directed to an apparatus for propelling a lancet having a body assembly, with a proximal portion, a distal portion, and an orifice disposed at the distal portion. A guide member is disposed in the body assembly, for guiding the propelled lancet. A latch is disposed in the housing assembly, for engaging the guide member when the guide member is retracted and disengaging the guide member when a sufficient force is applied to the latch to cause the latch to deform. The force permits the guide member to pass through the latch.

BRIEF DESCRIPTION OF THE FIGURES

FIGS. 4A-4H show views of the first embodiment of the adjustment mechanism.
FIGS. 7 and 8 show an exploded and partial cut-away view of a third embodiment of the adjustment mechanism.

FIGS. 35A-35C and 36 show a perspective view of a stylet.

DETAILED DESCRIPTION OF THE PREFERRED EMBODIMENTS

Lancer devices are typically used to obtain a blood sample from a patient by piercing the skin so that a small amount of blood can be withdrawn. For example, ballistic-type lancer devices are typically designed to be used in conjunction with narrow gauge lancets to obtain a drop of capillary blood for use in a low-volume blood glucose monitor. One such glucose monitor requires approximately 2.5 micro-liters of capillary blood.

Figure 1:
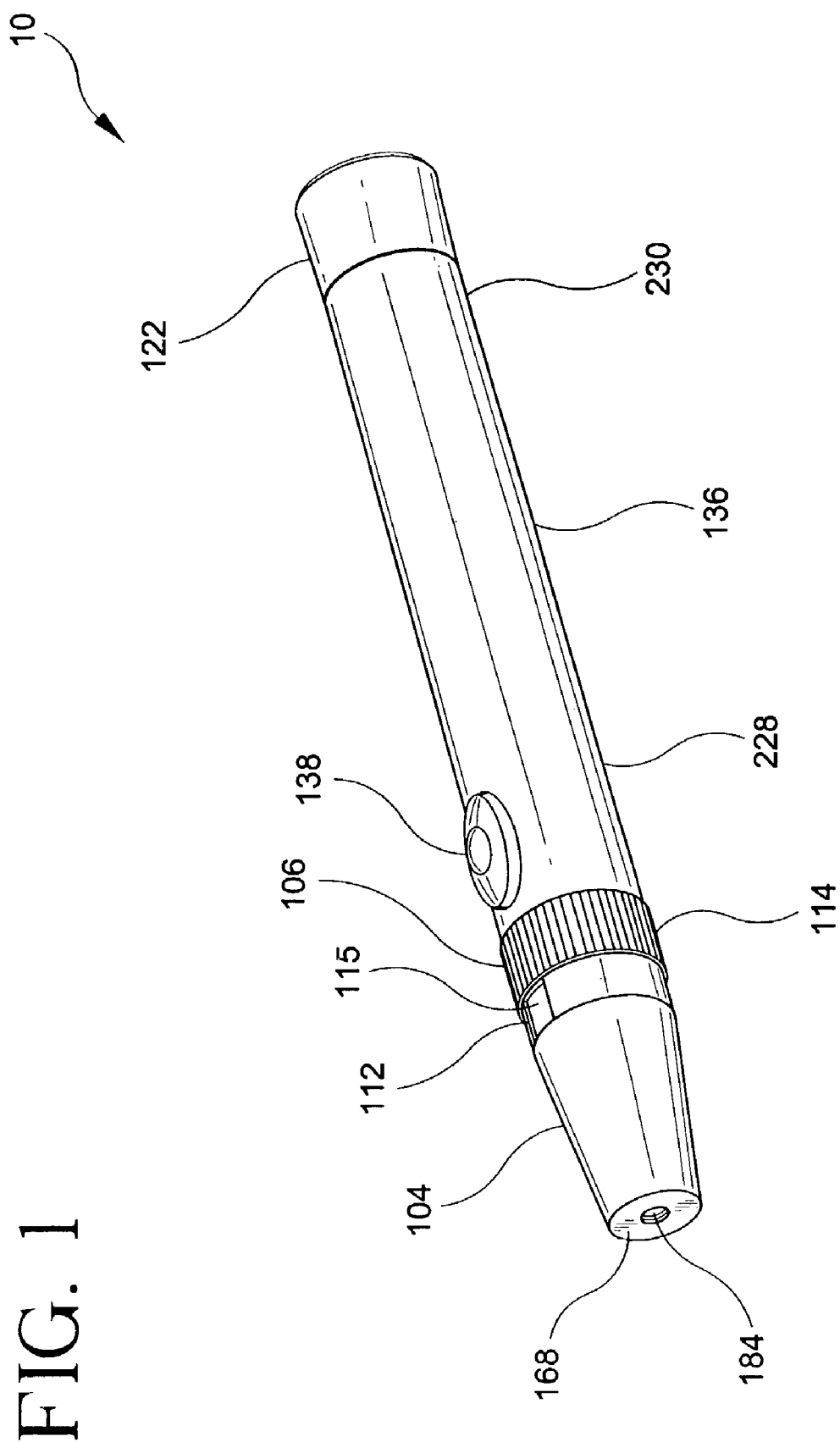
FIG. 1 shows a perspective view of a lancer device.

FIG. 1. shows a perspective view of the lancer device 10. The device 10 has a body assembly (also referred to as body section herein) 136 having distal portion 228 and proximal portion 230. Tip cap (also referred to as nose cap or nose portion) 104 is connected to body assembly 136 at distal portion 228. Nose portion 104 has a surface 168 at its distal end for pressing against a patient's flesh. Nose orifice 184 is formed in nose portion 104 for permitting the lancet stylet (not shown in FIG. 1) to emerge from the lancet device 10. Indication marks (not shown in FIG. 1) of the position of stylet stop (not shown in FIG. 1) are visible through nose portion notch or window 112. The notch 112 suitably has a translucent lens 115 covering the notch 112. The lens 115 magnifies the setting of the device, which is visible through notch 112. The setting is adjusted by the user and indication marks are marked on a portion of adjustment collar 106 so as to provide an indication to the user of the depth penetration of the stylet. Adjustment collar 106 is rotatable around nose portion 104 to set the desired depth of penetration. The user can change the setting by rotating the adjustment collar 106 to a desired setting. This is accomplished by grasping bumps or continuous knurl, shown as element 114, which are suitably raised grooves on the exterior surface of adjustment collar 106. Alternatively, element 114 could include Braille markings to facilitate a desired setting by seeing-impaired users.

Release member 138, which is suitably a button, is part of the triggering mechanism (complete triggering mechanism is not shown in FIG. 1) of lancet device 10. The triggering mechanism is designed so that a substantial portion of release member 138 extends above the outer surface of body assembly 136 when the release member 138 is not depressed. Knob cap 122, also referred to as end knob herein, is disposed at the proximal portion 230 of body assembly 136. The end knob 122 is used to arm the device 10.

Figure 2:
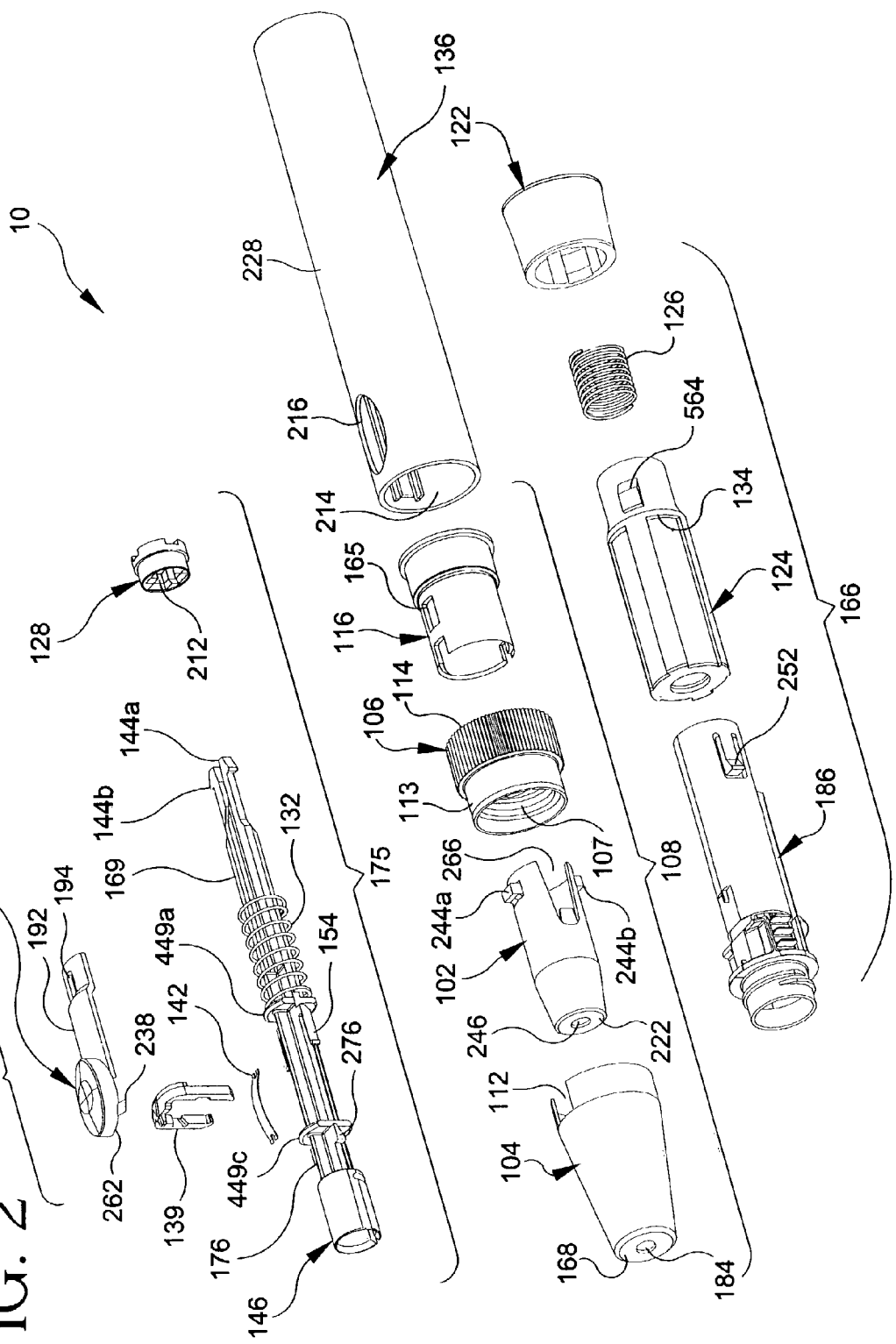
FIG. 2 shows an exploded view of component parts of the lancer device.

FIG. 2 shows an exploded view of the lancer device 10. Body assembly 136 is suitably a hollow, substantially cylindrical member with a body orifice 214 and button orifice 216 located at the distal end 228 of body assembly 136. Body orifice 214 provides a passageway for plunger 146 to push a lancet (not shown in FIG. 2) in the direction of nose portion 104. Body orifice 214 also provides a mounting location for tip thread end 116. Button orifice 216 provides a location to mount release member (also called a button herein) 138 to body assembly 136. Button 138 is used to actuate-triggering mechanism 172. The body assembly 136 houses various mechanisms of the lancer device 10. These mechanisms include: an adjustment mechanism 108, for selecting the depth of stylet penetration; an arming mechanism 166, for cocking or loading the lancer prior to firing; a trigger mechanism 172, for actuating the lancet; a support mechanism 175, for guiding the lancet so that a stylet (not shown in FIG. 2) emerges from the lancet device 10; and an ejection mechanism (not shown in FIG. 2), for ejecting a used lancet into an appropriate refuse container.

The components of each mechanism will now be described; however, the components of each mechanism are described as an exemplary embodiment and each mechanism does not necessarily require all of the components discussed in relation to that mechanism. Indeed, as will be apparent to one skilled in the art, the mechanisms are capable of operation with less than all of the components discussed, as well as with substitutions of the components.

The adjustment mechanism 108 enables a user to select a desired depth of stylet penetration into a patient's skin. When using lancer device 10, it is desirable to have a puncture depth sufficient to obtain the necessary blood sample. Typically the puncture depth in the patient should be in the range of approximately between 0.015 inch and 0.140 inch, and preferably between 0.024 inch and 0.105 inch. To accommodate different skin thicknesses and conditions the lancet device 10 has an adjustment mechanism 108. This adjustment mechanism 108 suitably includes a nose portion 104, a lancet stop 102, an adjustment collar 106 and a tip thread end 116.

The nose portion 104 is suitably ogival shaped with a diameter suitable to receive lancet stop 102, in a substantially mating relationship, in a cavity formed in the proximal end of the nose portion 104. The nose portion 104 has distal surface 168, for interfacing with the patient's skin, and nose orifice 184, which provides an opening for a stylet to emerge. Notch 112 is formed in nose portion 104 for revealing markings 113 on adjustment collar 106.

Lancet stop 102 is suitably an ogival shaped member with dimensions that permit insertion into nose portion 104. Lancet stop 102 has two U-shaped depressions or notches (only one notch 266 is shown in FIG. 2) and an orifice 246. Lancet stop 102 is disposed within nose portion 104 such that the lancet, upon actuation, will abut the lancet stop 102, thereby resulting in a predetermined extension of the stylet beyond distal surface e 168 of nose portion 104. Lancet stop 102 has one or more protrusions shown as 244(a) and 244(b) (although only two protrusions are shown, there could be more or less than two, and virtually any number that comports with the design would be acceptable) that extend radially outward and interact with surface 107, which is for example a camming surface or screw threads, in adjustment collar 106, and the protrusions 244(a) and 244(b) are constrained from radial rotation within aperture 165, which is also typically a slot, of tip thread member 116. (Although only a single aperture is shown, there could be any number that comports with the design of the device 10.) This moves the lancet stop 102 axially (i.e., back and forth) and thereby positions lancet stop 102 in nose portion 104.

The lancet stop 102 is used in conjunction with the nose tip 104 to adjust the penetration depth of a stylet. Lancet stop 102 has a distal surface 222. The position of this distal surface 222 in relation to the interior surface of nose portion 104 determines the distance a stylet emerges from nose orifice 184. Lancet stop 102 is moved via a radial rotation of adjustment collar 106 The lancet stop 102 suitably has six depth settings from which the user may choose, typically numbered "1" to "6" that correspond to a particular stylet penetration. (The number of depth settings is a design choice and is not critical to the understanding of the invention.) The further lancet distal surface 222 is from the nose orifice 184, the less a stylet will emerge from orifice 184, and the less penetration into the patient's skin.

Adjustment collar 106 has an inner threaded surface 107, such as screw threads or a camming surface, that permits rotation of the adjustment collar 106 about nose portion 104. The lancet stop 102 is moved via collar 106 since lancet stop protrusions 244(a) and 244(b) engage a portion of collar 106 within the confines of surface 107. The lancet stop 102 is prevented from rotating with the collar 106 due to the fixed relationship of protrusions 244(a) and 244(b) with aperture 165 of tip thread end member 116. Radial rotation of the collar 106 rotates threaded surface 107 and thereby cams a portion of the lancet stop 102. The lancet stop 102 is trapped from axial rotation due to protrusions 244(a) and 244(b) being movably interlocked or slidably engaged in a corresponding aperture 165 in tip thread member 116. Radially located detenting features (shown in FIG. 4C) between the nose portion 104, or the thread end member 116, and collar 106 keep the adjustment in discrete intervals.

Adjustment collar 106 has markings 113 on a distal portion indicating the position of lancer stop 102 within nose portion 104. Thus, the user or patient can set the adjustment mechanism to a particular penetration depth prior to each use, if they desire.

Adjustment collar 106 has grooves, bumps, or other markings 114 for facilitating a user or patient setting lancet stop 102 to a selected depth within nose portion 104. A continuous knurl surface suitably has markings within the knurl.

Tip thread member 116 provides a coupling between adjustment collar 106 and body assembly 136, via an optional sleeve member 186. The nose portion 104, having lancet stop 102 disposed therein, is attached to tip thread member 116, via optional sleeve 186, which is connected to body assembly 136. Typically, tip thread member 116 mounts in body orifice 214 or abuts it.

Alternatively, the tip thread member 116 could mount to sleeve 186, or collar 106 could mount to sleeve 186. Also, the tip thread member 116 could be fabricated to be an integral part of nose portion 104.

Alternatively, the tip thread member 116 could be integral with body assembly 136.

Various embodiments of the adjustment mechanism will be discussed in relation to FIGS. 3-14.

Figure 3A:
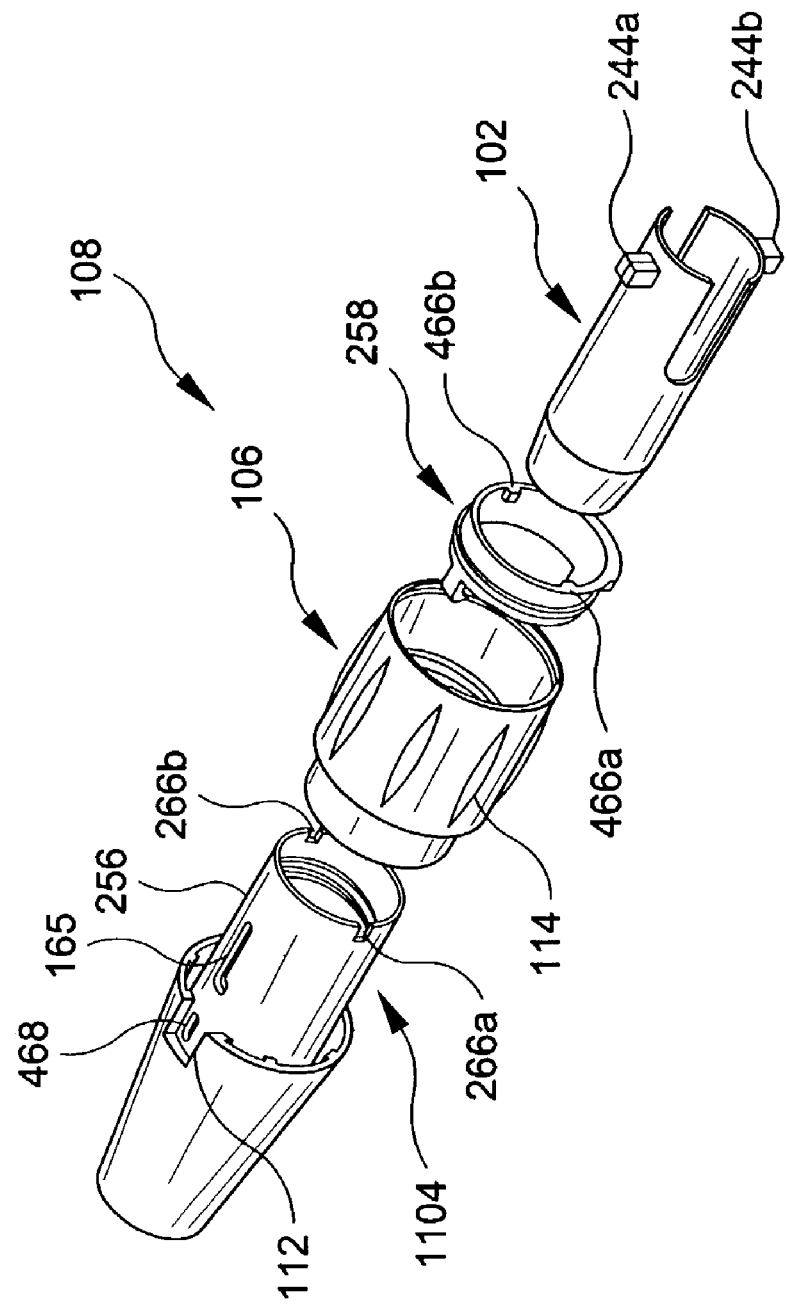
FIGS. 3A-3F show exploded views of a first embodiment of an adjustment mechanism.

Turning first to FIG. 3A, which shows an exploded perspective view of the adjustment mechanism 108, nose portion (shown in FIG. 2 as element 104) and tip thread member (shown in FIG. 2 as element 116) are a single nose piece shown as element 1104. Nose piece 1104 has notch 112, aperture 165, and an elongated portion 256. Notch 112 only exposes an indication of the current penetration depth. However, the other settings are obvious to a user because of the indicia, such as grooves, bumps or continuous knurl 114, which give the settings an intuitive feel. Elongated portion 256 has notches or grooves 266(a) and 266(b) for interfacing with protrusions 466(a) and 466(b) of coupling 258.

Slot, also called an aperture, 165 interfaces with protrusion 244(a) thereby preventing substantial radial motion of the protrusion 244(a). (There could be additional slots to interface with protrusion 244(b); but a single slot/protrusion interface will adequately control lancet stop 102.) This interface between slot 165 and protrusion 244(a) permits lancet stop 102 to move primarily only in an axial direction when collar 106 is rotated. The protrusion 244(a) interface with slot 165 prevent radial rotation of lancet stop 102. The protrusion 244(a) is positioned so that it can move axially within aperture 165, causing lancet stop 102 to move back and forth as collar 106 is rotated. Adjustment collar 106, with indicators 114, is mounted on the outside of elongated portion 256. Coupling 258 is used to retain adjustment collar 106 to single nose piece 1104. Camming surfaces on nose piece 1104 provide a connection mechanism to body assembly (not shown in FIG. 3A).

A pin protrusion 468 on nose piece 1104 interfaces with indentations, or camming surfaces, (shown as detenting element 470 in FIG. 3B) on the inner diameter of collar 106 to adjust the relationship between collar 106 and nose piece 1104 and prevent nose piece 1104 from axial motion, thus, collar 106 can only rotate relative to nose piece 1104. This prevents the overall length of the adjustment mechanism 108 from changing.

Figure 3B:
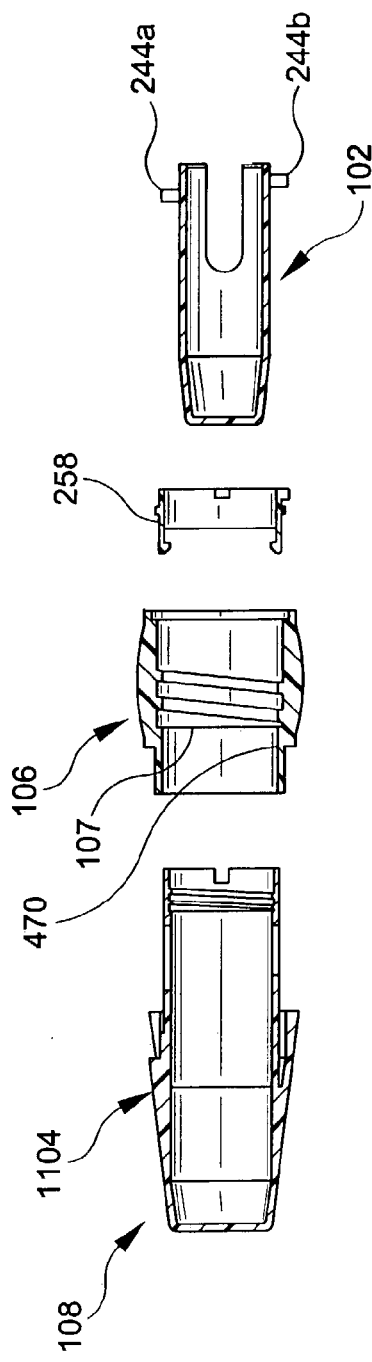
Figure 3C:
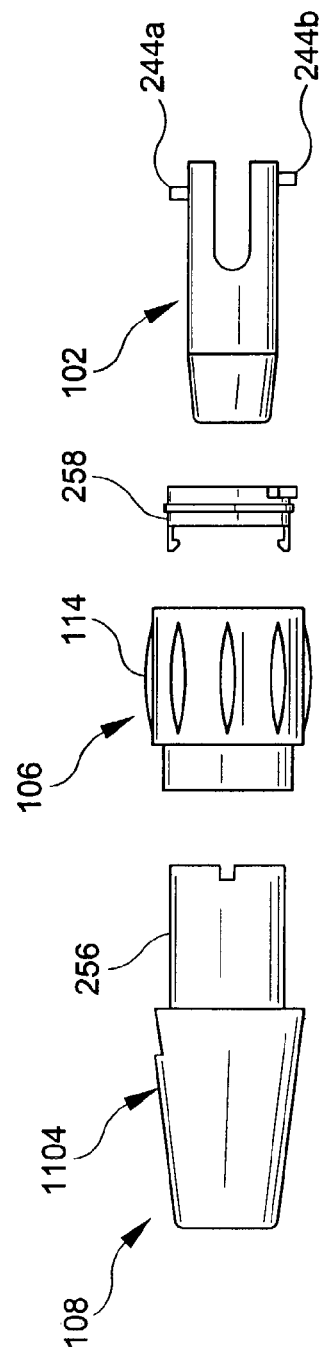

FIGS. 3B and 3C show cross-sectional and exploded views of adjustable tip mechanism 108. As seen in FIGS. 3B and 3C, the adjustment mechanism setting does not alter the overall length of the device since the lancet stop 102 is moved axially within nose piece 1104, using threads or camming surface 107. Thus, the nose piece 1104 does not extend or retract when the penetration depth is changed. Also, the depth of penetration does not inadvertently change when the lancer is in use or when the tip is detached and reattached. The collar 106, section 256, knurl 114, coupling 258 and protrusions 244(a) and 244(b) have been discussed in relation to FIG. 3A.

Figure 3D:
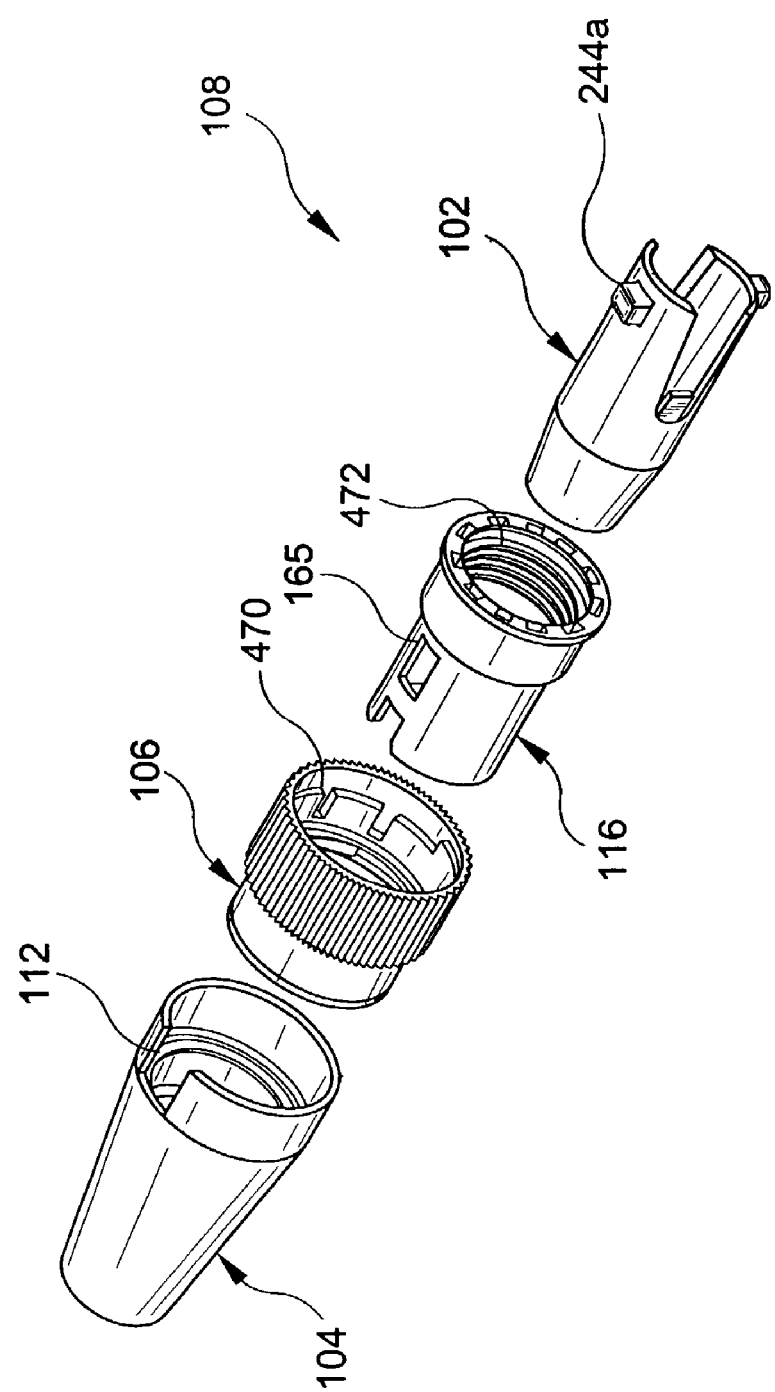
Figure 3E:
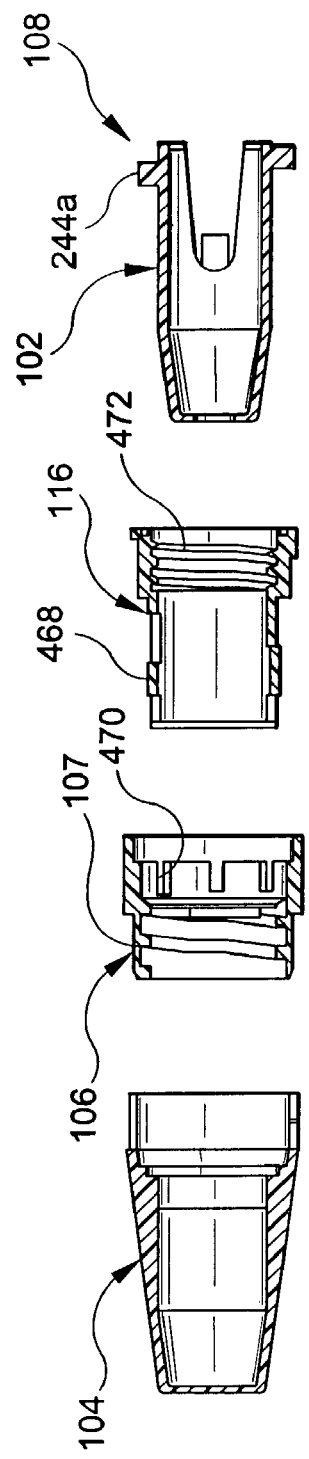
Figure 3F:
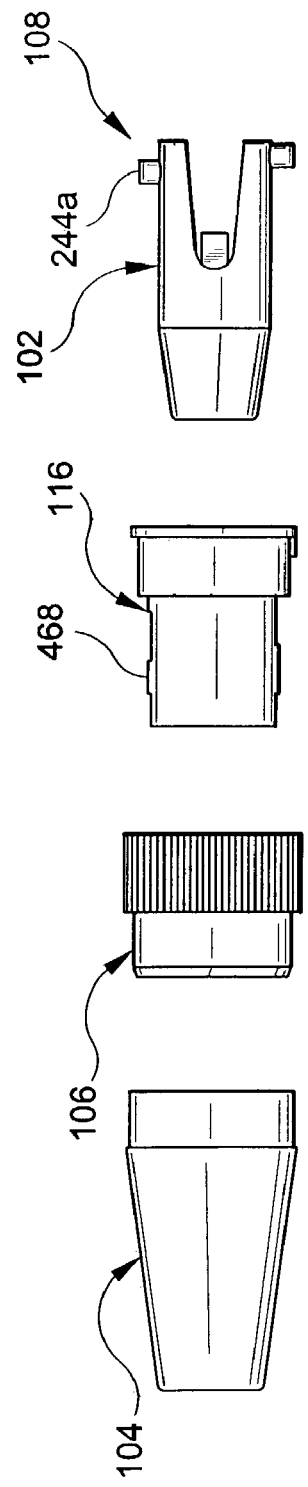

FIGS. 3D-3F show an embodiment of adjustment mechanism 108 in which the nose portion 104 with notch 112 interfaces with collar 106, tip thread member 116 and lancet stop 102. The collar 106 has detenting surfaces 470 to interact with a pin protrusion 468. (There are typically any suitable number of detenting slots; but they are collectively shown as element 470.) Protrusion 244(a) is positioned in slot 165, which permits substantially only axial motion and prevents virtually all rotation of lancet stop 102. Tip thread member 116 has camming surfaces 472 for interfacing with either the body assembly or sleeve. (Neither the body assembly or sleeve is shown in FIGS. 3D-3F.) FIGS. 3D-3F are similar to the embodiment shown in FIGS. 3A-3D except that the nose portion 104 is a distinct element from tip thread member 116. Both embodiments enable axial (back and forth) motion of lancet stop 102, while preventing radial movement of lancet stop 102.

FIGS. 4A and 4B show perspective views of single nose piece 1104 and adjustment collar 106. (FIGS. 4A-4D are directed to a single nose piece embodiment similar to the embodiment described in FIGS. 3A-3C above.) As shown in FIG. 4A nose piece 1104 interfaces with adjustment collar 106 such that notch 112 exposes a portion of collar 106. This portion can be modified by rotating collar 106 using grooves 114.

FIG. 4B shows a perspective view of the adjustment assembly 108. The relationship between nose piece 1104, lancet stop 102 and collar 106 is illustrated.

FIG. 4C shows a cross-sectional view along the longitudinal axis. As shown in FIG. 4C, lancet stop protrusions 244(*a*) and 244(*b*) interface with adjustable collar 106. Thread or cam surface 107 enables axial movement of the lancet stop 102 within nose piece 1104. Lancet stop distal surface 222 is spaced from nose piece distal surface 168 such that lancet stop orifice 246 is aligned with nose orifice 184. This permits a portion of a stylet to emerge a predetermined distance from nose piece 1104, based on the setting of lancet stop 102. Notch 112 permits a user or patient to view the setting on collar 106.

FIG. 4D shows a cross-sectional view along the radial axis. The relationship of the nose orifice 184, lancet stop 102, collar 106 and grooves 114 is illustrated.

FIGS. 4E-4H show an embodiment in which the nose portion 104 and tip thread member 116 are distinct elements. (This is similar to the embodiment discussed in relation to FIGS. 3D-3F discussed above.)

Figure 4E:
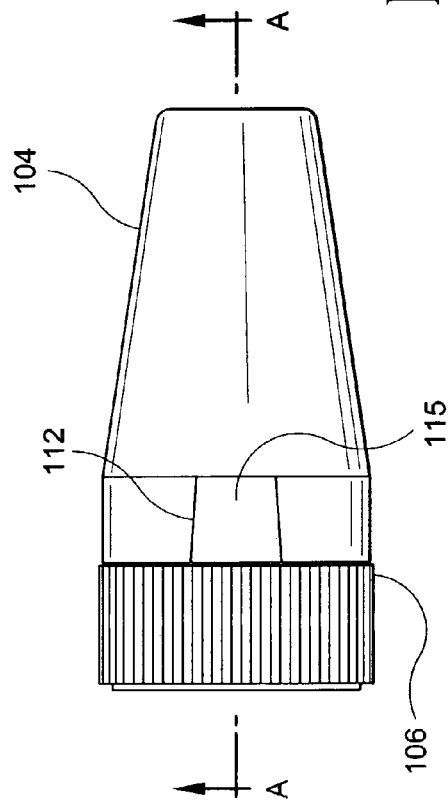
Figure 4F:
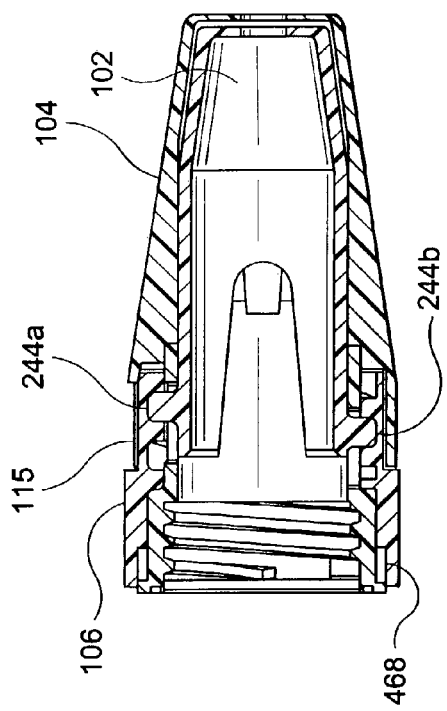
Figure 4H:
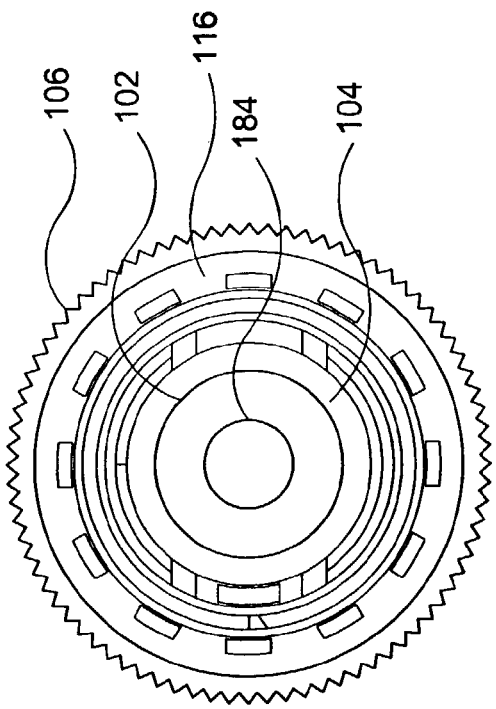
Figure 4G:
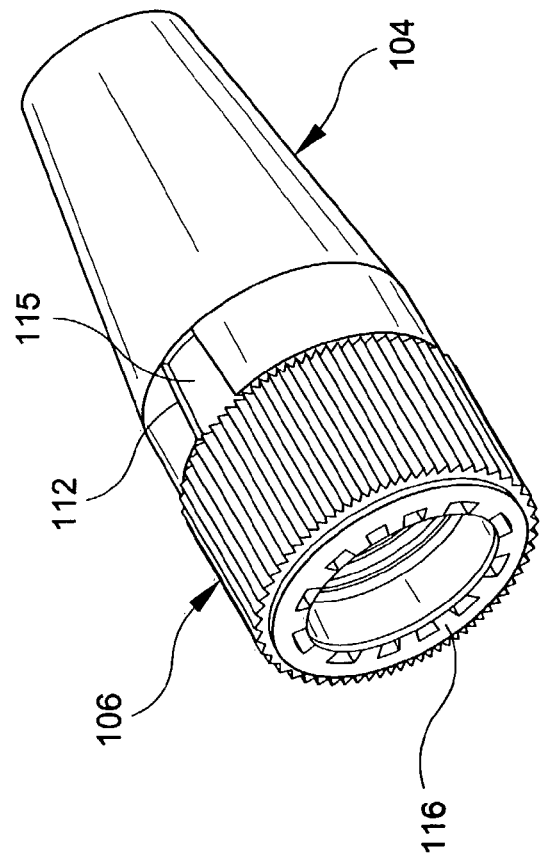

FIGS. 4E and 4G show perspective views of nose portion 104, with notch 112 and collar 106. FIGS. 4E and 4G also show a covering 115, which is typically a lens for magnifying the setting.

FIGS. 4F and 4H are similar to FIGS. 4C and 4D, respectively, except that the nose piece shown as 1104 in FIGS. 4C and 4D is two pieces; specifically 104 and 116 in FIGS. 4F and 4H. FIG. 4F shows lancet stop 102 inserted in nose portion 104 and protrusions 244(*a*) and 244(*b*) interfacing with collar 106. Pin protrusion 468 and covering 155 are also shown.

FIG. 4H shows the relationship between nose orifice 184, lancet stop 102, nose portion 104, tip thread member 116 and collar 106.

Figure 5A:
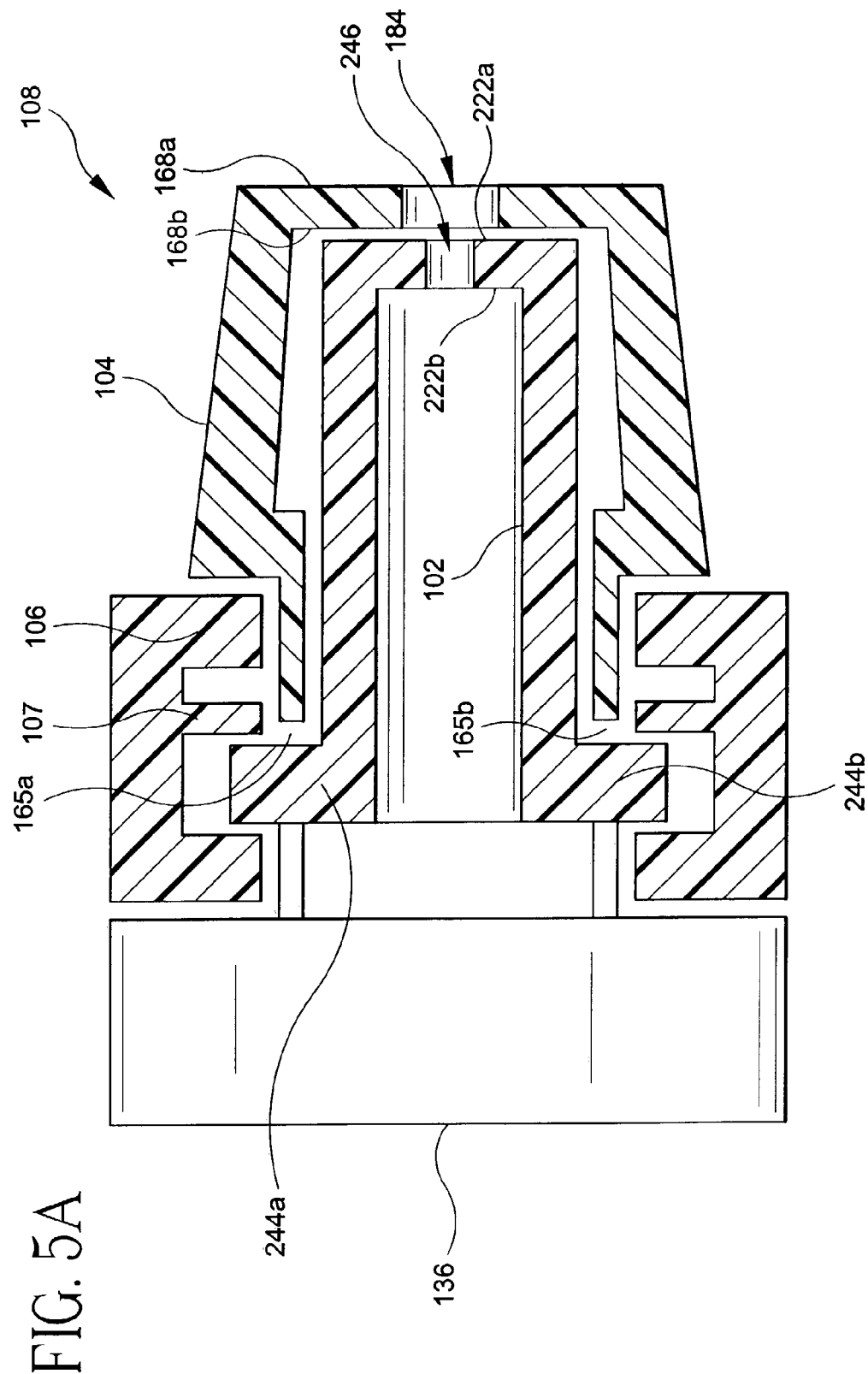
FIGS. 5A and 5B show a cross-sectional view of the first embodiment of the adjustment mechanism.
Figure 5B:
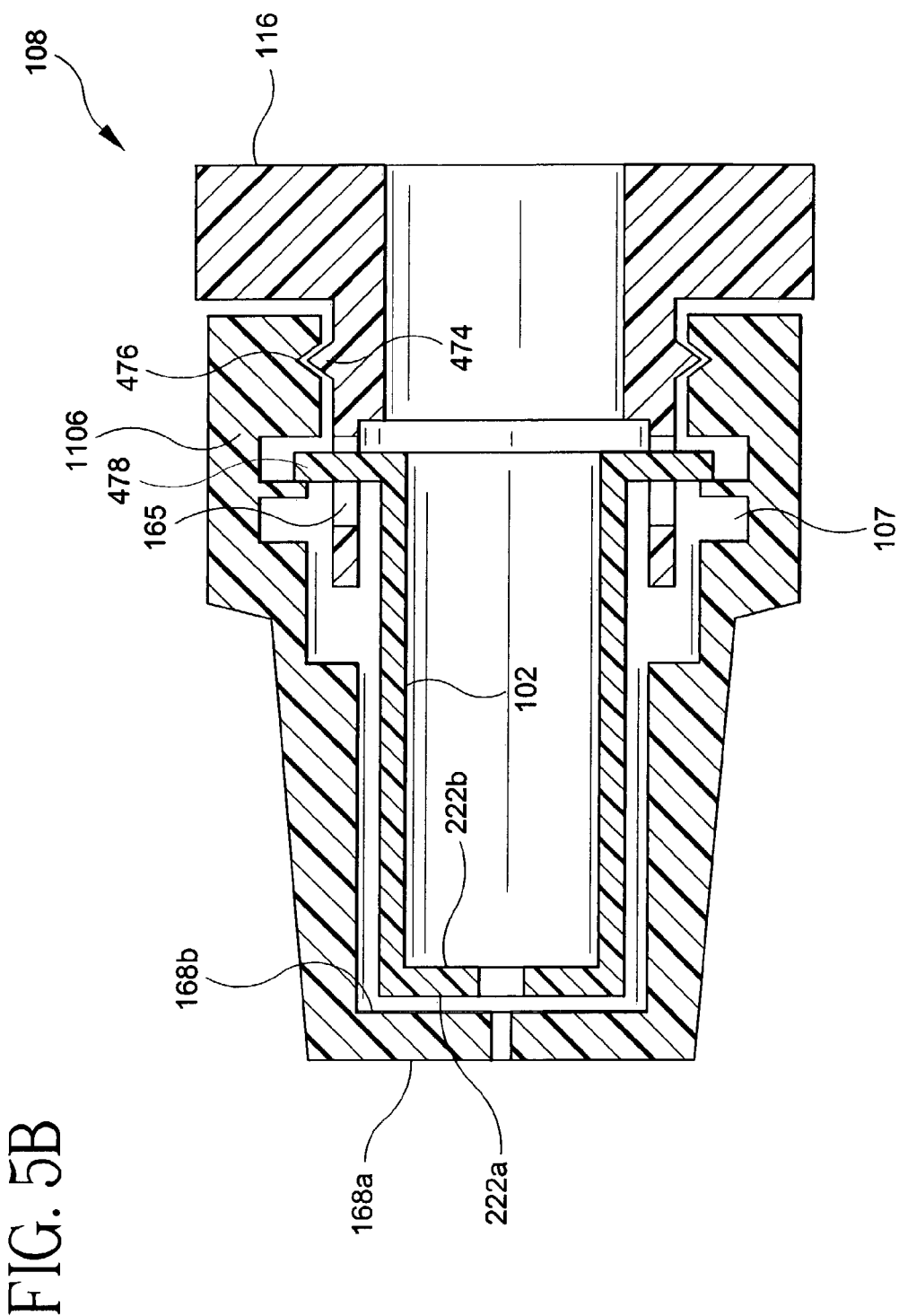

FIGS. 5A and 5B show a first embodiment of the adjustment assembly 108. FIG. 5A shows the adjustment assembly 108 suitably attaches to the body assembly 136 of a lancer device. The adjustment assembly 108 has two portions. These are an outer member and an inner member. The outer member is shown as nose portion 104 and adjustment member 106. FIG. 5B shows outer member as element 1106, which is suitably prevented from translation with respect to tip thread member 116.

As shown in FIG. 5A, the outer member 104, 106 has a distal portion toward orifice 184 and a proximal portion toward body assembly 136. Surface 168(*a*) is an exterior surface and surface 168(*b*) is an interior surface of outer member 104, 106.

Inner member, also referred to as lancet stop herein, 102 has exterior distal surface 222(*a*) and interior distal surface 222(*b*). Inner member 102 also has orifice 246 and protrusions, or posts, 244(*a*) and (*b*). These protrusions 244(*a*) and 244(*b*) interact with slots 165(*a*) and 165(*b*), respectively, to prevent inner member 102 from rotating relative to nose portion 104 when the inner member 102 is being translated by camming action of adjustment member 106. This translation is back and forth motion, with virtually no rotation of inner member 102. Thus, rotation of adjustment member 106 will cause surface 107 to axially move inner member 102 and determine the distance between inner member distal exterior surface 222(*a*) and outer member 104 interior surface 168(*b*). The outer member 104 does not move axially. A propelled lancet will encounter inner member distal interior surface 222(*b*). The larger the gap between distal portions of the inner member 102 and the outer member 104; the less the penetration depth. Similarly, the closer inner member 102 distal exterior surface 222(*a*) is to outer member 104 interior surface 168(*b*); the greater the penetration depth.

FIG. 5B shows the adjustment mechanism 108 in which the outer member is a single member 1106. Member 474, which is attached to tip thread end 116, interfaces with slot 476 of nose member 1106 to prevent translation of the nose member 1106 relative to body assembly (not shown) or tip thread member 116, which is suitably attached to the body assembly, by interacting with slot 165 when nose piece 1106 is rotated. Nose piece 1106 rotational motion causes inner member 102 to move axially by camming action of surface 107 on protrusion 478. Protrusion 478 of inner member 102 prevents substantial rotation of inner member 102. The protrusion 478 "rides" within slot 165, which allows for axial (back and forth) motion while trapping lancet stop 102 from rotational motion. The surfaces 168(*a*), 168(*b*), 222(*a*) and 222(*b*) are also shown.

Figure 6:
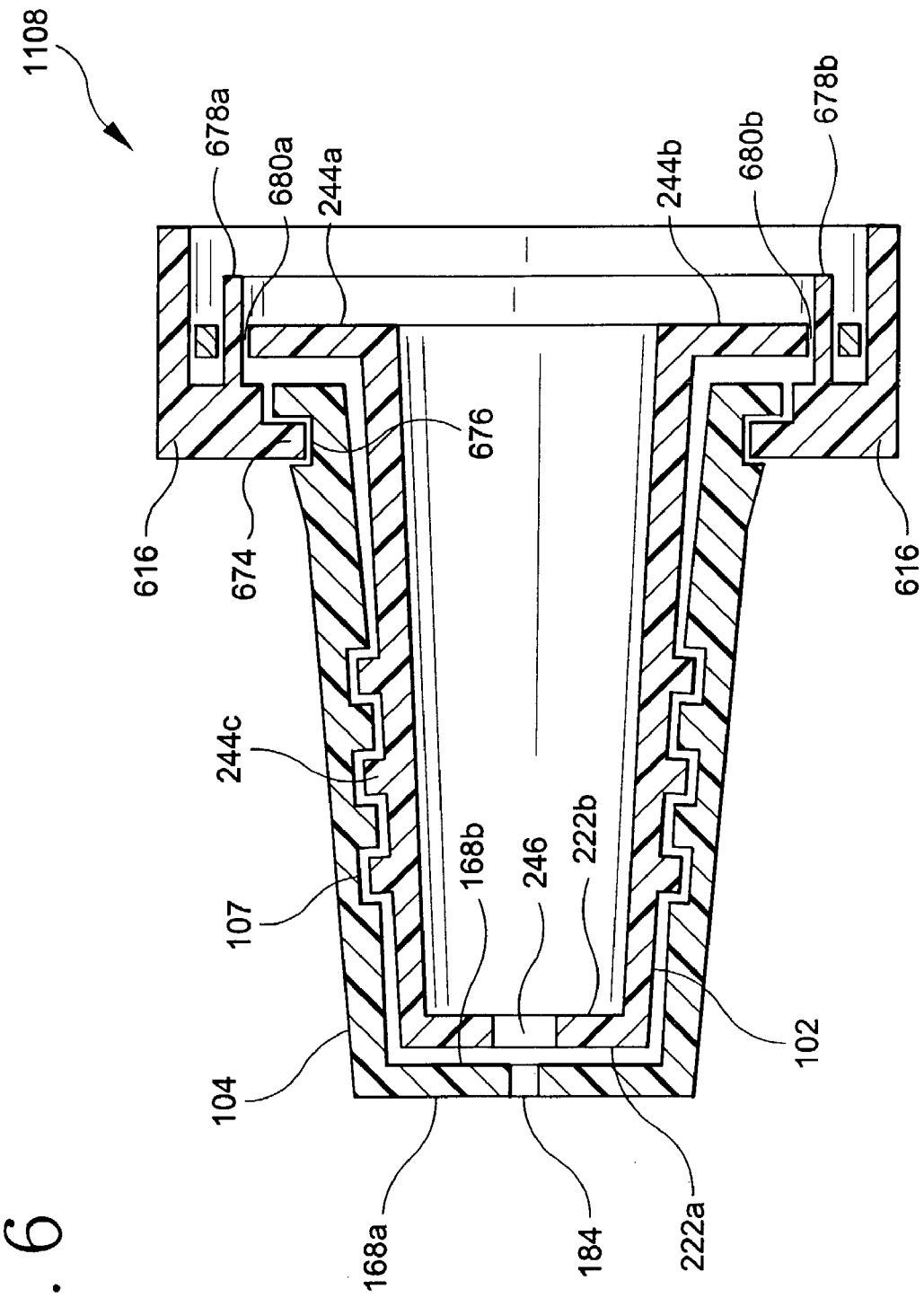
FIG. 6 shows a cross-sectional view of a second embodiment of the adjustment mechanism.

FIG. 6 shows a second embodiment 1108 of the adjustment mechanism. This embodiment also suitably attaches to a lancer device. The inner member 102 has protrusions 244(*a*) and 244(*b*). Slots 680(*a*) and 680(*b*) engage posts 678(*a*) and 678(*b*), respectively, on body attachment member 616. Rotation of outer member 104 translates inner member 102 relative to body attachment member 616 and rotates outer part 104 due to interlocking of outer member 104 and body attachment member 616 via member 674 and member 676. These members 674, 676 axially constrain outer member 104 and body attachment member 616; but permit relative rotation between outer member 104 and body attachment member 616. The outer member 104 does not move axially away from the body assembly (not shown). Protrusions 244(*c*) interact with surface 107 to move inter member 102 axially (back and forth) and thereby determine the distance between inner member 102 distal exterior surface 222(*a*) and outer member 104 interior surface 168(*b*). This distance, as stated above, determines the amount of a stylet that emerges from orifice 246 and orifice 184.

FIGS. 7 and 8 show a third embodiment of the adjustment mechanism. Adjustment mechanism 308 is suitably attached to a lancer device. Member 328 is suitably a part of the adjustment mechanism or, alternatively, the distal portion of the body assembly to which the adjustment mechanism is affixed. In this embodiment, the user pulls the outer member 304 distally and rotates it, moving the outer member 304 from the stopping face 332. (A plurality of stopping faces are designated generally by numeral 332.) Operation of this embodiment involves a user pulling nose 304 to release protrusion 349 from slot one of the slots, shown generally as numeral 331, therefore, allowing relative rotation of 304 and 328. While the relative rotation is occurring, no translation between surface 322 and surface 368 occurs. While the outer member 304 is pulled away from the body assembly 328, the stopping face 332 is moved distally so that the protrusion 349 is removed from the associated slot 331 and is able to float above the slots 331 in the adjustment area 380. Distally pulling nose portion 304 disengages protrusion 349 from the slot 331, permitting rotation. While rotation is occurring, virtually no translation is occurring. Each slot 331 has unique distance away from surface 368 to determine the distance a stylet will emerge.

The user can select a slot by rotating the outer member 304 so that a new slot of the plurality of slots, shown generally as element 331, is aligned with the protrusion 349 and a new stopping surface 332(*b*) is engaged as the spring 327 biases the outer member 304 toward the body assembly 328.

When the protrusion 349 is engaged to a particular slot 331, the outer member 304 cannot rotate relative to the body assembly 328. Thus, the motion of the user is a pull, rotate, and return to set the adjustment assembly 308.

Outer member 304 has interior distal surface 368(a), exterior distal surface 368(b), and orifice 384. A plurality of slots (shown collectively as element 331, and specifically as 331(b) and (c)) are disposed on the interior of member 304. Each slot 331 has a distinct axial depth and interfaces with pin, also referred to as protrusion, 349 to establish a relationship between inner member 302 and outer member 304; and more particularly, a relationship between inner member distal exterior surface 322(b) and outer member interior surface 368(a). Element 329 provides a surface for biasing spring 327 to act against. Spring 327 can bias outer member 304 to body assembly 328 near the proximal portion of outer member 304. This provides attachment of outer member 304 to the body assembly 328.

Spring member 327 is used to bias the outer member 304 relative to the inner member 302 and enables the adjustment assembly 308 to lock into position by biasing pin 349 into a selected slot 331. Element 306 is a raised ridge on inner member 302 which anchors biasing spring 327.

Figure 9B:
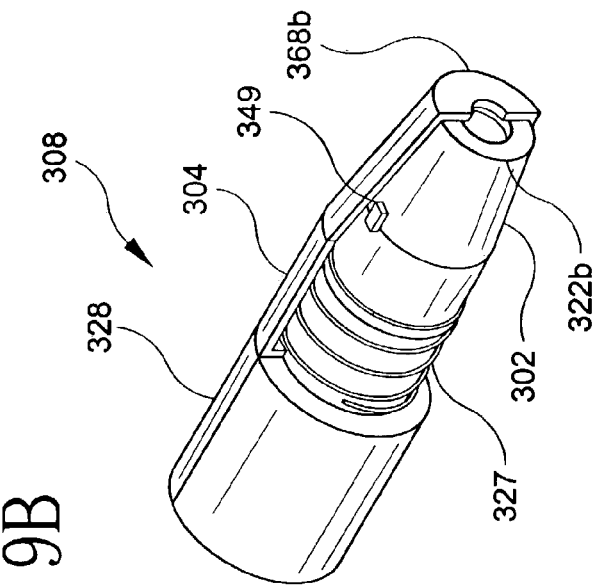
FIG. 9B shows a cut-away view of the third embodiment of the adjustment mechanism.
Figure 9A:
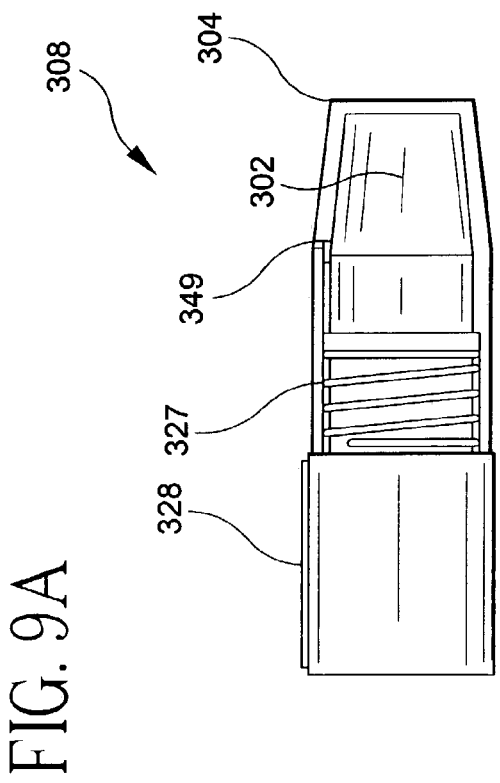
FIG. 9A shows a cross-sectional view of the third embodiment of the adjustment mechanism.

FIGS. 9A and 9B show cross-sectional and cut-away views, respectively, of the third embodiment of the adjustment assembly 308. FIGS. 9A and 9B show the relationship of body assembly 328, spring 327, outer member 304, inner member 302, protrusion 349, and surfaces 322(b) and 368(b).

Figure 10A:
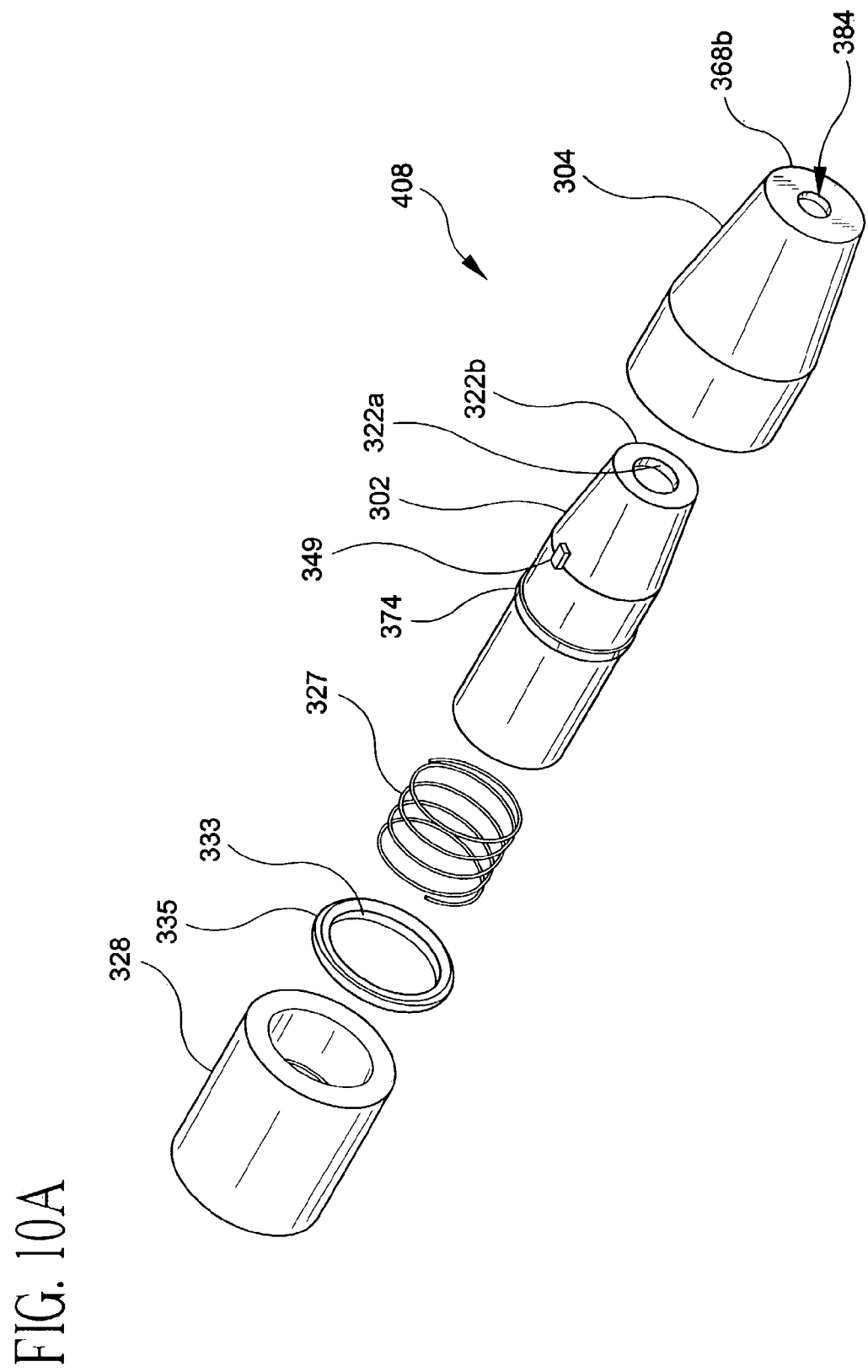
FIGS. 10A and 10B show a fourth embodiment of the adjustment mechanism.
Figure 10B:
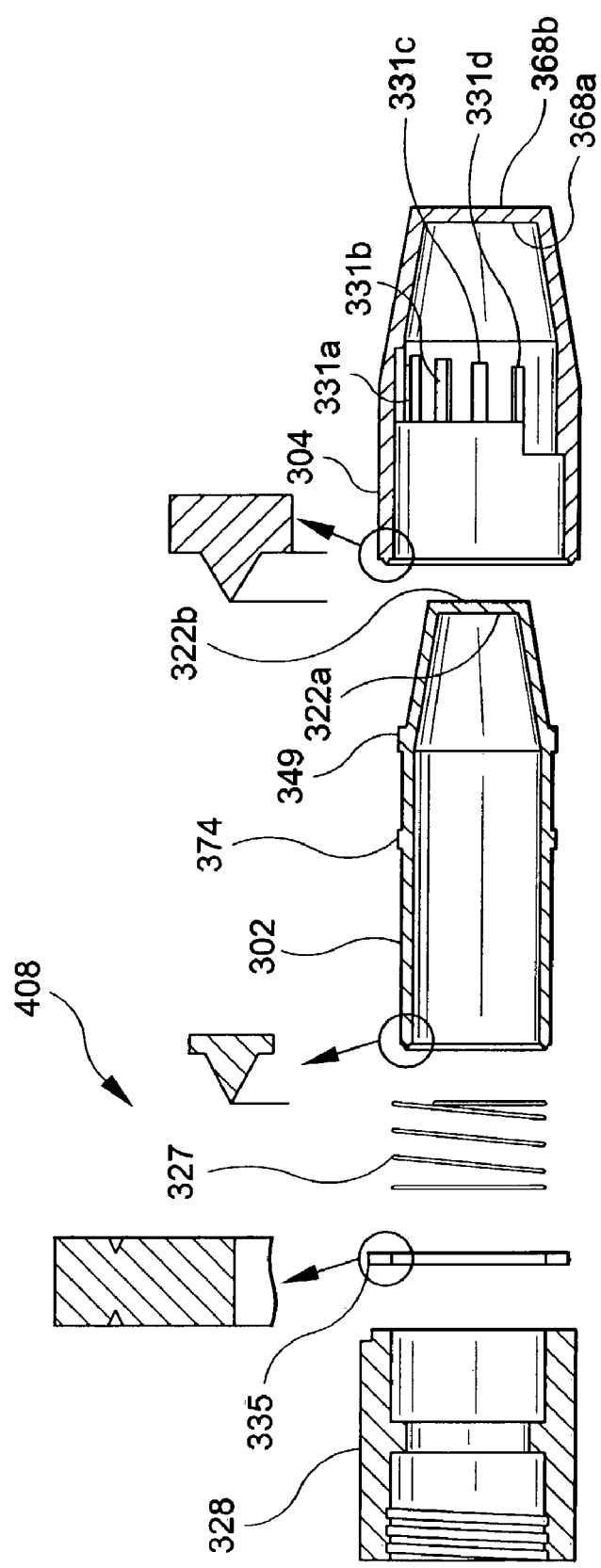

FIGS. 10A and 10B show perspective and cross-sectional exploded views, respectively, of the fourth embodiment of the adjustment assembly 408. This embodiment utilizes a collar member 335 having interior camming surface 333 to attach inner member 302 and outer member 304 to body assembly 328.

As shown in FIGS. 10A and 10B, the interior surface of outer member 304 has a plurality of slots 331(a) ... (d) (where d is any number compatible with the dimensions of the outer member). Protrusion 349, disposed on an exterior surface of inner member 302, suitably interfaces with a selected slot 331(a) ... (d) in a substantially mating relationship. A user or patient selects a desired penetration depth by pulling and rotating the outer member 304 such that protrusion 349 abuts an interior surface of a slot 331(a) ... (d). The inner member 302 is held in position; and surface 322(b) is fixed relative to surface 368(a).

Camming surface 341 is disposed in body assembly 328 for attaching assembly 328 to a lancer device. Alternatively, assembly 328 is suitably the distal portion of a lancer device. Camming surface 341 is also suitably utilized to attach a proximal portion of inner member 302 to assembly 328.

Ridge 374 provides a surface that interfaces with spring 327 and biases outer member 304 towards inner member 302.

Alternatively, another design of this embodiment involves the protrusion mounted on the interior of the nose portion 304 and slots located in the inner member 102. This accomplishes the same purpose as the pull and twist embodiment described above. The main difference is that the location of the protrusions and slots has been reversed.

Figure 11A:
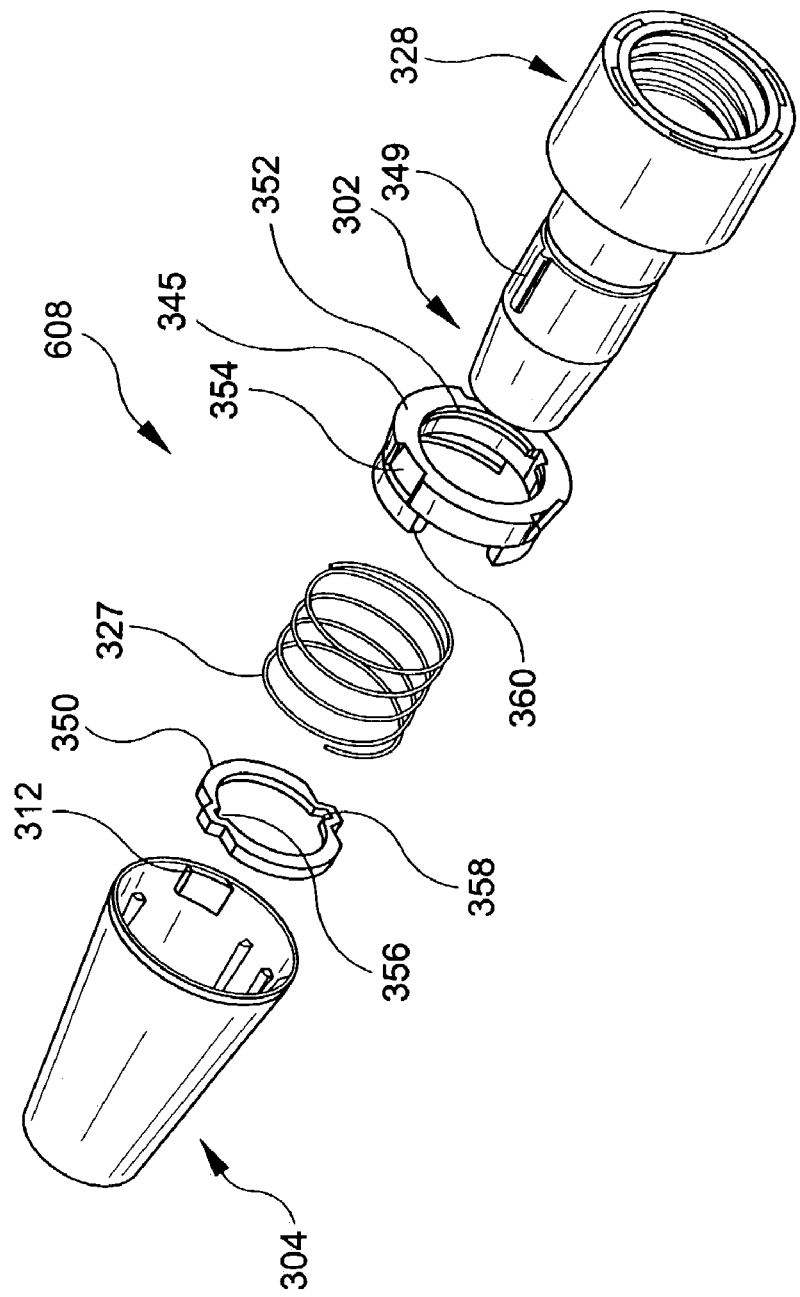
FIGS. 11A, 11B and 11C show a fifth embodiment of the adjustment mechanism.
Figure 11B:
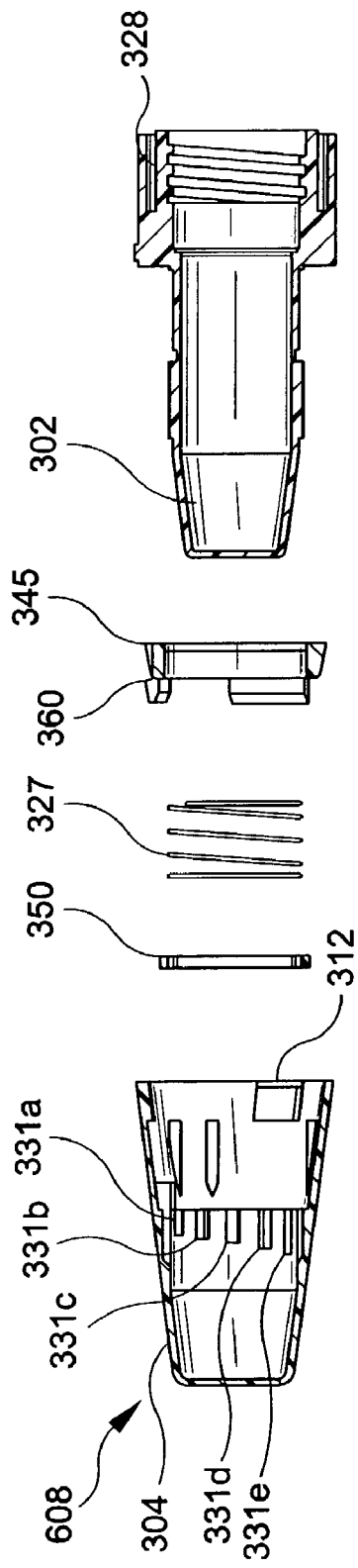
Figure 11C:
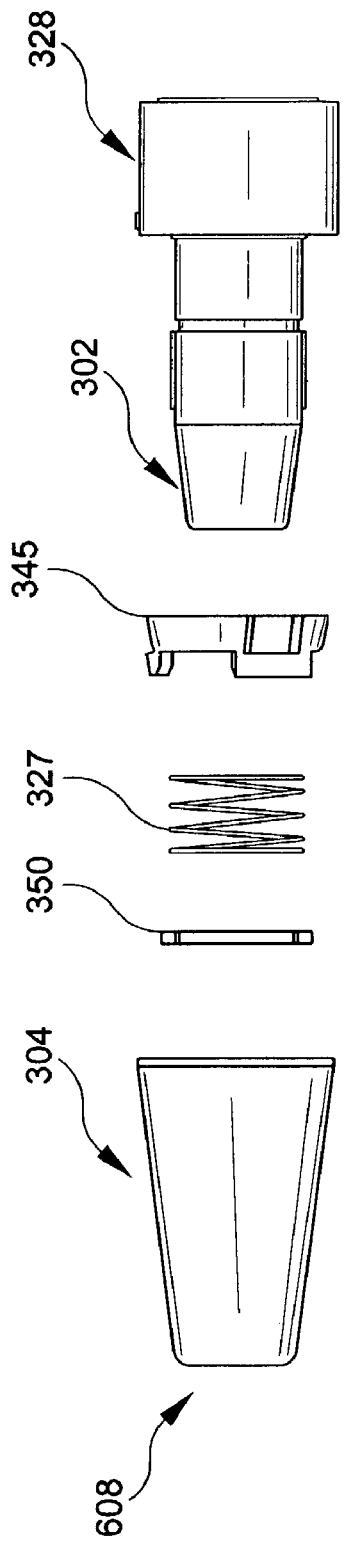

FIGS. 11A, 11B and 11C show exploded views of a fifth embodiment of the adjustment mechanism 608.

FIGS. 11A-11C show nose portion 304, with a protrusion 312. Also shown is a first annular ring member 350, spring 327, a second annular ring member 345, inner member 302 and body assembly 328.

The first annular ring member 350 has notches 356, 358 and the annular ring member 350 is used to retain spring 327. The second annular ring 345 has an extended region 360, one or more notches (shown as numeral 354) and surfaces 352. The first annular ring member 350, spring 327 and second annular ring member 345 provide a connection to hold the inner member 302 in a fixed relationship relative to outer member 304, such that protrusion 349 abuts a selected slot, (slots shown as 331(a) ... (e) in FIG. 11B, although any suitable number of slots is possible) on the interior surface of nose portion 304. Protrusion 312 provides locking for ring 345 into nose 304 by interfacing with notch(es) 354.

Figure 12A:
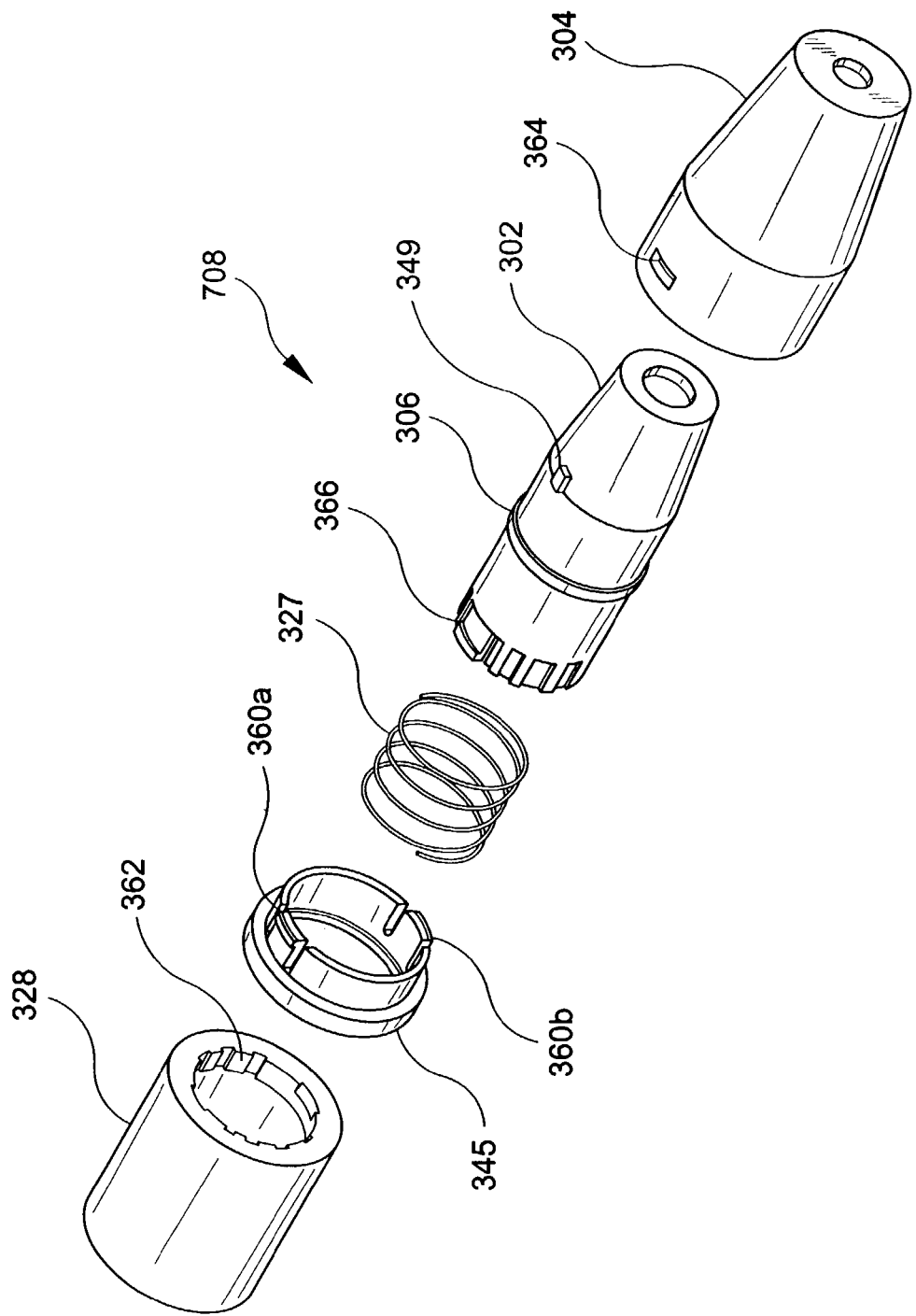
FIGS. 12A and 12B show a sixth embodiment of the adjustment mechanism.
Figure 12B:
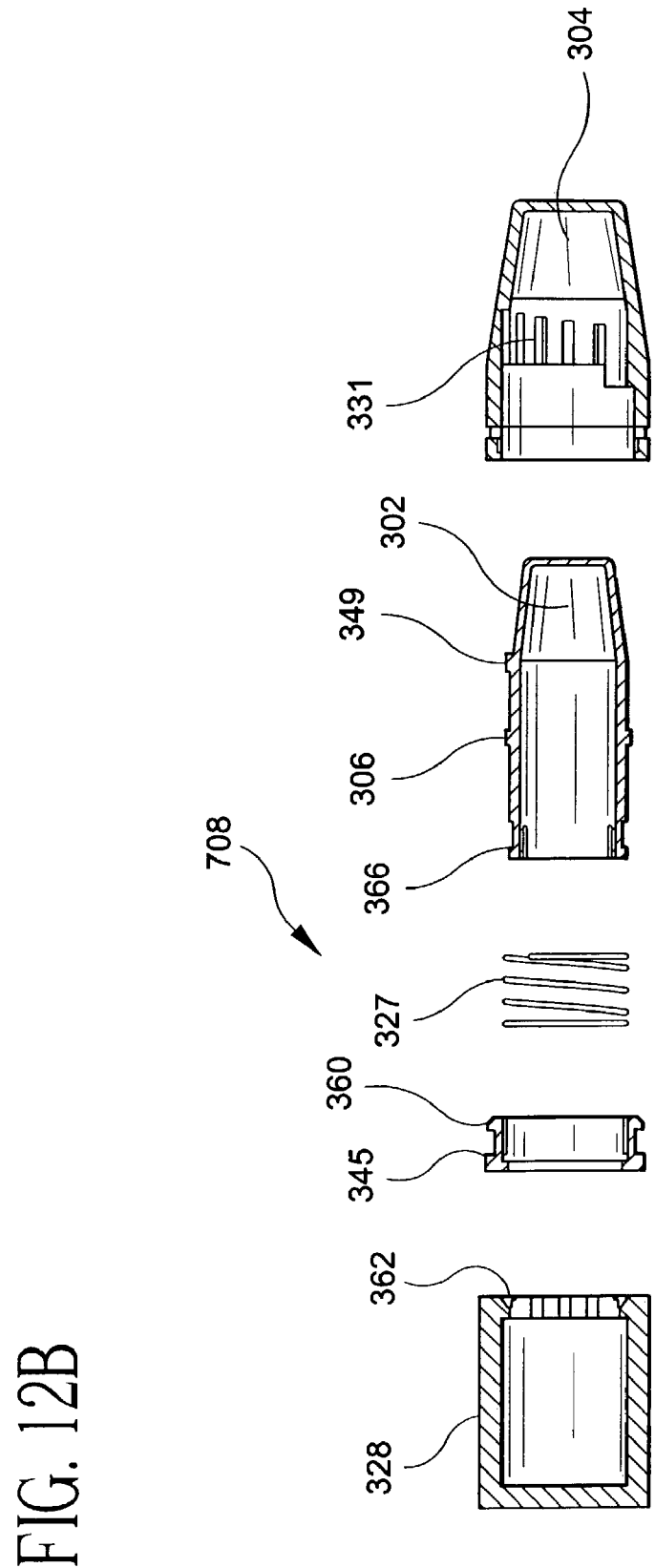

FIGS. 12A and 12B show a sixth embodiment of the adjustment assembly 708. Body assembly member 328 has interior surface 362 for interfacing with surface 366 of inner member 302, thereby affixing inner member 302 to body assembly 328. Ring member 345 has one or more extended surfaces 360 (two surfaces 360(a) and 360(b) are shown, but any suitable number could be used). Extended surfaces 360(a) and 360(b) interlock with aperture 364 of outer member 304. Spring 327 abuts ridge 306 and is inserted into ring 345 to bias the inner member 302 towards outer member 304. The protrusion 349 on inner member 302 interfaces with a selected slot 331 (shown in FIG. 12B), to establish a relationship between inner member 302 and outer member 304.

Figure 13:
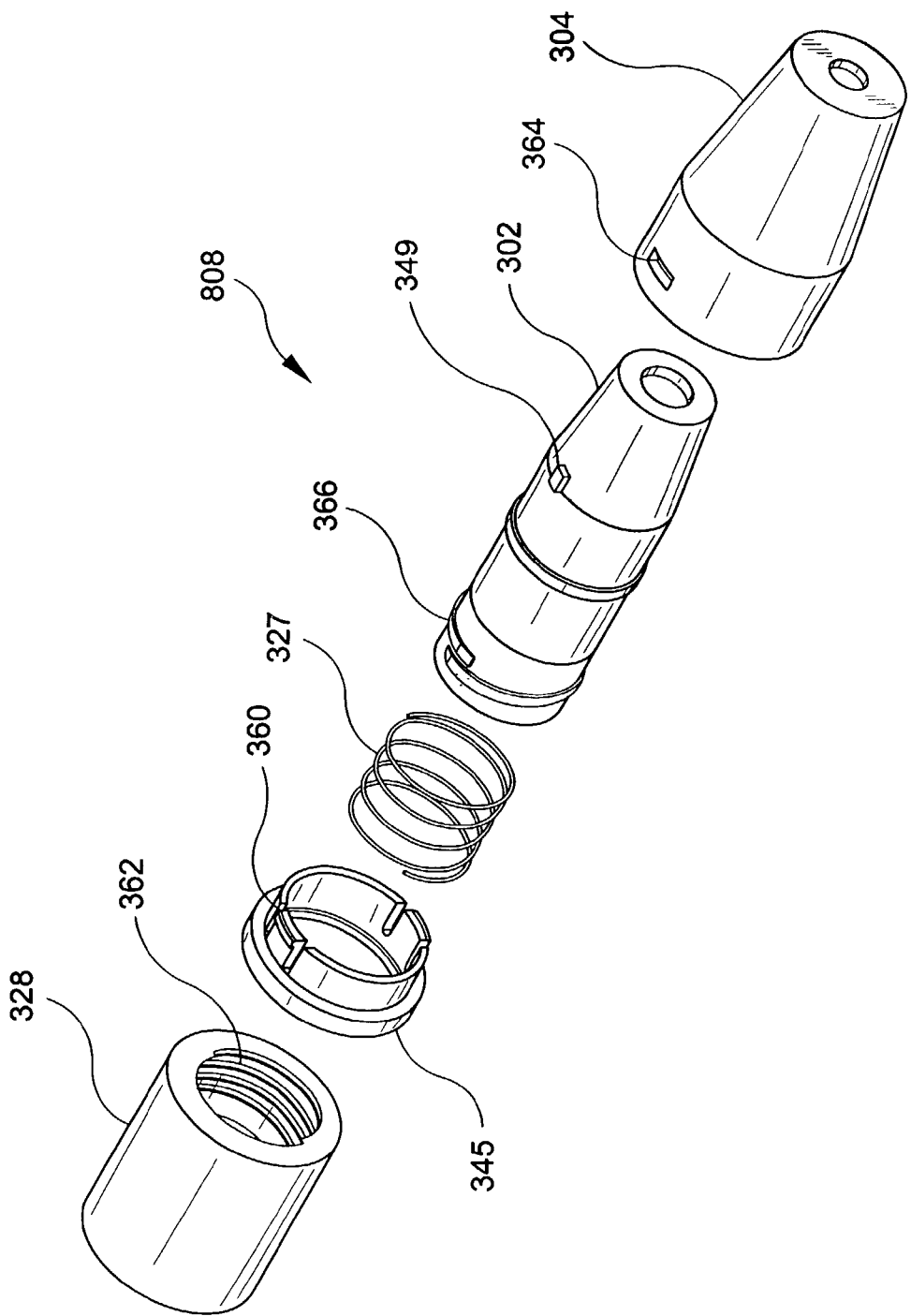
FIG. 13 shows an exploded view of a seventh embodiment of the adjustment mechanism.

FIG. 13 shows a seventh embodiment of the adjustment assembly 808. This embodiment is similar to the sixth embodiment, except that the inner member 302 has a camming surface or, alternatively, screw threads 366, for interfacing and locking with surface 362 of body assembly 328. Similar elements discussed in relation to FIGS. 12A and 12B are not discussed in relation to FIG. 13.

Figure 14:
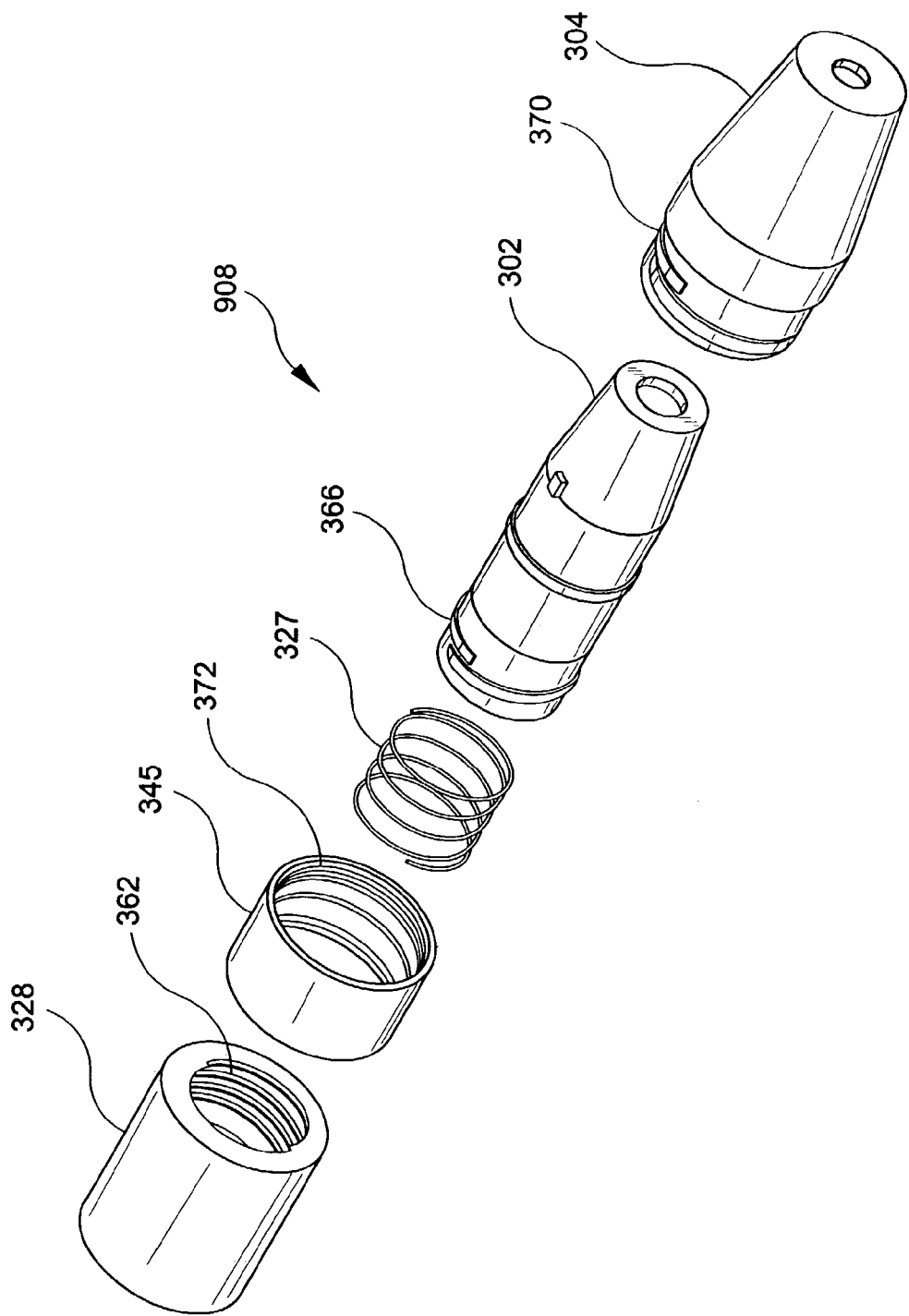
FIG. 14 shows an eighth embodiment of the adjustment mechanism.

FIG. 14 shows an eighth embodiment of the adjustment assembly 908. This embodiment is similar to the sixth and seventh embodiments, except that the outer member 304 has a camming surface or, alternatively, screw threads 370, for interfacing and locking with surface 372 of member 345. Similar elements discussed in relation to FIGS. 12A, 12B and 13 are not discussed in relation to FIG. 14.

Referring back to FIG. 2, arming mechanism 166 is used to arm or cock the lancer device 10, prior to firing, by positioning support mechanism 175 in a state of increased potential energy. Arming mechanism 166 suitably includes inner knob 124, return spring 126 and knob cap 122. The arming mechanism also suitably includes sleeve portion 186, which will also be discussed in relation to the ejection mechanism.

Sleeve portion 186 is typically a hollow, substantially cylindrical structure disposed within body assembly 136 and attaches to body assembly 136 by one or more protrusions shown as element 252 located on the exterior surface of sleeve 186 interfacing with matched detents within the body assembly 136. Protrusions 252 are suitably cantilevered beam members, and any number compatible with the design of sleeve 186 could be used.

Inner knob 124 suitably a cylindrical hollow member and has radial ribs 134 on the exterior surface for preventing rotation of the knob cap 122 during cocking, as well as ensuring minimal movement of knob cap 122 when knob cap 122 is extended. Axial ribs 134 of inner knob 124 prevent rotation of the inner knob 124. Protrusions 564 on inner knob 124 are used to attach inner knob 124 to knob cap 122. Return spring 126 is suitably disposed within inner knob 124 and is used to retract the support mechanism 175 after the lancer device 10 has been fired. This is a safety feature that prevents the stylet from remaining in an extended position after being fired. It also increases patient comfort since the stylet will swiftly retract after puncturing the patient's skin. Knob cap 122 suitably affixes to inner knob 124. Inner knob 124 and return spring 126 are disposed within body section 136. Disposed within the inner knob 124 is proximal portion of support mechanism 175.

Support mechanism 175 suitably includes a support structure (also referred to as a support member, guide member or plunger herein) 146, triggering means 132, and spring retainer 128. At the distal end of plunger 146 a lancet, having a stylet, is suitably mounted. The plunger (guide member) 146 has splines 169, tangs 176, 276 (typically there are any suitable number of tangs, but only two will be described in detail herein), dampening wisp 154, disk members 449(*a*) and 449(*c*) (other disk members are discussed herein) and detents 144(*a*) and 144(*b*).

Plunger 146 is typically an elongated member fabricated from a polymer material, enabling it to be relatively rigid at the distal portion, where it interfaces with a lancet, suitably by having a receptacle (receptacle not shown in FIG. 2) with dimensions sized to hold a proximal portion of a lancet in a mating relationship. Splines 169 enhance a linear pull motion to arm the device 10.

Tangs 176, 276 are protrusions extending outwardly from the plunger 146. (There may be more or less than two tangs on plunger 146, but only two are depicted in FIG. 2.) The tangs 176, 276 are suitably wedge-shaped to engage yoke latch 139 and hold plunger 146 in a fixed position after device 10 is armed and prior to its firing.

Triggering means 132 is suitably a coil spring that is capable of being compressed and is disposed around splines 169, although any suitable material could be used to perform the function. Triggering means 132 is compressed when the knob cap 122 is retracted. In a compressed state, the triggering means 132 has higher potential energy.

Dampening mechanism is suitably one or more protrusions or wisps 154 (although there could be virtually any number of wisps that would comport with the design, only a single wisp will be described herein), which is, for example, a radially outward biased cantilevered beam located on plunger 146. When the plunger 146 is actuated, the wisp 154 contacts the inner diameter of sleeve portion 186 or body section 136, if sleeve portion 186 is omitted, to provide a frictional force and thus a dampening feature to the plunger 146. This dampening mechanism reduces vibration felt by the patient during plunger movement, which is typically during and shortly after stylet penetration.

Upon assembly, detents 144(*a*) and 144(*b*) are pushed through a slit 212 in spring retainer 128 and expand so as to maintain plunger 146 and return spring 126 in a desired position to allow for arming and plunger retraction. In a preferred embodiment, plunger 146 and spring retainer 128 would be a single piece.

Triggering mechanism 172 is used to fire the lancer device 10 such that a desired portion of a stylet is projected through nose orifice 184. Triggering mechanism 172 comprises, yoke latch 139, biasing means 142, and button 138.

Yoke latch 139 is suitably a U-shaped or C-shaped rigid member although virtually any suitable shape would be acceptable for forming a substantially interference fit with tangs 176, 276 on plunger 146 and disposed in body assembly 136. Yoke latch 139 has windows (not shown in FIG. 2) for interfacing with tangs 176, 276 so as to control the position of tangs 176, 276. When the lancer device 10 is in the loaded position, the yoke latch 139 engages tangs 176, 276 such that plunger 146 remains in a state of higher potential energy (i.e., triggering spring 132 is compressed).

Biasing means 142 is disposed between plunger 146 and yoke latch.139, and biases, radially outward, the latch 139. When actuated the bias means 142 is overcome, releasing yoke latch 139 thereby permitting tangs 176, 276 to pass through yoke latch 139 and plunger 146 pushes a lancet in the distal direction toward nose portion 104. The biasing means 142 is suitably a leaf spring, coil spring, compressible elastomeric material such as a foam rubber cube, cantilevered beam, torsion spring or plastic member. The biasing means as shown as leaf spring 142 in FIG. 2, which is actuated by button 138. Button 138 includes cantilevered portion 192 and cavity 194.

The release member, or button, 138 has a bottom surface 262 that contacts yoke latch 139 to overcome bias means, which is shown as a leaf spring, 142. Protrusion 238 retains the button 138 in the body assembly 136. Button 138 is typically mounted through button orifice 216 of body assembly 136. This design allows linear travel of the plunger 146 because the plunger 146 is not biased in any direction due to trigger activation. The straighter plunger path reduces vibration and radial motion and thus reduces pain felt by the patient.

Figure 15A:
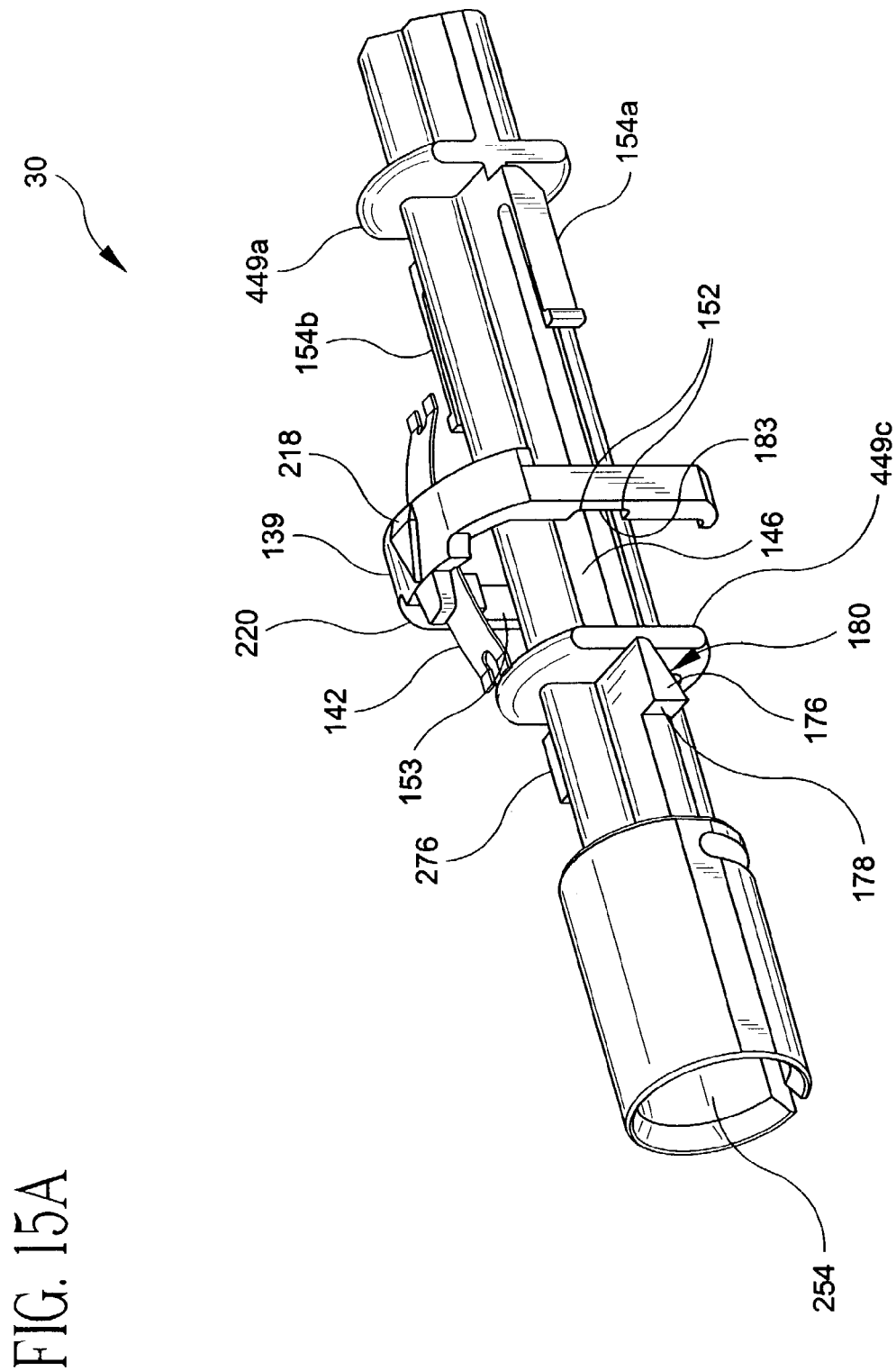
FIGS. 15A and 15B show an isometric view of a support member as it relates to the triggering mechanism of the lancer device.
Figure 15B:
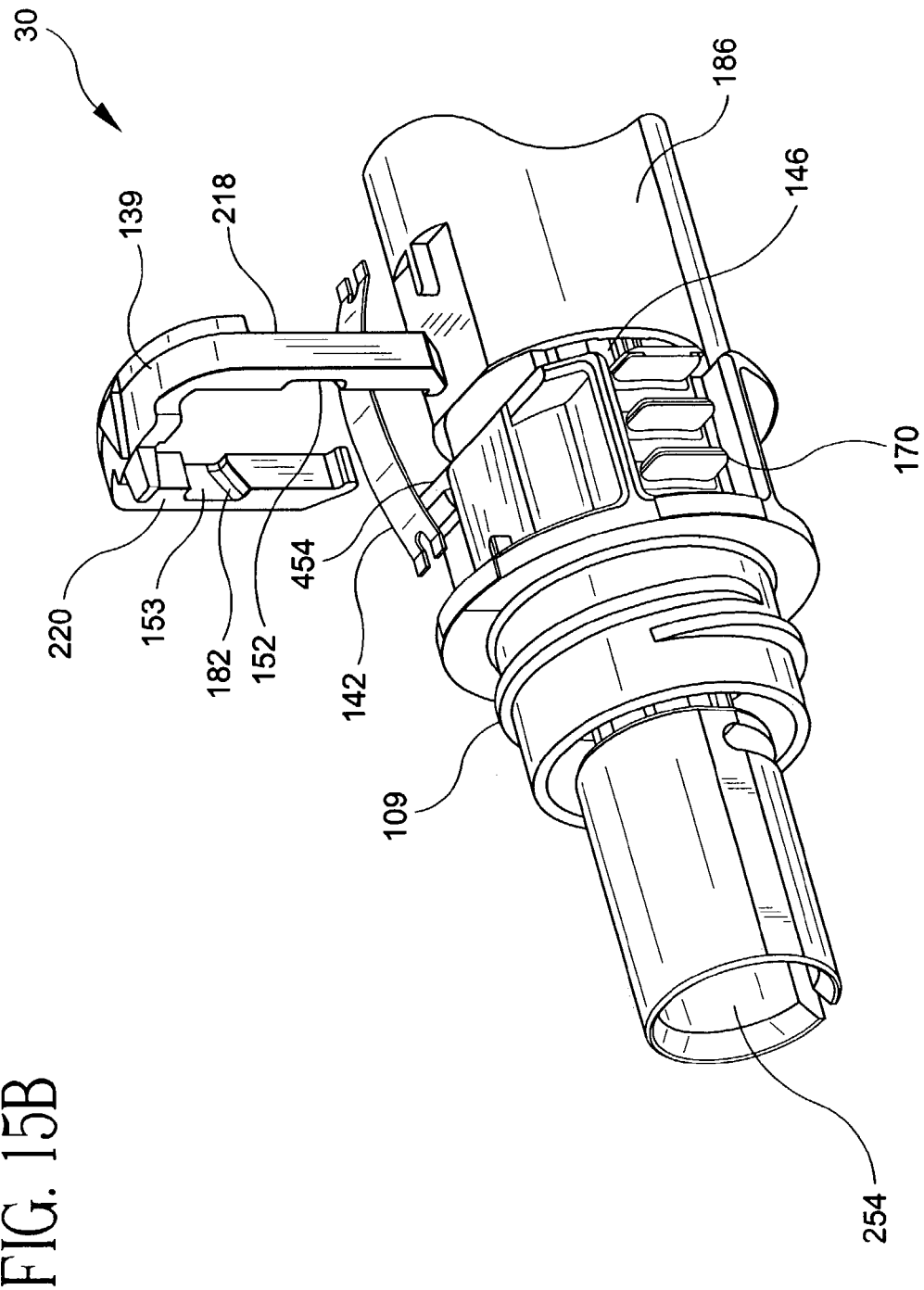

FIGS. 15A and 15B show an isometric exploded view 30 of the yoke latch 139 and plunger member 146. The plunger member 146 has a receptacle 254 sized to interface with a lancet in a substantially mating relationship. FIG. 15A shows a view without a sleeve and FIG. 15B shows a view with sleeve 186. As shown in FIGS. 15A and 15B, the yoke latch 139 has proximal face 218 and distal face 220, and mounts over the biasing means 142. The yoke latch 139 has yoke latch windows (also referred to as notches herein) 152, 153 and yoke latch distal face ramps 182, 183 (ramp 183 shown in FIG. 15A and ramp 182 shown in FIG. 15B). These sections of yoke latch 139 facilitate movement by plunger 146.

FIG. 15A shows tangs 176 and 276 disposed on opposing sides of plunger 146. It should be apparent to those skilled in the art that the quantity and location of the tangs, which are substantially wedged-shaped protrusions, is a design choice. Tang 176 has a distal face 178 perpendicular to the line of action, which acts to rest on yoke latch proximal face 218 when the plunger member 146 is retracted into the "armed" position. The tang 176 is angled to form a ramp 180 that can act on a corresponding ramp 183 of the distal face 220 to the proximal face 218 of the yoke latch 139. Tang face 178 engages proximal face 218 of yoke latch 139 when in an armed state. By pulling the plunger 146 in the proximal direction such that the plunger tang ramp 180 engages the yoke latch distal face 220, the yoke latch 139 is moved in a downward direction by the ramp 180 surface. As the yoke latch 139 lowers, the tangs 176, 276 move through yoke latch windows (or notches) 152, 153. Once the tangs 176, 276 are through windows 152, 153, the yoke latch 139 snaps upward into a fixed position due to pressure exerted by biasing means 142. This fixed position of yoke latch 139 prevents movement of the plunger 146.

The plunger 146 suitably has a non-circular cross-section as shown in FIG. 15A. The plunger 146,is relatively rigid and resists columnar deformation thereby providing support and guidance for a lancet as the lancet is propelled.

In order to arm the device, the knob cap (shown as element 122 in FIG. 2) is retracted. Tangs 176, 276 on plunger 146, which typically have a wedge shape, displace latch 139 radially inward against the bias of the biasing means shown as 142. In doing so, they are allowed to pass through the window 152 and while passing through the window, force the latch 139 into a fixed position. However, since a proximal force is being applied to the plunger 146 against the bias of the triggering spring (shown as element 132 in FIG. 2), the motion continues proximally as the tangs 176, 276 pass entirely through the yoke latch 139. Once the tangs 176, 276 are positioned on the proximal side of the latch, the bias of the leaf spring 142 forces the yoke latch 139 radially outward to the "armed position". Tangs 176, 276 continue slightly passed the yoke 139 and are stopped due to the position of the plunger 146. The plunger 146 is released and then, due to bias of trigger spring, moves distally to the recover distance and rest in a fixed position against the proximal face 218 of yoke latch 139.

In order to fire the device, the release member (shown as button 138 in FIG. 2) is pressed, which biases the yoke latch 139 against the bias means, shown as leaf spring 142 and subsequently the tangs 176, 276 on the plunger 146 are allowed to pass through the windows 152, 153 on the yoke latch 139. Since the plunger 146 is biased by triggering spring (shown as element 132 in FIG. 2), this occurs rapidly. This design allows linear travel of the plunger 146 because the plunger 146 is not biased in any direction due to trigger activation. The straighter plunger path reduces vibration and radial motion.

After the axial travel of the tangs 176, 276 passed through the windows 152, 153; yoke latch 139 returns to its rest position.

The plunger 146 also has one or more protrusions 449 (these protrusions are shown in FIG. 15A as 449(a) and 449(c); but are described herein as disk-like members 449(a) . . . (d), although any suitable number of protrusions could be used), that form one or more annular rings around plunger 146. This ring is typically non-circular, thereby engaging the inner diameter of the device. These members 449, which are suitably used in conjunction with wisps 154(a) and 154(b) and/or tangs 176, 276, provide a centering function for the plunger 146 when the plunger 146 is propelling a lancet.

FIG. 15B shows an exploded view of the latch 139, plunger 146 and sleeve portion 186. FIG. 15B also shows threaded portion 109 of sleeve portion 186 and grooved region 190 of sleeve 186. Threaded portion 109 is suitably connected to adjustment collar or the tip thread member to connect the adjustment mechanism to the sleeve 186. The leaf spring 142 is engaged by the sleeve 186 to exert pressure on yoke latch 139. Slotted region 454 of sleeve 186 permits access of plunger 146 to yoke latch 139. Elements discussed in relation to FIG. 15A are not discussed in relation to FIG. 15B.

Figure 16A:
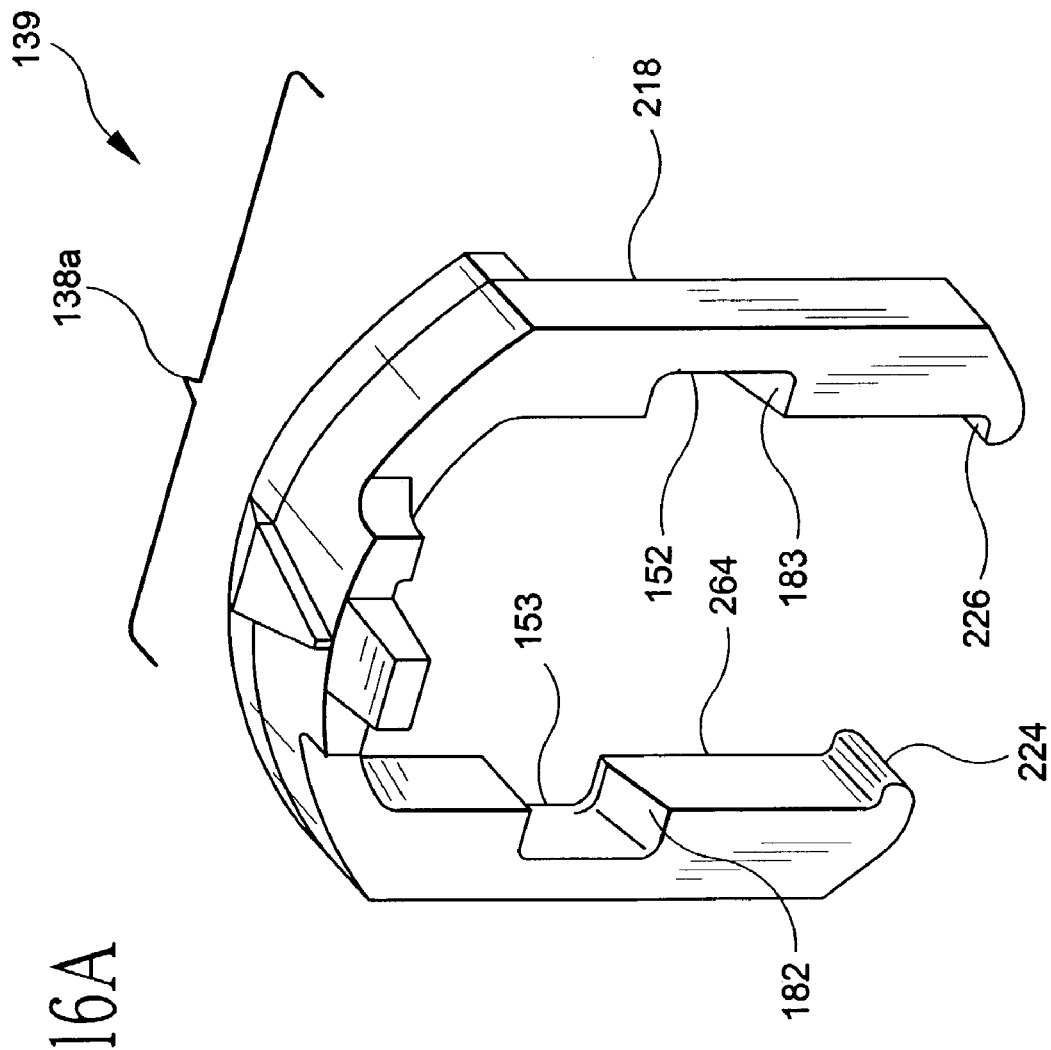
FIGS. 16A and 16B show a perspective view of a yoke latch of the lancer device.
Figure 16B:
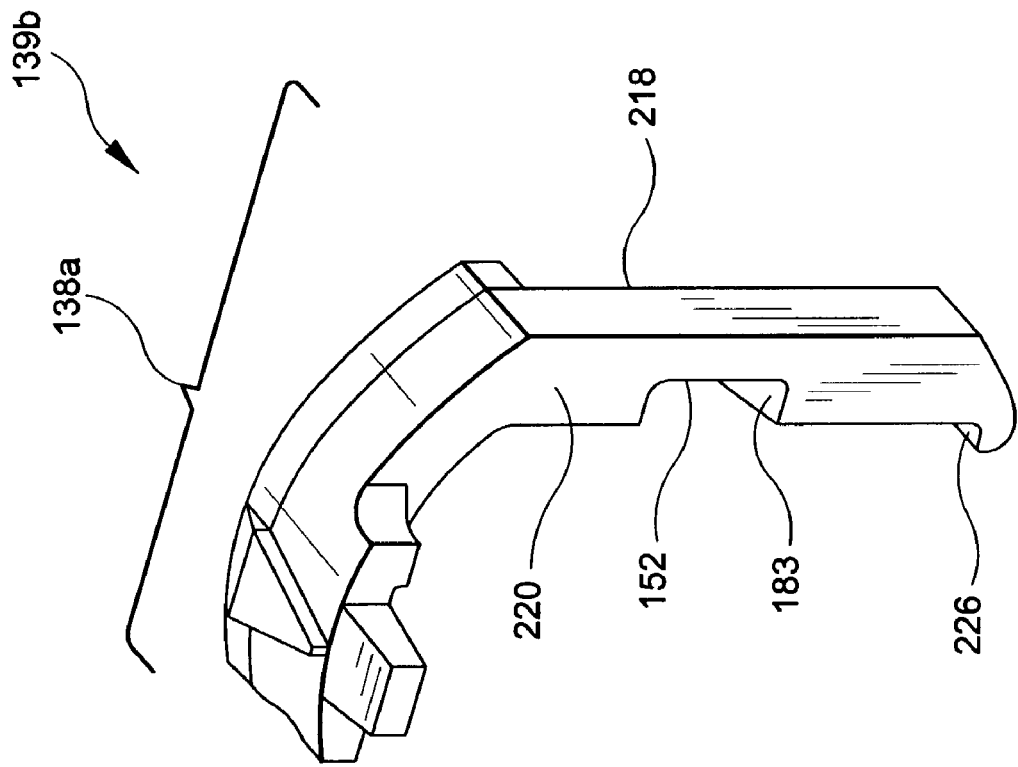

FIGS. 16A and 16B show a perspective view of yoke latch 139. As shown in FIG. 16A, the yoke latch 139 typically has a substantially U-shape or C-shape design such that the support member passes through interior surface 264 through notches 152 and 153 of yoke latch 139. However, the yoke latch 139 suitably can be a member containing a notch for engaging a tang as shown in FIG. 16B.

As shown in FIG. 16A, the yoke latch 139 has windows 152, 153 and ramp surfaces 182, 183. The windows 152, 153 enable the plunger member to slide through the yoke latch 139 to the proximal side 218, and to be held in a fixed relationship until actuated by pressure applied to an area 138(a), which overcomes the biasing means (not shown in FIG. 16). Yoke latch 139 also has clamping portions 224, 226 disposed at the open end, for securely holding the yoke latch in position relative to sleeve via a slotted area in the sleeve. (Slotted area in sleeve is shown as element 454 in FIG. 15B.)

FIG. 16B shows yoke latch 139(b), which is a modified version of yoke latch 139 shown in FIG. 16A. Yoke latch 139(b) does not have a U-shaped or C-shaped design; but instead, performs the latching function with a single notch 152, a single ramp surface 183, and a single clamping mechanism 226. The area to apply pressure 138(a) is also approximately half the similar area of FIG. 16A.

Figure 17:
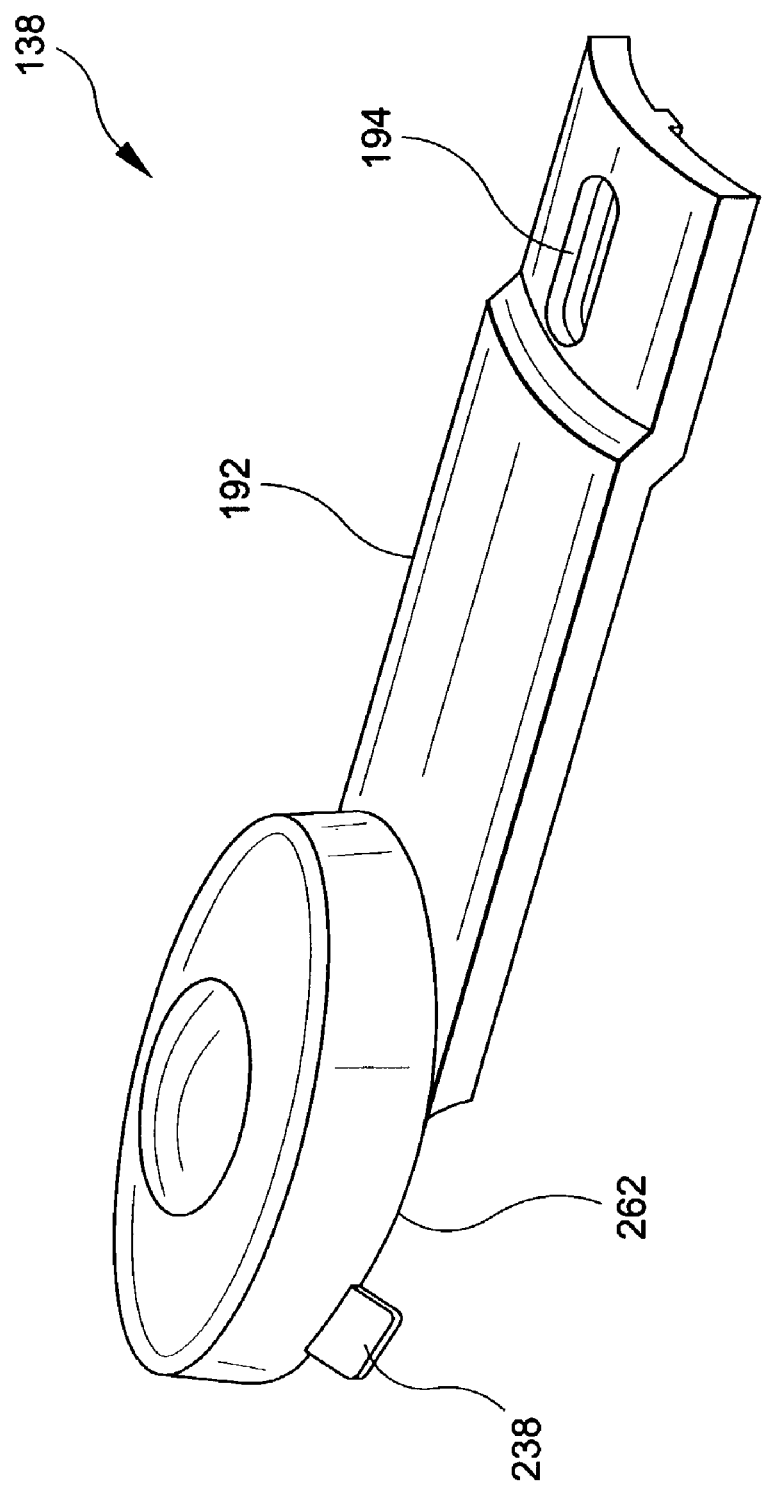
FIG. 17 shows a perspective view of a button of the lancer device.

FIG. 17 shows the button 138 having cantilevered portion 192 and cavity 194. The cantilevered portion 192 facilitates a substantially mating relationship with the body assembly. The cavity 194 suitably interlocks with the body assembly. Button tang 238 (typically button 138 will have two tangs, but only one is shown in FIG. 17) is suitably a cantilevered member that forms a substantially interference fit with the body assembly when inserted into the button orifice (body assembly and button orifice shown in FIG. 2). The button tang 238 prevents button 138 from detaching from the body assembly. The button 138 has a surface 262 in proximity to the yoke latch. As is obvious to those skilled in the art, the button could be formed on the yoke latch. The button is an optional feature and a user could activate the device by pressing directly on a portion of the yoke latch (shown as 138(a) in FIG. 16). A portion 262 of button 138 abuts the yoke latch to overcome the biasing means when the button 138 is pushed with the necessary force.

Figure 18:
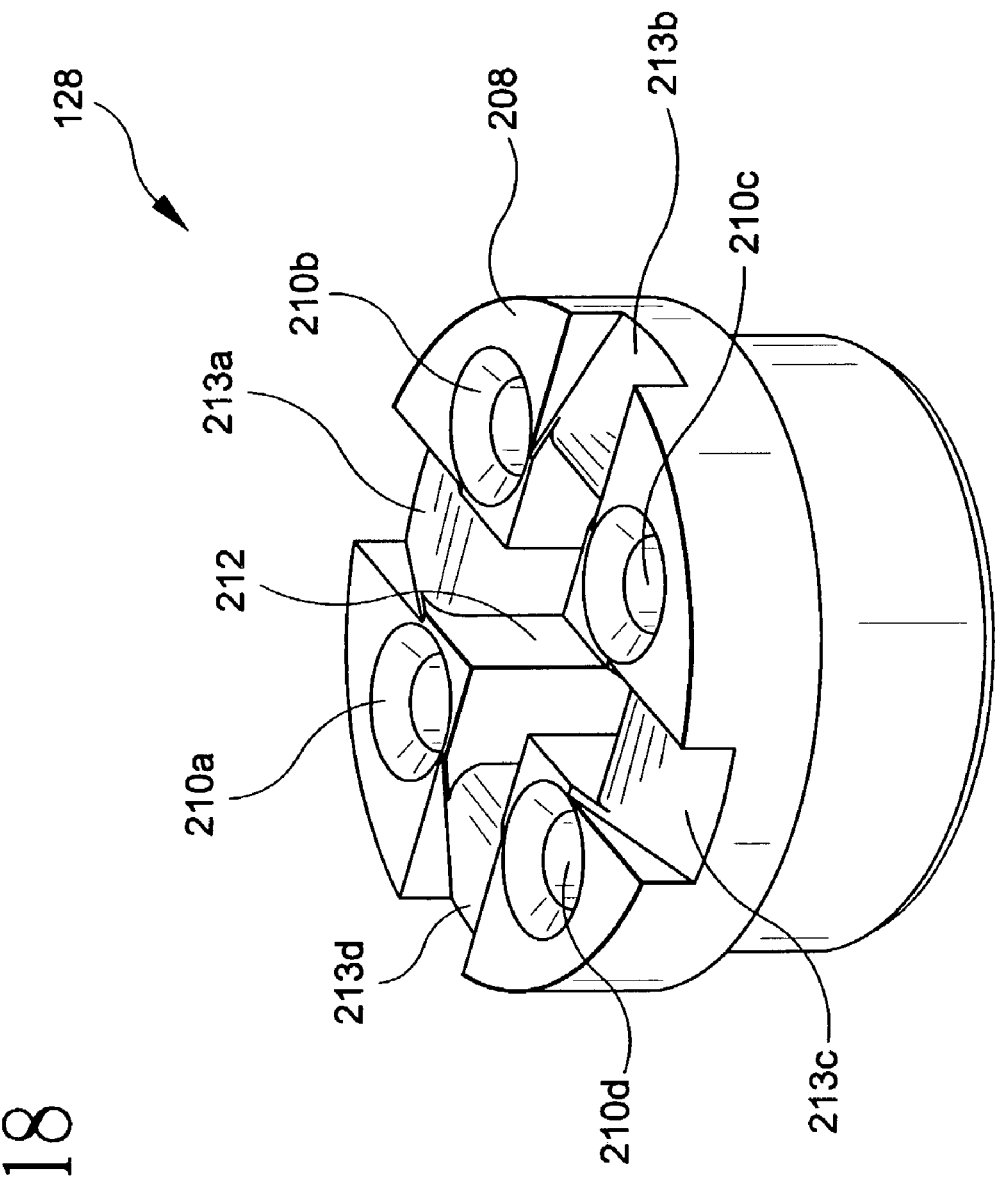
FIG. 18 shows a perspective view of a retaining member used with the lancer device.

FIG. 18 shows spring retainer 128. Retainer 128 has an orifice 212 for providing a substantially smooth fit with the plunger member (plunger not shown in FIG. 18). The orifice 212 has an interior surface corresponding to the outer diameter of the plunger. The retainer 128 has a non-circular interior surface for creating a substantially mating relationship with plunger member as shown herein. The interior surface of retainer 128 is suitably any configuration to interact with the plunger. Surface 208 is a proximal surface having one or more orifices 210 (a)-(d).

The retainer 128 also suitably has inclined surfaces 213(a) . . . (d) for interfacing with the proximal portion of a plunger, typically the detents of the plunger hook into the inclined surfaces 213(a) . . . (d). These surfaces facilitate the retainer 128 maintaining the plunger relative to the retainer 128 and allowing the retainer 128 to retract the plunger when the retainer 128 is retracted. The retainer 128 also retracts the plunger when the retainer 128 is retracted by the return spring. (Although only four inclined surfaces are shown, typically any number compatible with the design of retainer 128 could be used.)

Figure 19:
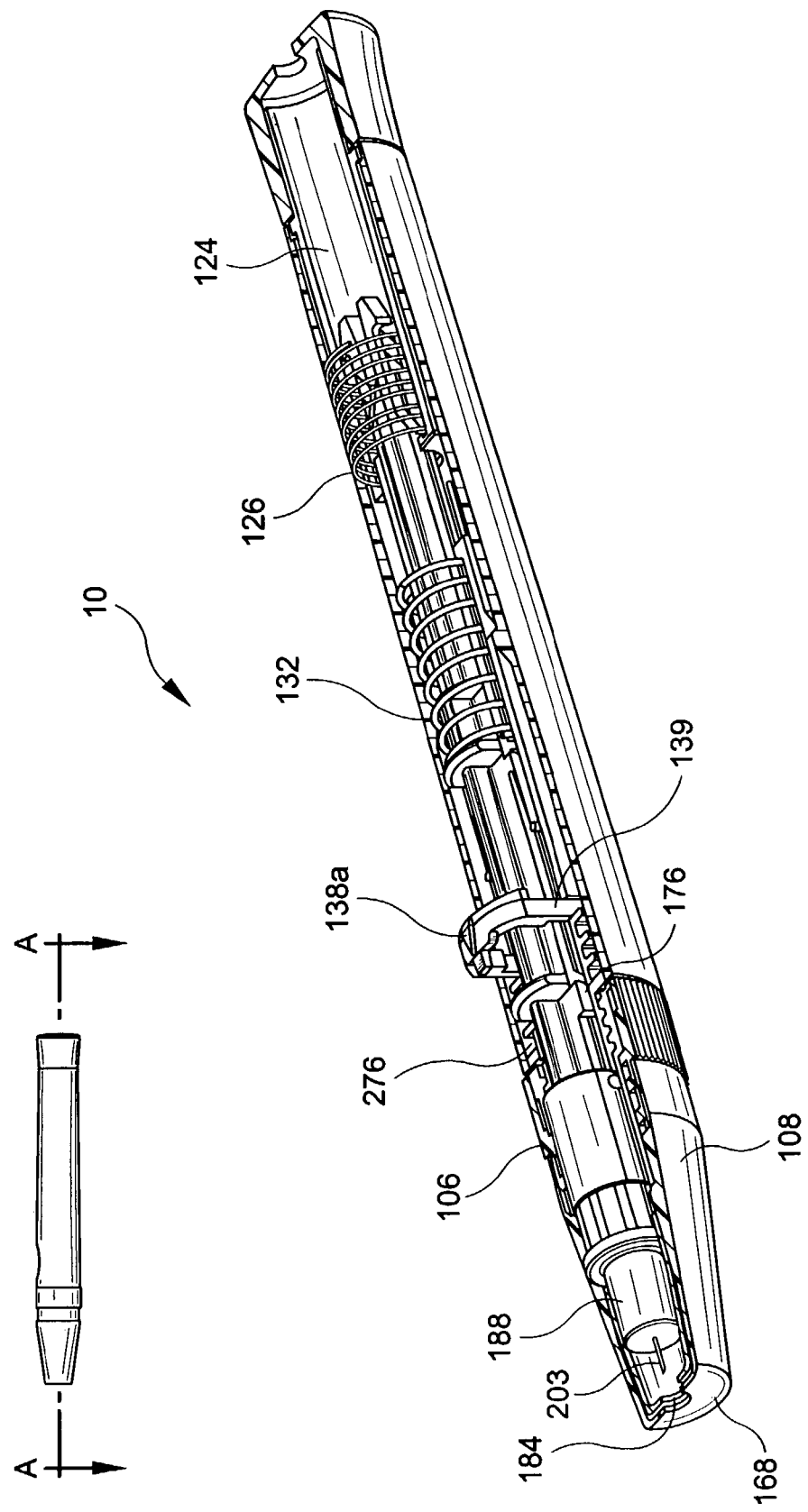
FIG. 19 shows a cut-away view of the lancer device in a resting position.

FIG. 19 shows a cut-away view of the lancer device 10 in the pre-armed, or resting, stage. As shown in FIG. 19, lancet 188 has a sharpened stylet portion 203 that is within device 10 and poised to emerge from orifice 184 when the device 10 is fired or actuated. In the pre-armed position, triggering spring 132 is in an open position (i.e., a state of relatively low potential energy) because it is substantially non-compressed. Return spring 126 is also not fully compressed. Tangs 176, 276 are positioned on the distal side of yoke latch 139. Inner knob 124 is in a non-extended position. The biasing means (not shown in FIG. 19) is biasing yoke latch 139.

Distal surface 168, adjustment mechanism 108, and collar 106 have been discussed previously and will not be discussed further here.

Figure 20:
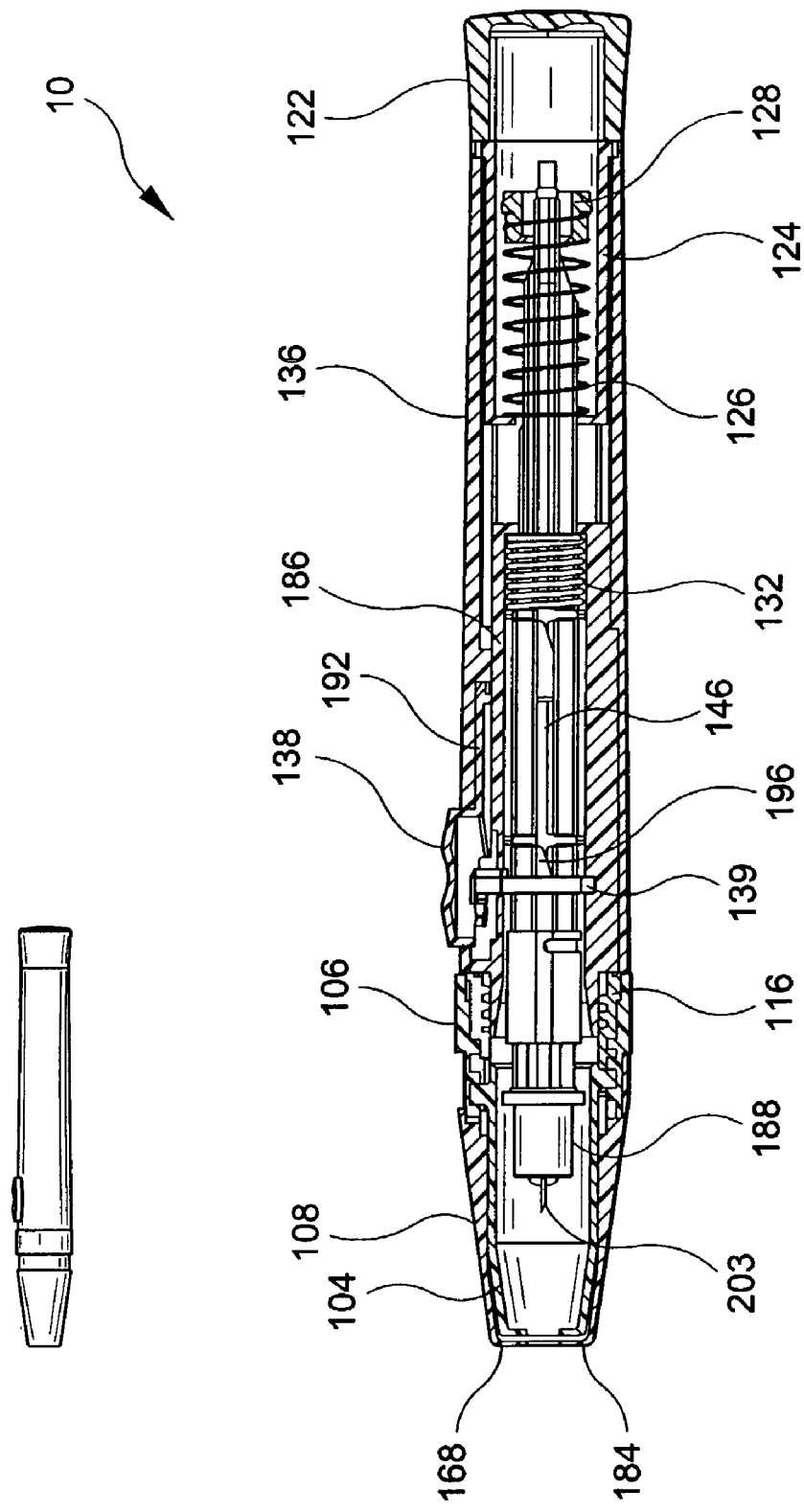
FIG. 20 shows a cut-away view of the lancer device in an armed position.

FIG. 20 shows a cross-sectional view, taken along the longitudinal axis of the lancer device 10 in the armed position. Similar elements previously described will not be discussed in relation to FIG. 20. Similar to the view shown in FIG. 19, the lancet 188 with sharpened end portion 203 is disposed such that the stylet 203 does not emerge from orifice 184. Trigger spring 132 has been compressed, i.e., in a state of increased potential energy by retraction of end knob 122 in the proximal direction. Tang 176 is positioned on the proximal side of latch 139. Knob cap 122 is not extended.

Figure 21:
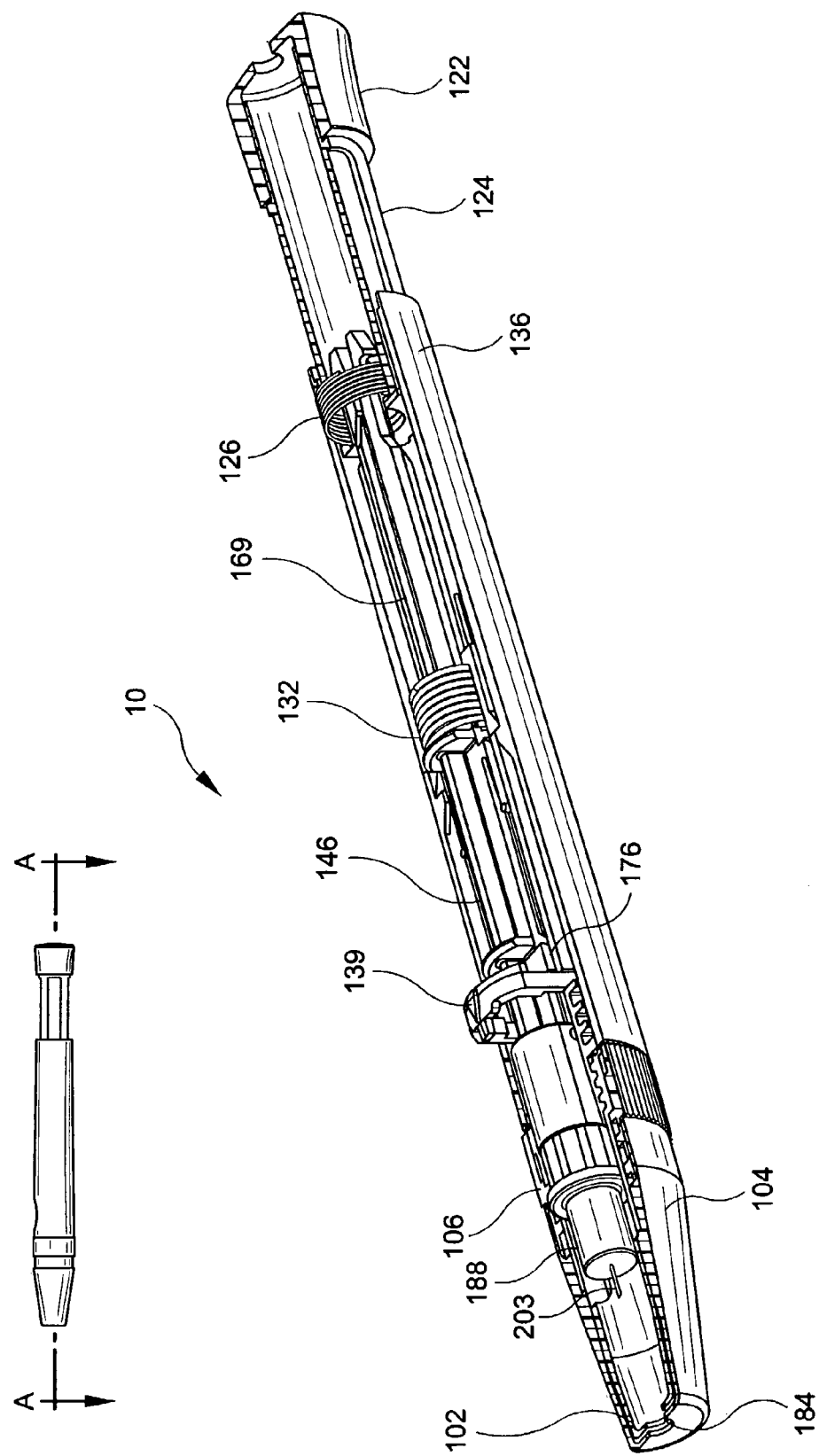
FIG. 21 shows a cut-away view of the lancer device in an armed position with an end knob extended.

FIG. 21 shows a cut-away view of the lancer device 10 in the armed position with knob cap 122 extended so as to expose a section of inner knob 124. In this position tang 176 is on the proximal side of yoke latch 139. The triggering spring 132 is compressed because plunger 146 has been retracted by knob cap 122.

In the armed position, the knob cap 122 returns to proximal end of body assembly 136, due to the bias of the return spring 126 (e.g., coil spring).

In order to actuate the lancer device 10, the latch 139 must be pushed with the necessary force to overcome or compress the biasing means and move the yoke latch 139 to a fixed position.

When button 138 is deliberately pressed with the requisite amount of pressure, the biasing means, such as a leaf spring is overcome, permitting the yoke latch 139 to move and tang 176 to pass through yoke latch 139, causing plunger 146 to push lancet 188 in the distal direction. The stylet 203 extends from the nose orifice 184.

After the stylet 203 emerges from the nose orifice 184, lancet 188 impacts lancet stop 102, and return spring 126 pulls the stylet 203 back into the lancer device 10.

The lancer 188 has a stylet 203 that is suitably manufactured from stainless steel.

Nose portion 104, collar 106 and splines 169 have been discussed previously in relation to other figures and are not discussed further here.

Figure 22:
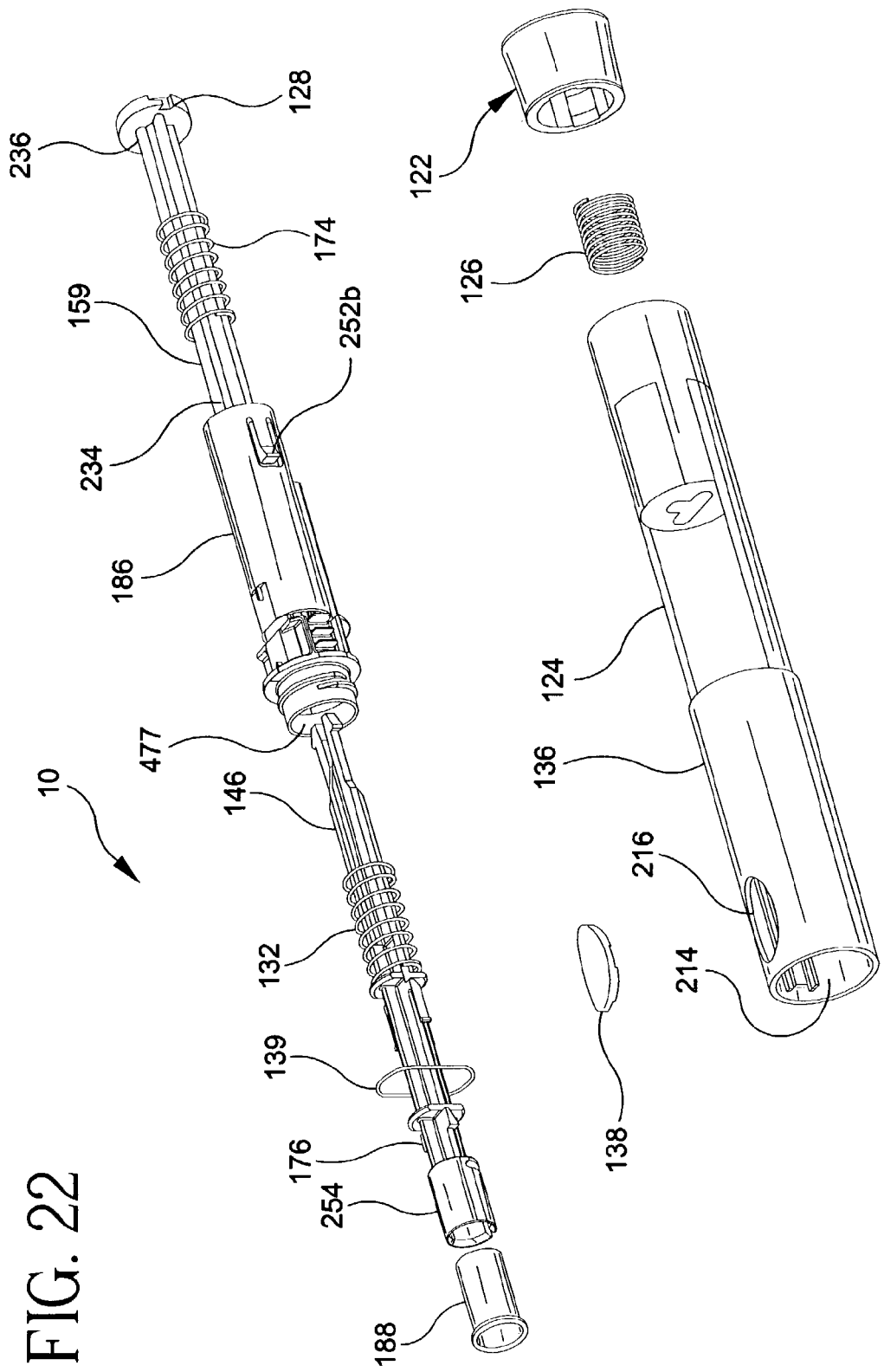
FIG. 22 shows an exploded view of the lancer device with an ejection mechanism.

FIG. 22 shows an exploded view of an embodiment of device 10 that has an ejection feature. An ejection mechanism is used to eject a used lancet 188 from lancer device 10. The ejection mechanism comprises an ejection member in (also referred to as an ejection blade herein) 159, sleeve 186 (shown in FIG. 2 previously), and ejection spring 174. The ejection mechanism operates in conjunction with other components of the device 10.

Ejection member or blade 159 (the terms "ejection member" and "ejection blade" are used interchangeably herein) is suitably a rigid elongated member, fabricated from a polymer material, having distal portion 234 and proximal portion 236. Ejection blade 159 is mounted in the proximal portion of body assembly 136, suitably to retaining plug 128 such that the blade 159 is affixed to the inner diameter of body assembly 136. Typically, the blade 159 would be integral to the body assembly 136. Ejection member 159 has a distal portion 234 for interfacing with the lancet 188. A portion of ejection blade 159 may also be disposed in sleeve 186, which is disposed in body section 136, or alternatively, the ejection blade 159, may be disposed in body section 136, without sleeve 186.

Sleeve 186 is used to provide support for the ejection blade 159 and to provide a connection between the body section 136 and nose cap. The sleeve 186 has a one or more protrusions, or camming features shown as 252(*a*) and 252(*b*), which is suitably two cantilevered beams that are displaced when the end knob 122 is retracted while the nose portion is detached from body assembly 136.

The proximal end of sleeve 186 permits the plunger 146 to move axially within sleeve 186. As shown, the sleeve 186 has an interior surface configuration that forms a substantially interference fit, such that the clearance between the plunger 146 and the inner diameter of the sleeve 186 is minimized. Although the configuration is non circular, virtually any configuration would be acceptable.

Ejection spring 174 is suitably a coil spring capable of being compressed that is disposed between proximal portion 236 of blade 159 and the distal portion 236. Sleeve 186 is typically fixed to the body assembly 136; but is also capable of restricted axial movement. Ejection spring 174 is used to bias sleeve 186 in the distal direction. As the plunger 146 is moved proximally, the sleeve 186 moves proximally against bias of the ejection spring 174. The distal portion of the blade 234 contacts lancet 188 and prevents it from retracting in body assembly 136, and thus, lancet 188 becomes detached from plunger receptacle 254. The detached lancet 188 is not retained and will suitably exit through body orifice 214.

In operation, the ejection mechanism enables a used lancet to be removed from the device without a user or patient touching it.

The ejection feature will now be described. After a stylet has been fired, by releasing latch 139, and is retracted into the body assembly 136 by return spring 126, the nose cap and/or the entire adjustment mechanism is removed. Knob cap 122 can be retracted further when the nose cap is detached because the nose cap is not exerting a force on body assembly 136 because it is no longer connected to sleeve 186.

A user or patient pulls on the end knob 122 in a similar fashion as the arming force to a first position, however, with the nose cap removed the knob cap 122 can be retracted further in the proximal direction than during the arming process. The return spring 126 is compressed first. Upon further retraction of knob cap 122 to a second position, which is further in the proximal direction than the first position, retainer 128 and plunger 146 are retracted, compressing triggering means shown as triggering spring 132. Next, sleeve 186 is retracted axially, in the proximal direction, compressing ejection spring 174. Ejection spring 174 is biased to maintain the sleeve 186 in a distally forward position. The movement of plunger 146 and sleeve 186 in the proximal direction causes lancet 188 to come into contact with ejection blade 159. Lancet 188 contact with the ejection blade 159 prevents the lancet 188 from retracting further and thus, lancet 188 is detached from plunger 146. A user can point the distal portion of the body assembly 136 into an appropriate refuse container and the lancet 188 will fall out of the lancer device 10 through body orifice 214.

Thus, the ejection mechanism permits disposal of a used lancet 188 without a user touching it, and without an additional control member.

In an alternate embodiment, the sleeve 186 has a protrusion 477 mounted on the inner diameter that serves to prevent the lancet 188 from retracting and thereby detaching the lancet 188 from the plunger 146.

Button 138, inner knob 124 and button orifice 216 have been discussed previously.

Figure 23:
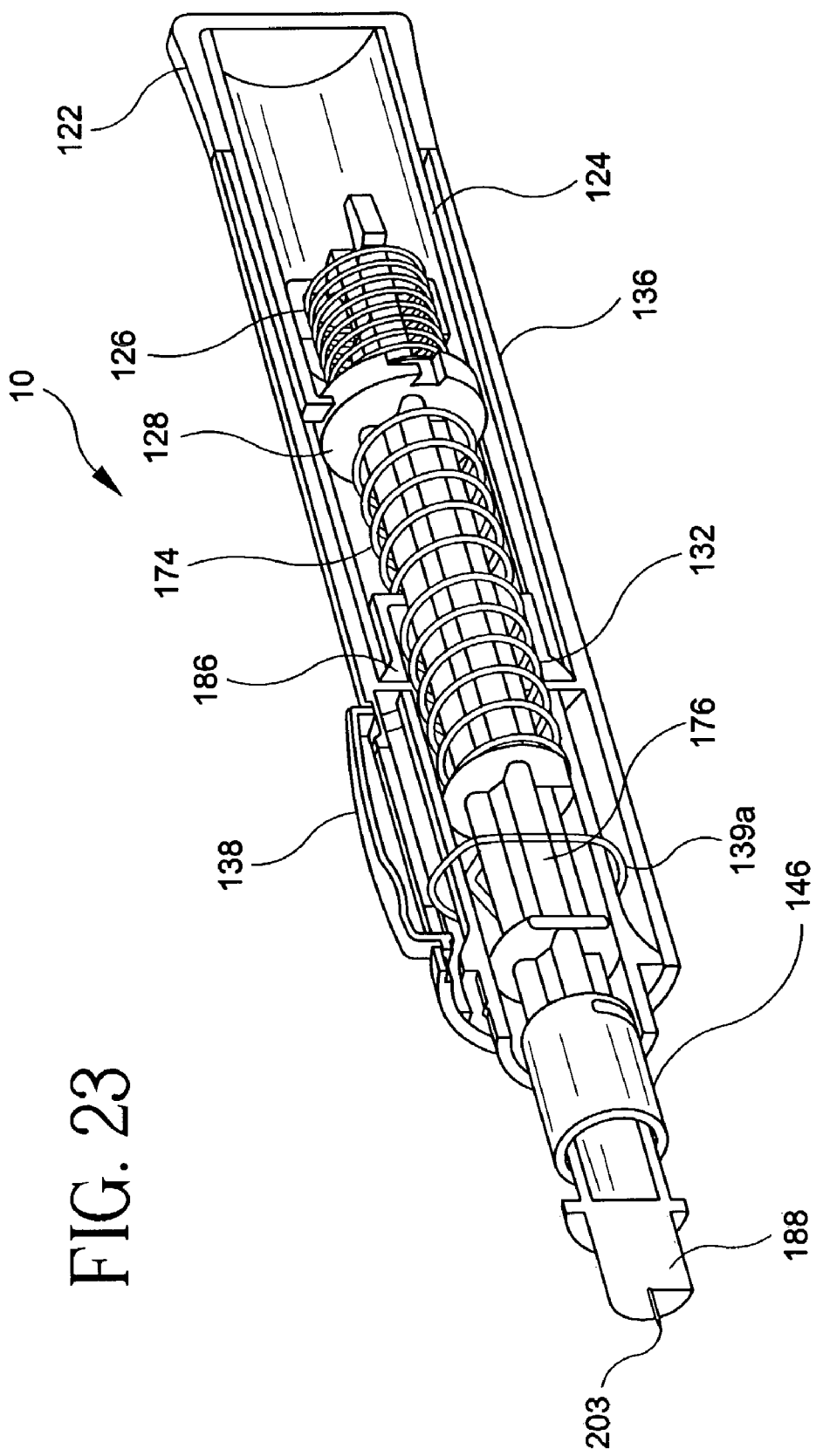
FIG. 23 shows a cut-away view of the lancer device having an ejection mechanism.
Figure 24:
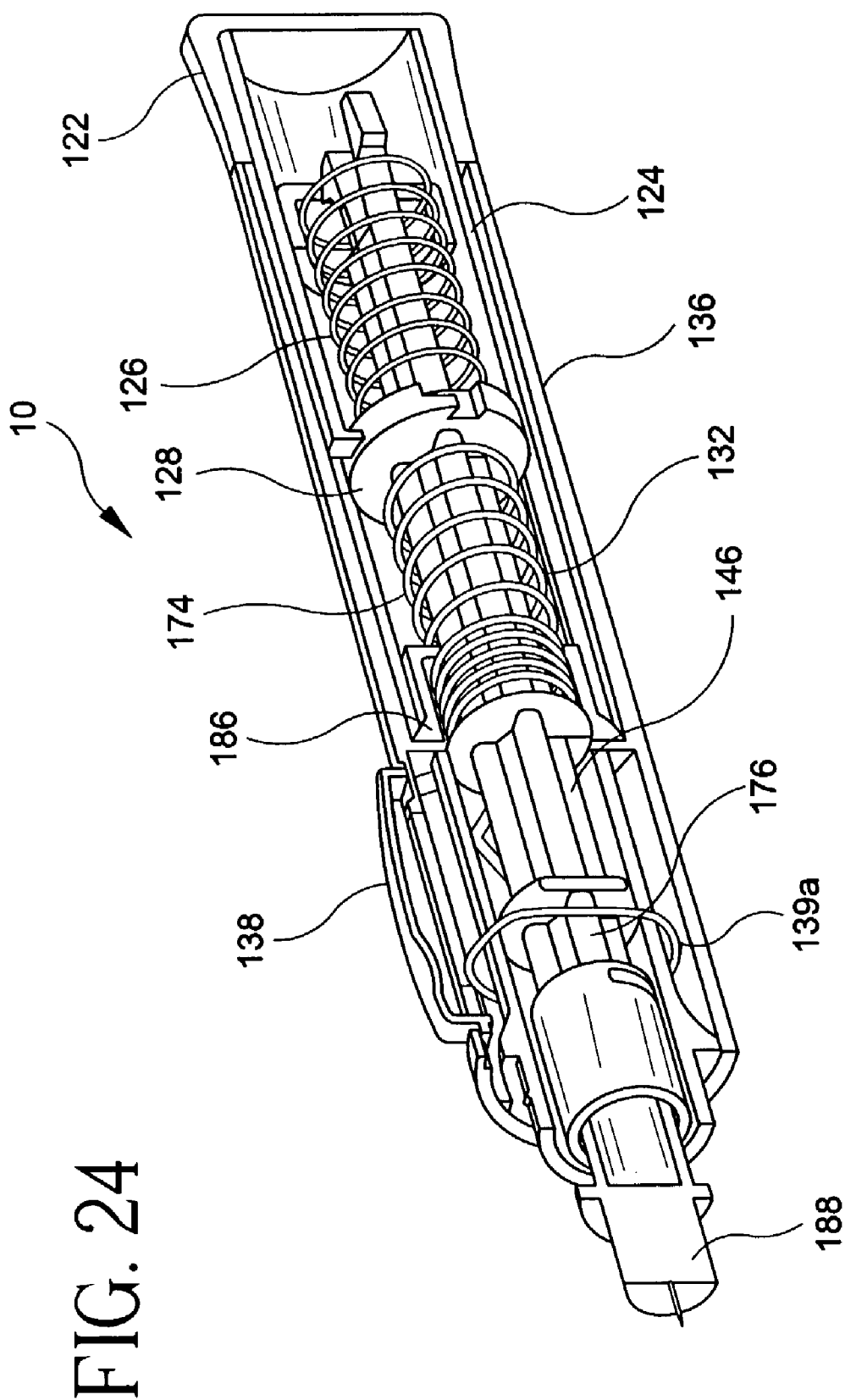
FIG. 24 shows a cut-away view of the lancer device having an ejection mechanism, in the armed position.

FIGS. 23 and 24 show a cut-away view of the lancer device 10, with ejecting mechanism. The embodiment shown in FIGS. 23 and 24 shows a wire latch 139(*a*) that serves the function of the yoke latch described previously. The wire latch 139(*a*) is suitably an annular oval-shaped ring, which is used to retain the plunger, 146. When the tang 176 of the plunger 146 passes to the proximal side of wire latch 139(*a*), (for example, during retraction of the plunger 146) the wire latch 139(*a*) interfaces with the tang 176 to maintain the plunger 146 in an armed position. A force sufficient to displace the wire latch 139(*a*) permits the tang 176 to pass through the wire latch 139(*a*) and the plunger 146 to be propelled in the distal direction.

The device 10 can be discussed in terms of various states of operation. These include: pre-armed, cocked, armed, activated, and ejecting.

In the pre-armed, or natural, state the triggering spring 132, ejection spring 174, and return spring 126 are substantially non-compressed.

In the cocked state, the triggering spring 132 and the return spring 126 are substantially compressed; but the ejection spring 174 is substantially non-compressed. The end knob 122 is extended proximally.

In the armed state, the triggering spring 132 is substantially compressed, the return spring 126 and ejection spring 174 are substantially non-compressed. The end knob 122 is abutting the body assembly 136.

In the activated state, the return spring 124 is substantially compressed; but the neither the triggering spring 132 nor the ejection spring 174 is compressed.

In the ejection state, the triggering spring 132, return spring 124, and ejection spring 174 are substantially compressed. The end knob 122 is retracted to a second position, which is proximal to the extended position of the cocked state. This second position is achieved because the nose cap has been detached; enabling further retraction of the end knob 122 than when the nose cap is attached to the body section 136.

As shown in FIG. 23, the device 10 is in the activated state. Triggering spring 132 and ejection spring 174 are not fully compressed. As shown in FIG. 24, the device is in the armed state, in which triggering spring 132 is compressed and ejection spring 174 is slightly compressed providing a bias in the distal direction. The return spring 126 is not compressed. Elements discussed previously are not discussed in relation to FIGS. 23 and 24.

Figure 25:
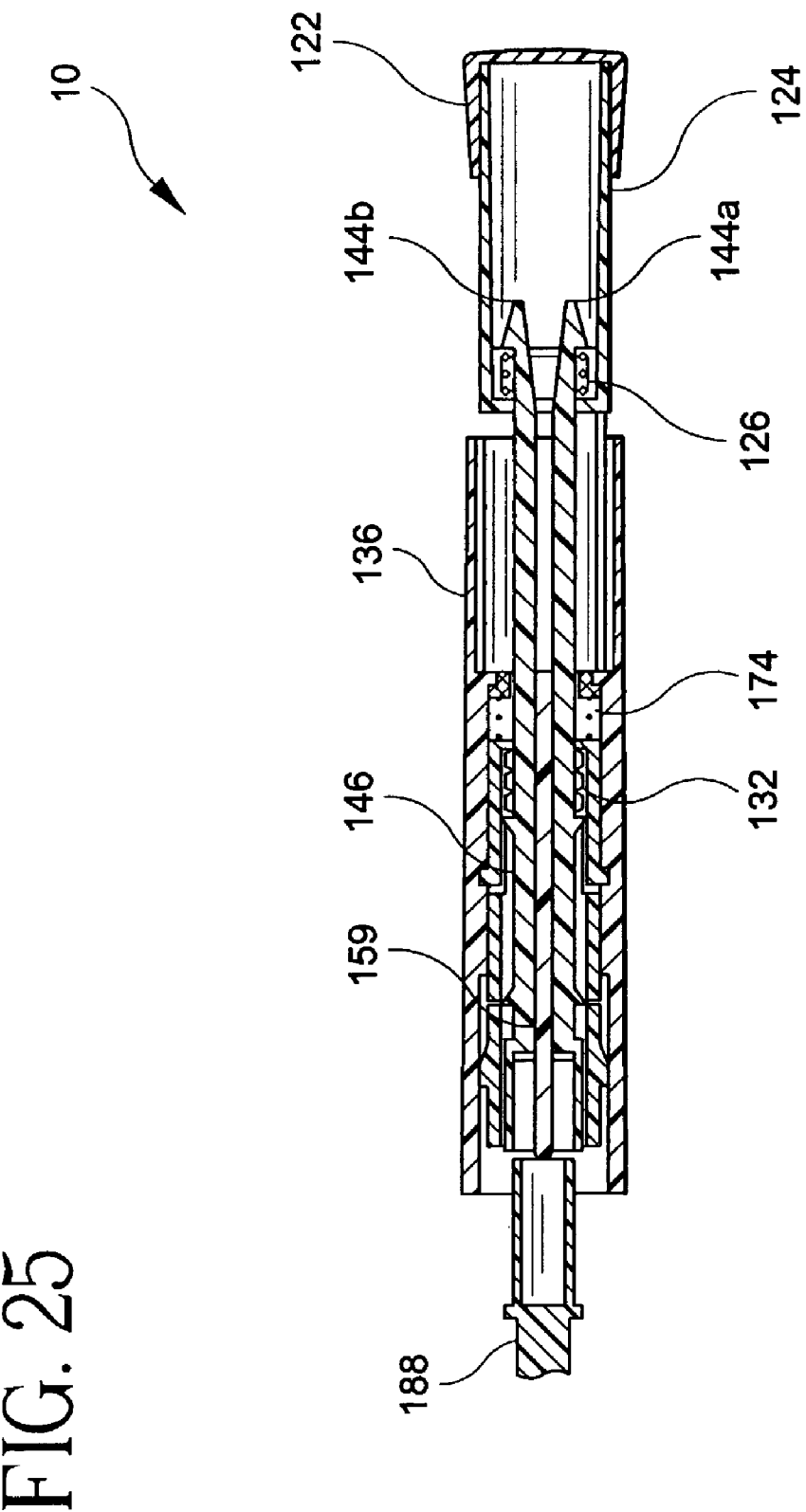
FIG. 25 shows a cross-sectional view of the lancer with the ejection mechanism.

FIG. 25 shows a cross-sectional view of lancer device 10, in the ejection state, ejecting a lancet 188. Triggering spring 132, return spring 126 and ejection spring 174 are compressed. Blade 159 prevents lancet 188 from retracting as plunger 146 is retracted by applying a force in the proximal direction via knob cap 122, which retracts inner knob 124.

Detents 144(*a*) and 144(*b*) and body assembly 136 have been discussed previously.

Figure 26:
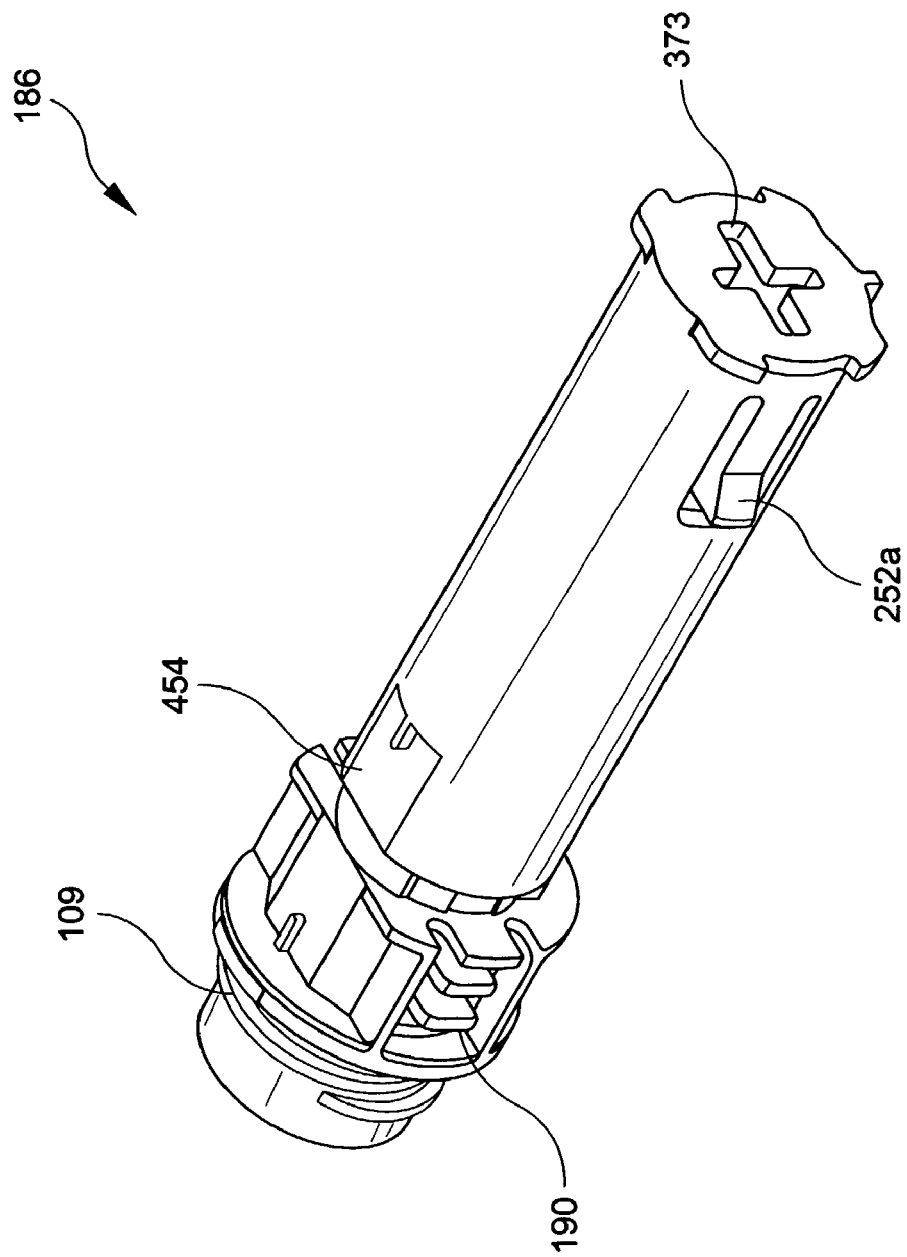
FIG. 26 shows a perspective view of a sleeve member.

FIG. 26 shows a perspective view of sleeve 186. As shown in FIG. 26, sleeve 186 has threaded portion 109, for connection to tip thread member (not shown). Portion 252(*a*) is a member that suitably extends radially outward from the sleeve 186 and is used to hold sleeve 186 in a controlled position within the body assembly. (When the sleeve 186 is used in conjunction with the ejection mechanism, described herein, the sleeve has controlled axial motion. When the sleeve is used without the ejection mechanism, it is in a fixed position.) In FIG. 26, proximal portion of sleeve 186 has an orifice 373 similar to the orifice in the retaining plug 128 and thus, the plunger can move axially within sleeve 186. The dimensions of the orifice 373 are sized to result in minimal radial movement of the plunger within the sleeve 186. This facilitates control and improves the trajectory path of the plunger, thereby reducing undesired radial motion. Detents 190 enable secure positioning of sleeve 186 in the body portion. Slotted area 454 provides access of the latch to tangs of the plunger since the plunger is disposed within the sleeve 186.

Figure 27:
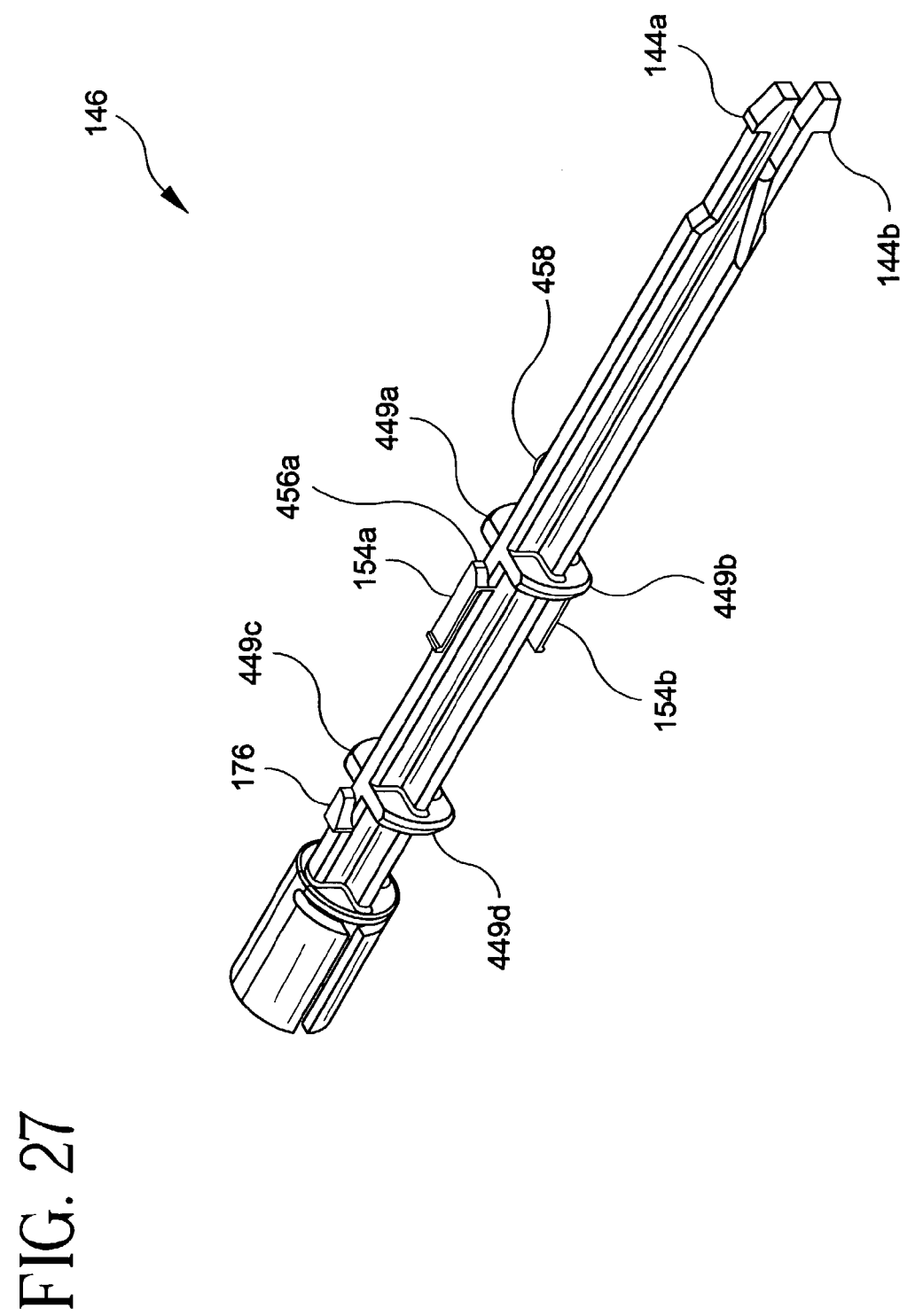
FIG. 27 shows a perspective view of a plunger having a vibration-dampening mechanism.
Figure 28:
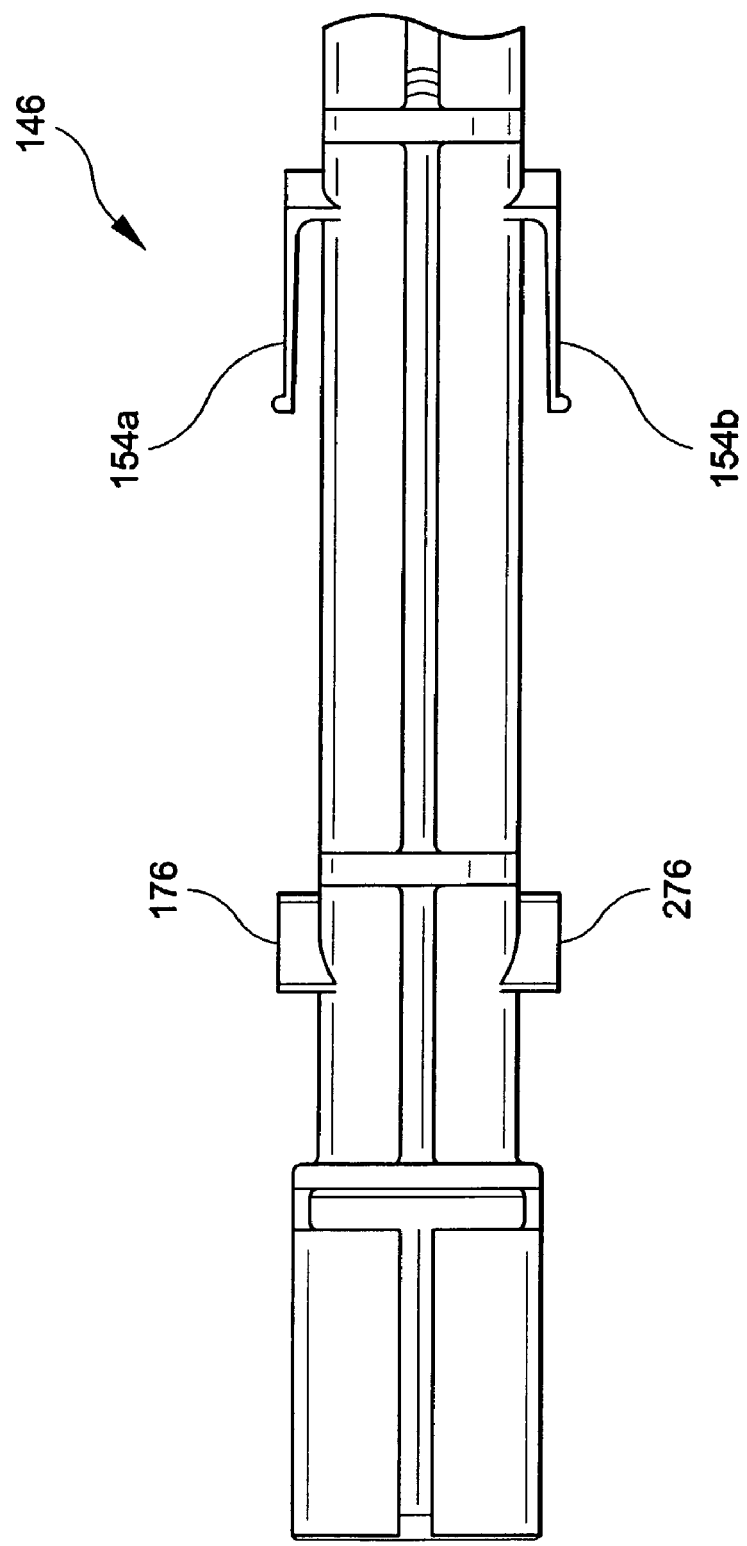
FIG. 28 shows vibration-dampening members.

FIGS. 27 and 28 show the vibration dampening mechanism of the device. FIG. 27 shows a perspective view of plunger 146 with wisps 154(*a*) and (*b*). Wisps 154(*a*) and (*b*) (typically there are any number of wisps but only two are described herein) are suitably cantilevered protrusions extending from plunger member 146. Alternatively, the wisps 154 may be mounted directly on proximal tangs, which are similar to tang 176 except that they are located proximal to the tang 176 on plunger 146. The proximal tangs are illustrated as tang 456(*a*).

The vibration dampening mechanism provides stabilization during arming of the device, actuation of the device and when the lancet is retracting, after being fired.

Also, disk surfaces 449(*a*) . . . (*d*) are disposed on plunger 146. These surfaces provide a centering feature for the plunger 146. Alternatively, these surfaces could be a peg-like protrusion to interface with a corresponding rail or channel in either the inner diameter of the body assembly or the sleeve.

A protrusion 458 is formed proximal to surfaces 449(*a*) and 449(*b*), and is suitably a raised member for limiting the travel of the plunger 146 in the proximal direction. The raised member 458 acts as a positive stop when the plunger 146 is being retracted in the proximal direction because it interfaces with the sleeve or body to prevent further retraction of the plunger 146. When the device is in the ejection state, the raised member 458 facilitates movement of the sleeve proximally.

FIG. 28 shows a detailed view of wisps 154(*a*) and 154(*b*). The wisps 154(*a*) and 154(*b*) are suitably fabricated from the same material as the plunger 146 and are mounted so as to have the capability to expand slightly and thereby interact with the inner diameter of a structure in which the plunger 146 is disposed i.e., sleeve or body assembly. This interaction decreases the vibration of the plunger 146 when actuated and when retracting. Tangs 176 and 276 are also illustrated.

Figure 29:
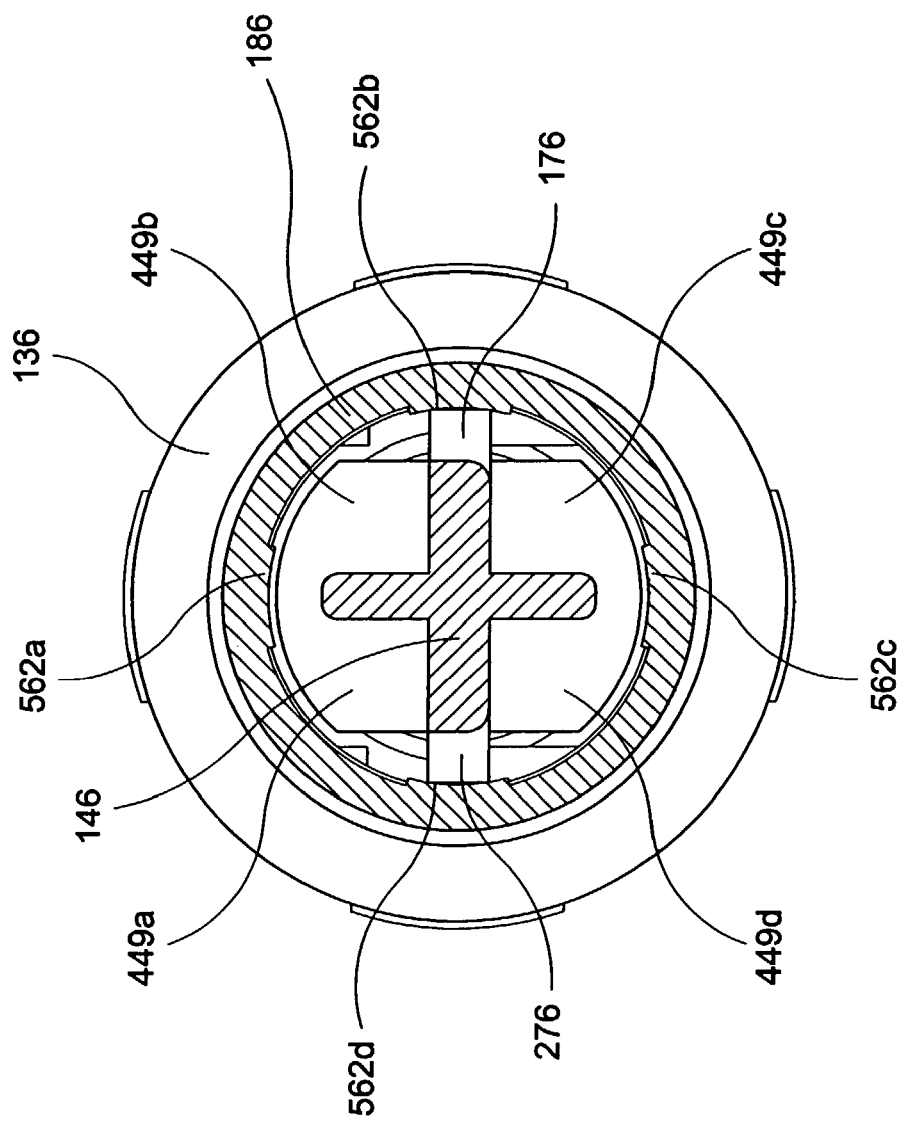
FIG. 29 shows a mechanism for reducing radial movement of the lancet.

FIG. 29 shows a centering feature of the instant invention. Although FIG. 29 shows a cross-sectional view of the body assembly 136 with sleeve member 186, this feature is suitably used with or without a sleeve member 186. The inner diameter has one or more surfaces 562(*a*) . . . (*d*) that are designed to interact with a portion of plunger member 146. Although FIG. 29 shows four raised surfaces 562(*a*) . . . (*d*), there could be any number that comports with the design of the structure.

The surfaces 562(*a*) . . . (*d*) provide specific contact points between the plunger 146 and an inner diameter of the sleeve 186 or body 136. These surfaces 562(*a*) . . . (*d*) are suitably one or more channels, one or more pegs, or one or more rails.

The plunger 146 member suitably has one or more protrusions 449(*a*) . . . (*d*); such as disks, wisps, cantilevered beams, or pegs that interact with the inner diameter surfaces 562(*a*) . . . (*d*) of the body assembly or sleeve member. This interaction serves to center the plunger 146 as it is propelled. The plunger 146 typically has an outer diameter of approximately 0.333 inch and the specific surface of body 136 or sleeve permits a minimal clearance, preferably less than 0.008 inch for the plunger within the body or sleeve. This provides for a substantially smooth fit between the plunger 146 and inner diameter of body assembly 136 or sleeve 186 permitting the plunger 146 to move primarily only axially within the body 136 or sleeve 186. Tangs 176 and 276 are also shown.

The lancer has been described above, a method of using the apparatus with all the mechanisms working in concert will now be described referring to the components identified in FIGS. 1-29.

The nose portion 104, with lancet stop 102, and collar 106 are detached from the sleeve 186 or body assembly 136. An unused lancet 188 is inserted into a receptacle 254 of plunger 146. The nose portion 104 and collar 106 are attached to body section 136. The collar 106 is turned to a desired setting for drawing sufficient blood. This setting is typically chosen from numbers 1-6. The device 10 is armed by pulling back on knob cap 122, which locks plunger 146 in a high potential energy state because return spring 126 and triggering spring 132 are substantially compressed. The knob cap 122 is then released and returned to its starting position and the return spring 126 is substantially non-compressed.

The pressure surface 168(*b*) is pressed against a desired area of the patient and the device is actuated by pressing button 138 with the necessary force to compress biasing means 142. Biasing means 142, once overcome, moves latch 139 so tangs 176, 276 pass through latch 139 in the distal direction. The lancet 188 carried by plunger 146 is accelerated into the lancet stop 102 by the force of the triggering spring 132. The stylet 203 emerges from nose orifice 184 with sufficient energy to pierce the skin of a patient and the lancet 188 is stopped by the lancet stop 102. Return spring 126 retracts stylet 203 into device 10 via lancet 188. After obtaining the desired quantity of blood, the nose portion 104 is detached from body section 136. The knob cap 122 is then retracted in the same fashion as arming to a first position. The return spring 126 is compressed. Further retraction compresses triggering spring 132 and yet further retraction compresses ejection spring 174, all the while applying a force to the plunger 146, causing plunger 146 to be retracted. At this point, ejection blade 159 contacts lancet 188 to prevent the lancet 188 from retracting with the plunger 146, causing release of the lancet 188 from the plunger 146.

Figure 30:
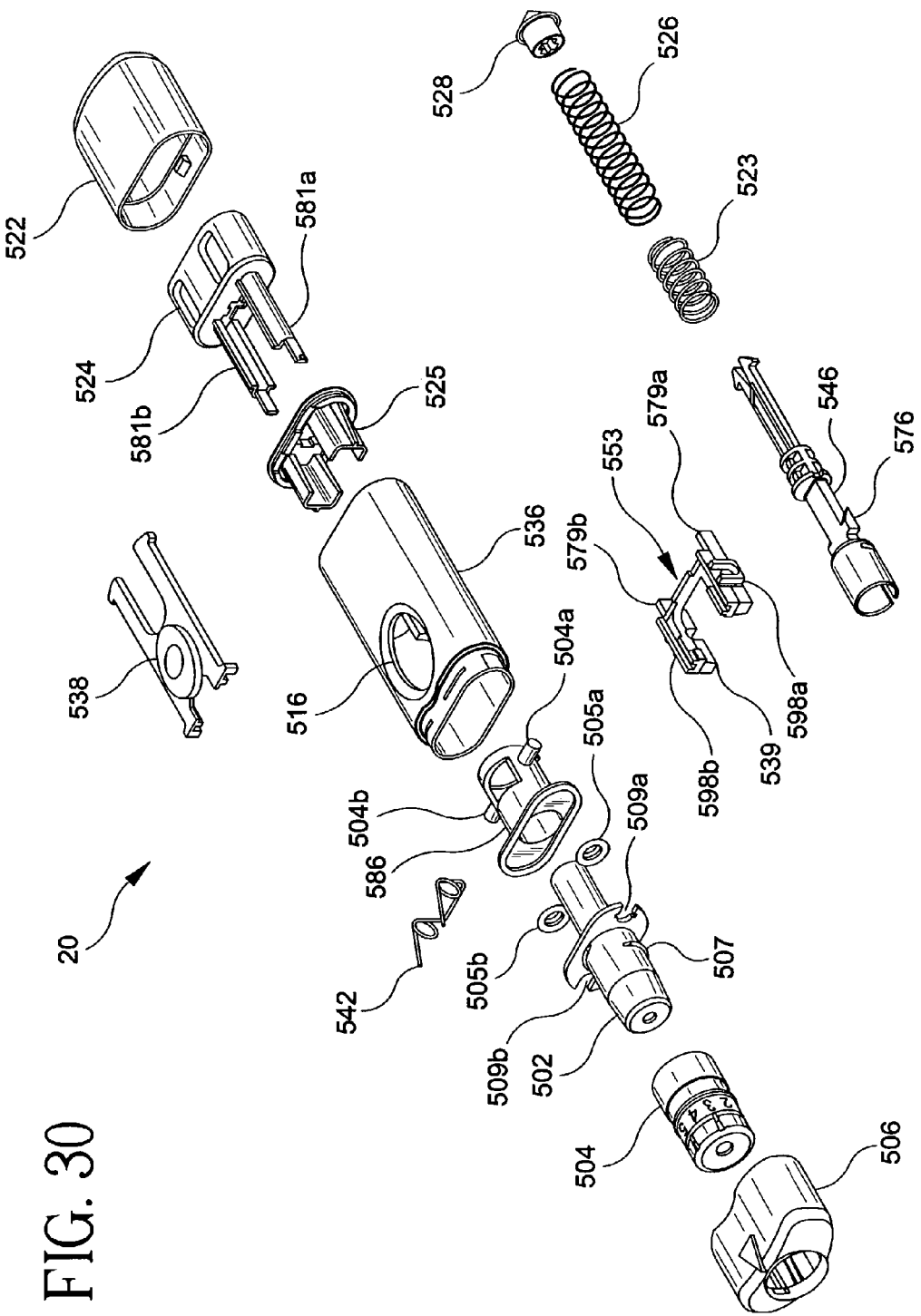
FIG. 30 shows an exploded view of an oblong lancer device.

FIGS. 30-33 show an alternate embodiment of the lancer device that has an oblong shape. FIG. 30 shows an exploded view of a lancer 20. Lancer 20 has an oblong outer body section 536 connected to an end knob 522. End knob 522 is used for arming or cocking the device 20 and is sized to be compatible with the oblong shaped body 536. Body section 536 suitably has an orifice 516 in which a release means, such as a trigger or button 538, is mounted. Disposed within body 536 is a plunger or shaft 546. A tip assembly 508 suitably includes an inner member 502, outer adjustment member 504, and nose portion 506. In this embodiment tip assembly 508 can be detached from the body assembly 536. Adjustment member 504 is constrained from linear motion in nose portion 506. Adjustment member 504 only moves radially. The inner member, also referred to as a lancet stop, 502 has a full thread-form, mating into the adjustment member 504. The user rotates radially the adjustment member 504 to change the relative distance between the adjustment member 504 and the lancet stop 502. The slots 509(a) and 509(b) interact with posts (posts shown as 593 (a) and 593(b) in FIG. 33) to prevent radial motion of stop 502 and permit the stop 502 to move only axially due to the camming motion of the thread forms. This has been discussed herein in relation to FIG. 6.

The oblong-shaped embodiment 20 uses posts to eliminate relative rotation between the stop 502 and nose portion 506.

When armed, the yoke latch 539 retains one or more tangs (shown as a single tang 576) of plunger 546 in yoke latch window 553. Yoke latch 539 is mounted to sleeve 586. Mounting points 598(a) and 598(b) on yoke latch 539, which are for example, apertures in yoke latch 539, attach to posts 504(a) and 504(b) of sleeve 586, respectively. These mounting points 598(a) and 598(b) form a pivot axis when yoke latch 539 is actuated. Actuation is achieved by overcoming biasing means 542 to release yoke latch 539. The yoke latch 539 is pivoted about the pivot axis against biasing means 542, which is suitably a spring. This causes the yoke latch 539 to move perpendicular to the axis of the device 20, enabling tang 576 on plunger 546 to pass through window 553 of yoke latch 539. After actuation, proximal fingers 579(a) and 579(b) (referred to as 579 herein) on the yoke latch 539 abut distal fingers 581(a) and 581(b) (referred to as 581 herein) of the inner knob 524, thereby preventing engagement of the yoke latch 539 on tang 576 of the plunger 546. The device can be armed by retracting end knob 522 in the proximal direction since this will cause the distal fingers 581 of inner knob 524 to disengage the yoke latch proximal fingers 579 and yoke latch 539 can engage tang 576 on plunger 546. This is accomplished by the yoke latch 539 pivoting about the pivot axis to a position in which the yoke latch 539 can engage the tang 576. Triggering spring 523 and return spring 526 perform triggering and return functions, respectively, as discussed herein. Retainer 528 facilitates retraction of the plunger 546. Members 505(a) and 505(b) provide support for the posts. Member 525 provides alignment for fingers 581(a) and 581(b).

Figure 31B:
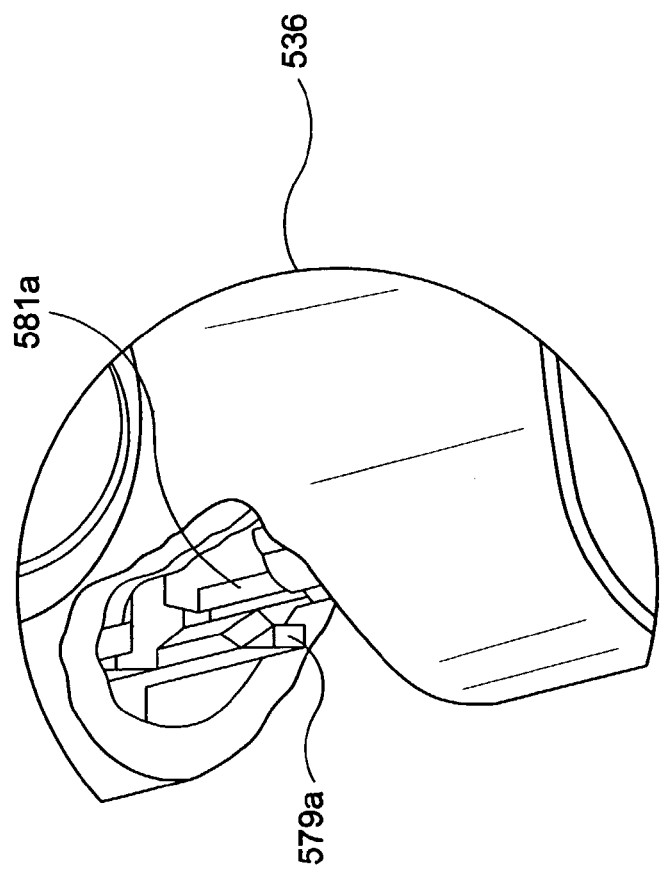
FIGS. 31A and 31B show the oblong lancer device.
Figure 31A:
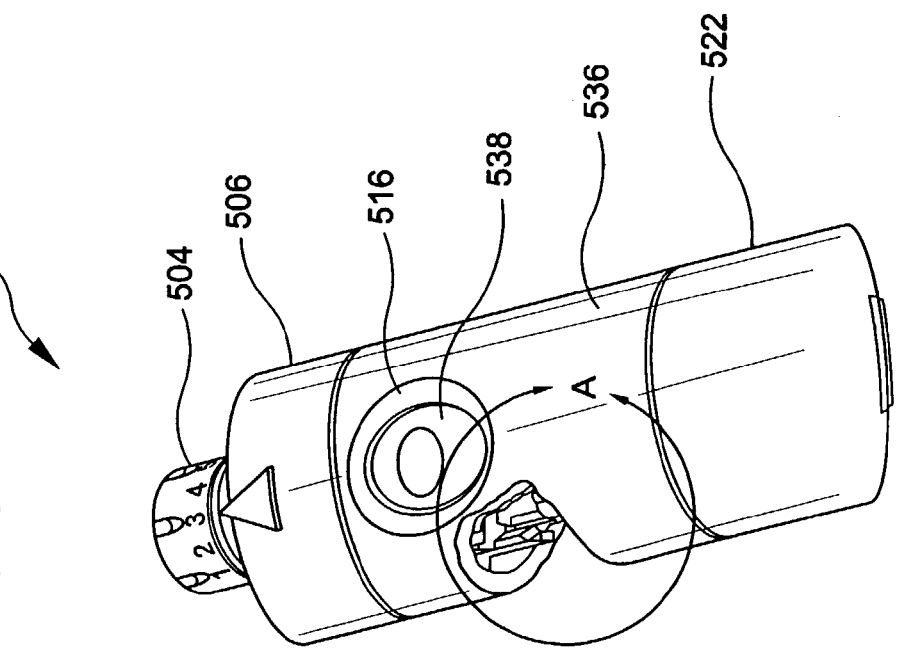

FIGS. 31A and 31B show the device 20 after firing. (FIG. 31B is a partial cut-away view of the device 20.) Proximal finger 579(a) on yoke latch abut distal finger 581(a) of inner knob. This interface prevents the plunger from being retracted into a loaded position from pressure exerted at the distal portion of device 20. This reduces the possibility of inadvertent arming or loading of device 20 and aids in insertion and removal of a lancet. Body assembly 536, end knob 522, button orifice 516, button 538, adjustment member 504 and nose 506 have been discussed previously.

Figure 32:
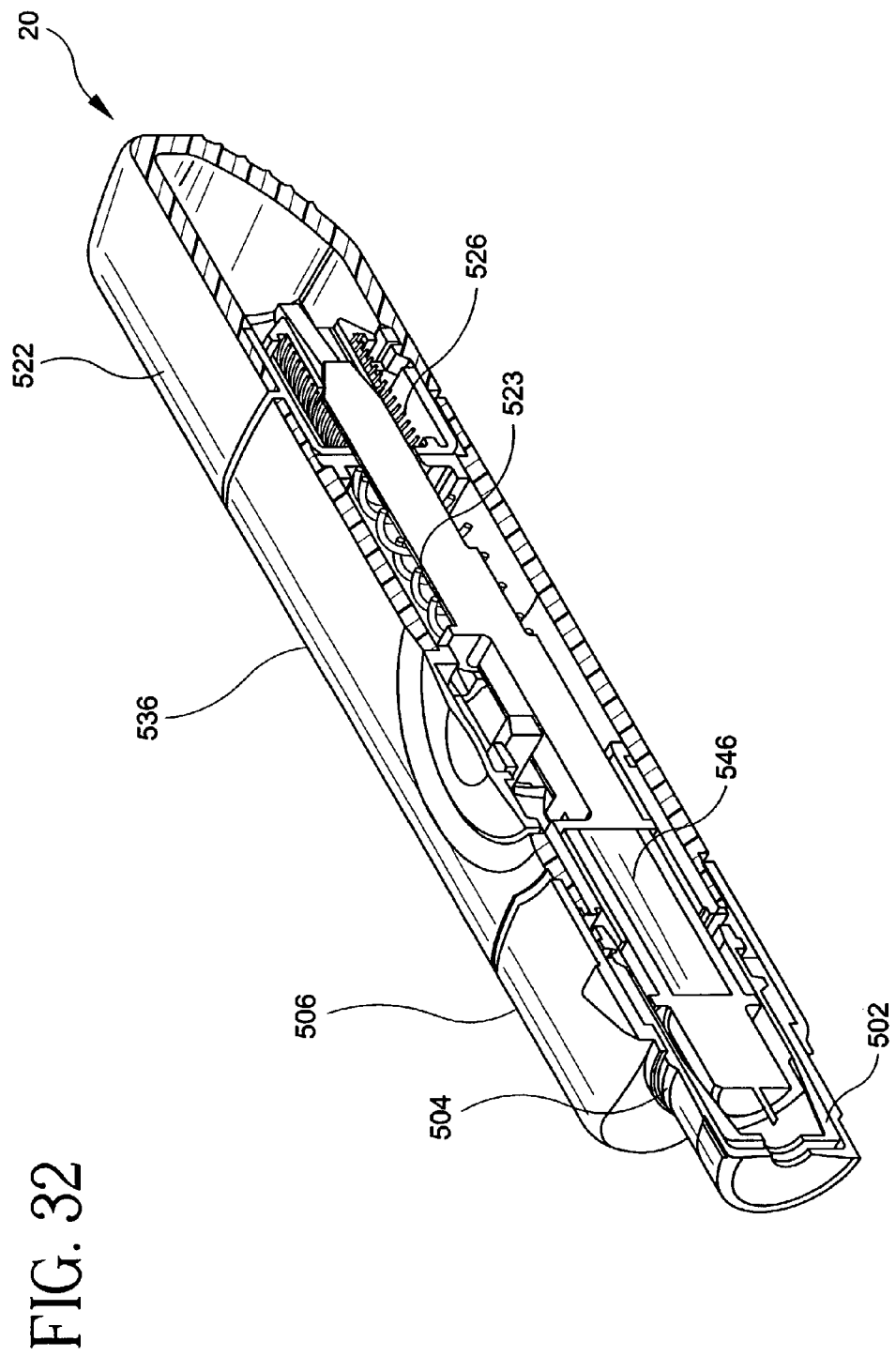
FIG. 32 shows an cut-away view of oblong lancer device.

FIG. 32 shows a cut-away view of the assembled device 20. The relationship of body assembly 536, lancet stop 502, adjustment member 504, nose portion 506 and end knob 522 is shown. The elements discussed previously are not discussed further here.

Figure 33:
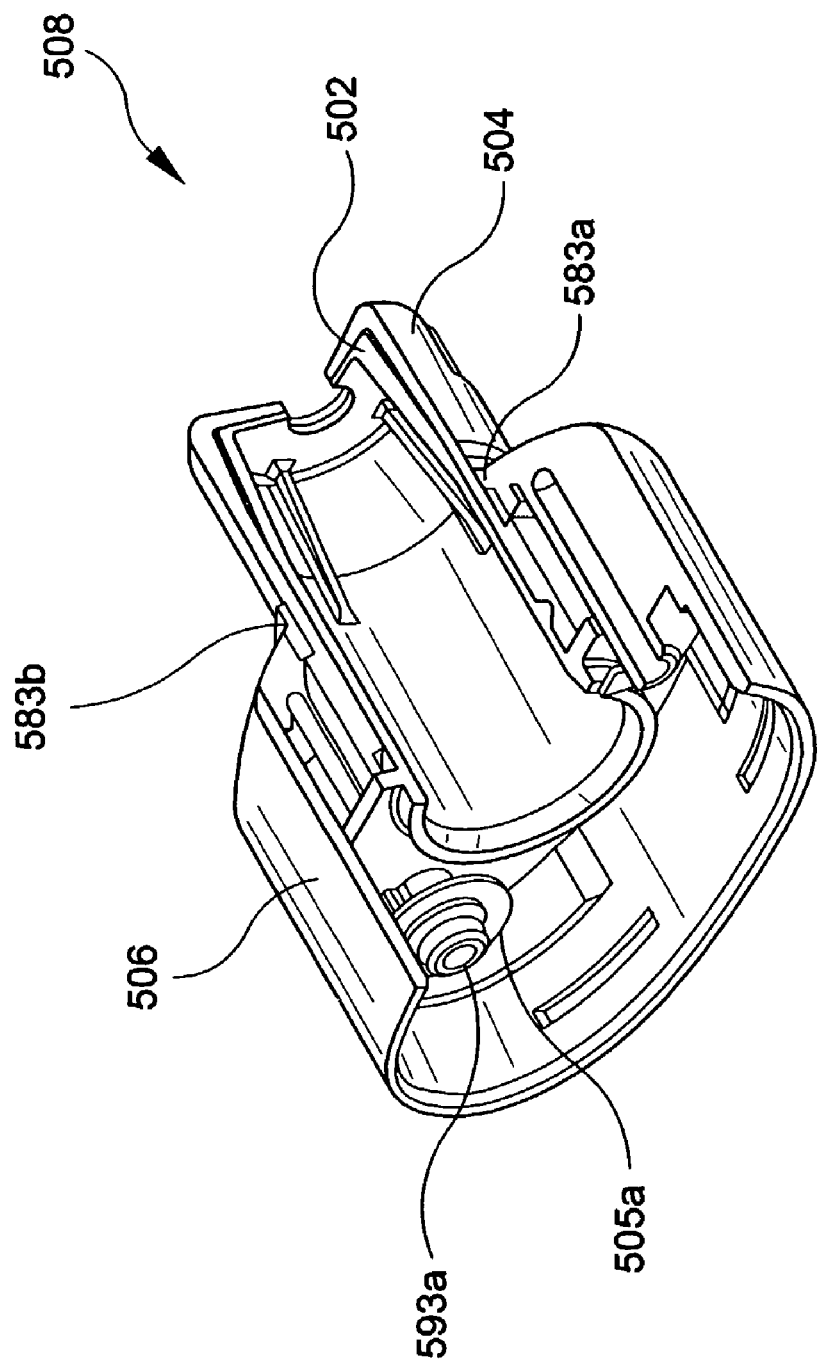
FIG. 33 shows a partial cut-away view of the adjustment portion of the oblong lancer device.

FIG. 33 shows an cut-away view of tip assembly 508 with post 593(a), which prevents rotation of lancet stop 502. Adjustment member 504 has detents 583(a) and 583(b) to prevent axial movement of adjustment member 504. Support member 505(a) is also shown.

Figure 34:
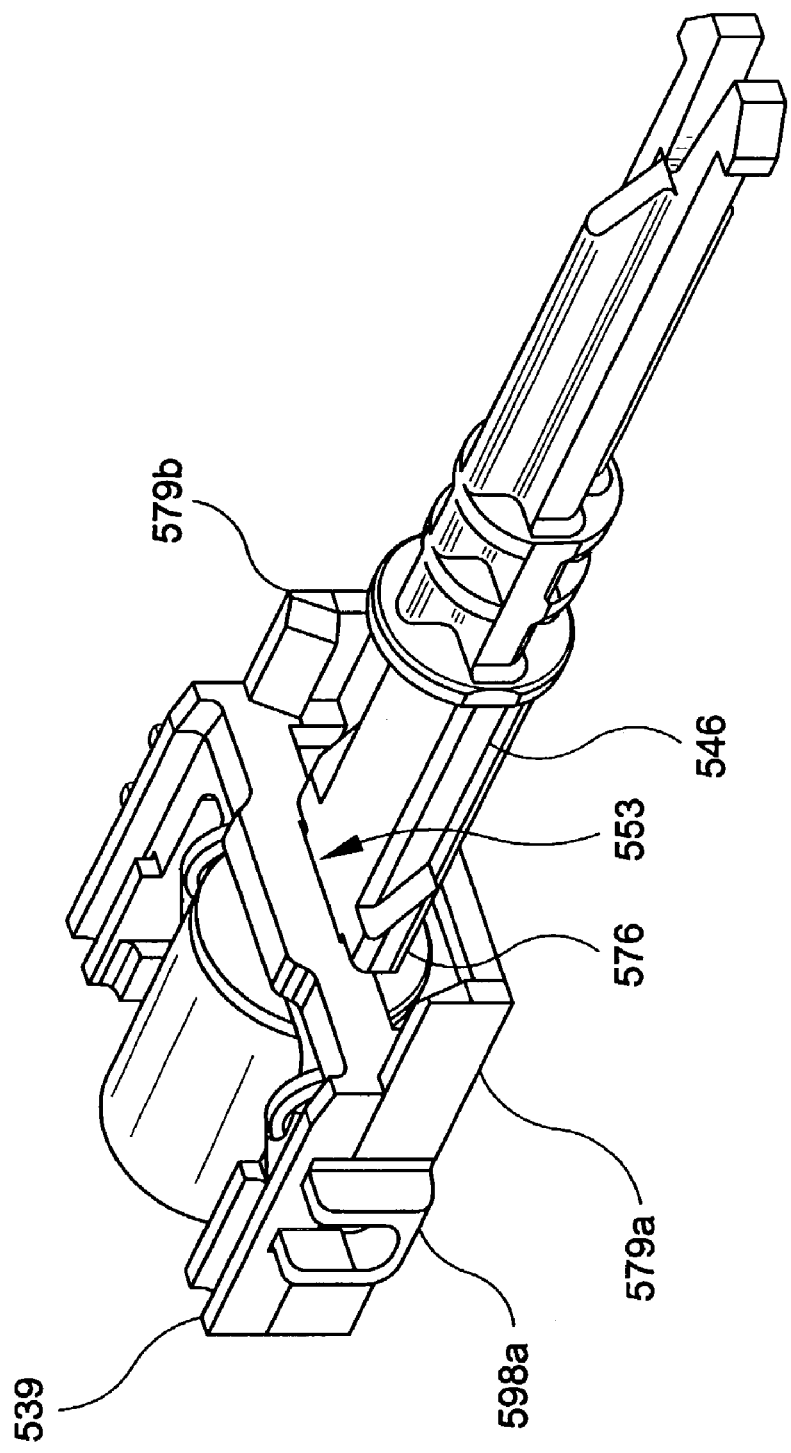
FIG. 34 shows the plunger and latch of the oblong lancer device.

FIG. 34 shows the latch 539 and plunger 546 as used in the device described as device 20 above. The latch 539 has mounting point 598(a), which enables the latch to move perpendicular to the axis of motion of the plunger 546. When latch 539 is actuated, plunger tang 576 passes through window 553, enabling the plunger 546 to move distally. Fingers 579(a) and 579(b) are used to abut proximal fingers (not shown) and thereby prevent retraction of the plunger 546 when the latch 539 has been actuated. When the plunger is retracted from the proximal end (i.e., end knob, shown as element 522 previously), the distal fingers 579(a) and 579(b) disengage the proximal fingers. This is a safety feature that will help prevent inadvertent loading of a lancet in the device.

FIGS. 35A-35C show a stylet 203 having an outer diameter of 31 gauge or smaller (i.e., higher gauge number). As the blood volume requirements for meters become smaller and smaller, less blood is required from the extraction site. Smaller gauge stylets will achieve smaller volumes because of the smaller diameter. The smaller diameter should require reduced penetration force and reduced patient trauma, which results in increased patient comfort. The stylet with a gauge of 31 or higher (i.e., smaller outer diameter) specifically targets a blood volume of 2.5 micro-liters for testing.

A 31 gauge stylet 203 is suitably fabricated from stainless steel and has an outer diameter of approximately $1 \times 10^{-2}$ inch, $+/-4 \times 10^{-4}$ inch. The primary angle, shown as angle 209 in FIG. 35A, is suitably between approximately 7 and 11 degrees, and preferably about 9 degrees. The primary angle 209 forms a surface 210. The secondary angle, shown as 211 is suitably between approximately 14 and 18 degrees, and preferably about 16 degrees, and forms surface 212. The secondary angle is a compound angle formed by rotating the stylet about the axis of the device by the amount of the primary angle. For example, in this embodiment, the stylet 203 was rotated 9 degrees, and a 16 degree angle was used as the secondary angle to form the surface 212.

A 32 gauge stylet (with similar geometry as described in relation to the 31 gauge stylet) has an outer diameter of approximately $9 \times 10^{-3}$ inch, $+/-4 \times 10^{-4}$ inch.

A 33 gauge stylet has an outer diameter of approximately $8 \times 10^{-3}$ inch, $+/-4 \times 10^{-4}$ inch.

The 32 and 33 gauge stylets are suitably fabricated with similar primary and secondary angles as those described in relation to the 31 gauge stylet.

Figure 36:
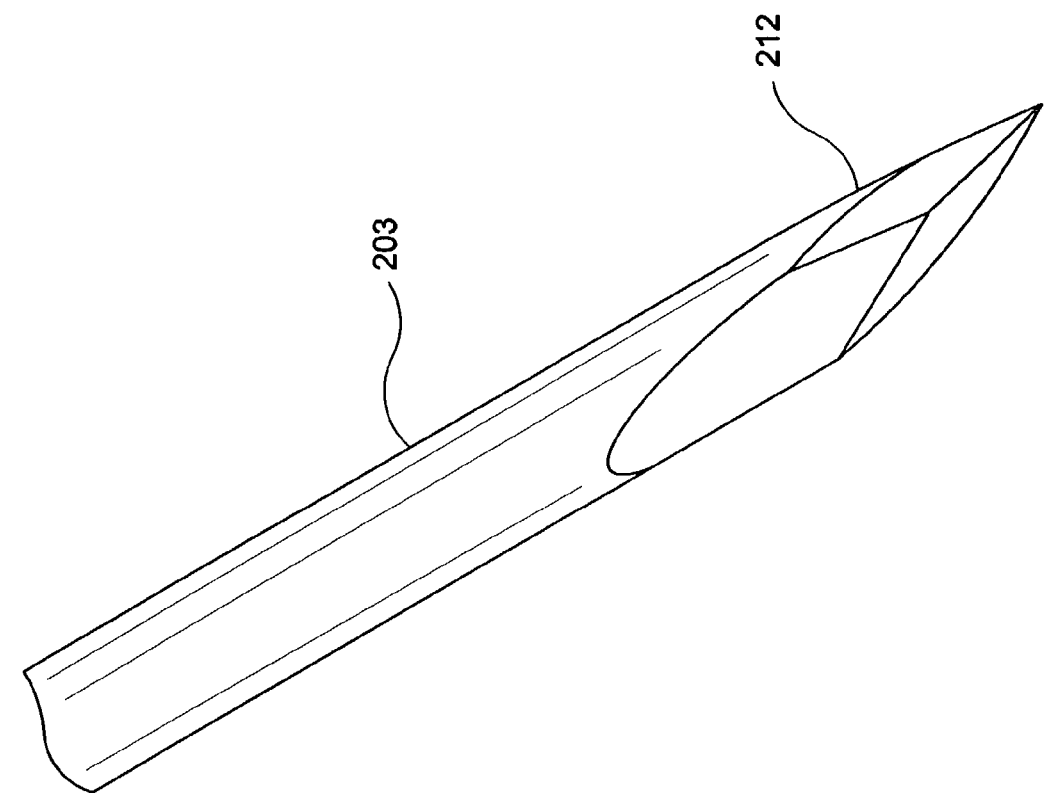

FIG. 36 shows the geometry of a 31 gauge stylet 203 with sharpened surface 212. This geometry also applies to lancets having a smaller gauge. The geometries of these stylets require lower penetration forces.

Figure 37:
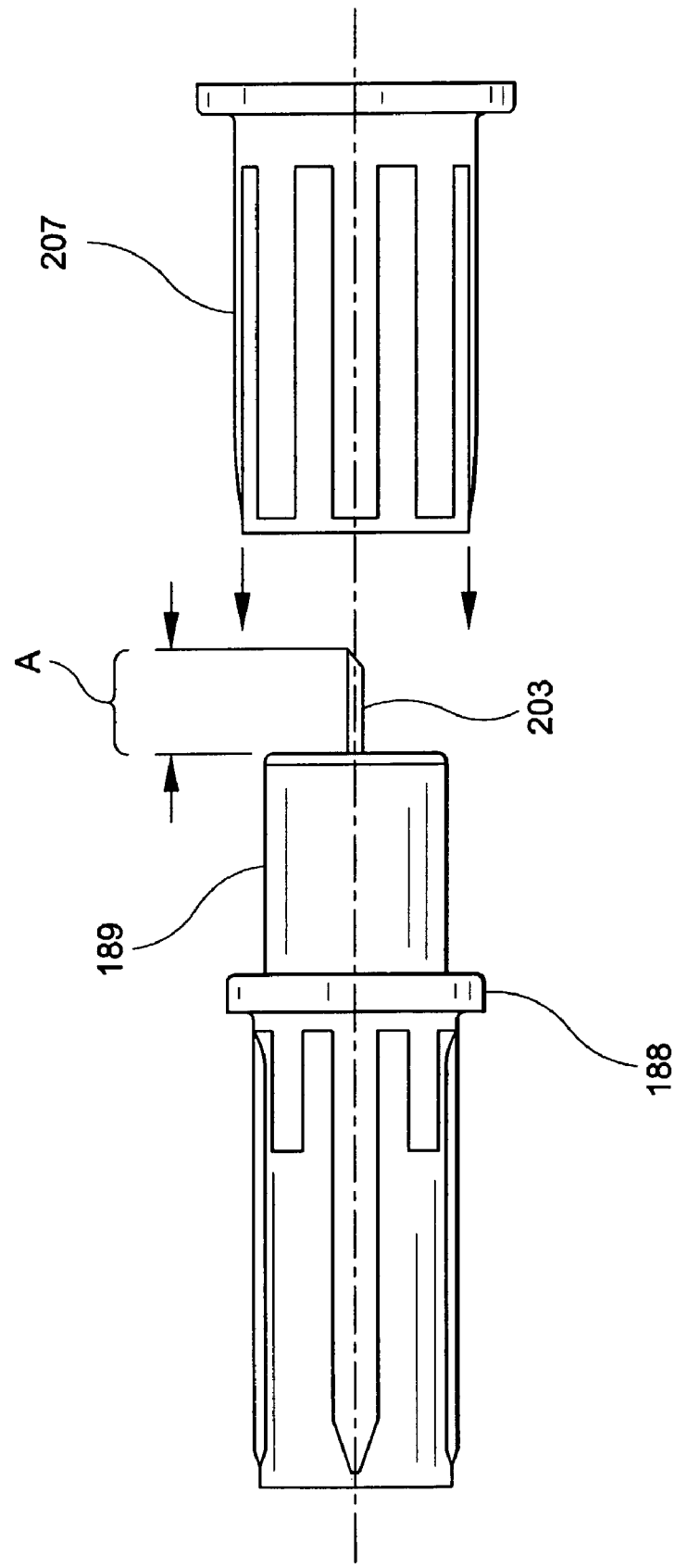
FIG. 37 shows a perspective view of the stylet with a shield.

FIG. 37 shows a stylet 203, with an outer diameter of 31 gauge or smaller, mounted to a lancet 188. A shield member 207 is suitably used to cover the stylet 203 by interfacing with portion 189 of lancet 188. The length of stylet 203 is typically between approximately 0.115 inch and 0.163 inch.

The stylet 203 also suitably has a rotation angle between approximately 17 degrees and 35 degrees the stylet 203 is also suitably lubricated to improve blood flow from a puncture wound made by the stylet other variations and modifications of this invention will be obvious to those skilled in this art. This invention is not to be limited except as set forth in the following claims.

What is claimed is:

1. A lancer system comprising a lancer body assembly and an adjustment assembly, the adjustment assembly attachable to the lancer body assembly and comprising:
    an outer member, having a distal portion and a proximal portion, the distal portion having an exterior surface, an interior surface and an orifice, a portion of the outer member being rotatable with respect to the lancer body assembly; and
    an inner member, having a distal portion and a proximal portion, the distal portion having an interior surface, an exterior surface and an orifice;
    wherein the inner member is fully contained within the outer member and positioned relative to the outer member such that when the outer member is rotated, the inner member moves relative to the body assembly, thereby adjusting the distance between the orifice of the inner member and the orifice of the outer member; and
    wherein the outer member is prevented from axial motion relative to the body assembly.

2. The lancer system according to claim 1, wherein the inner member further comprises at least one protrusion, disposed on the exterior surface, for engaging a portion of the adjustment member to maintain an axial position of the inner member.

3. The lancer system according to claim 1, wherein the outer member has one or more slots in the interior surface, and the inner member has one or more protrusions, interacting with the one or more slots of the outer member, for restricting rotation of the inner member and providing linear movement of the inner member.

4. The lancer system according to claim 1, wherein the adjustment assembly further comprises markings for indicating the relative positions of inner member and outer member.

5. The lancer system according to claim 1, further comprising an aperture for exposing a depth setting.

6. The lancer system according to claim 5, further comprising a covering mounted on the aperture.

7. A lancer system comprising a lancer body assembly, a lancet having a stylet, and an adjustment assembly, the adjustment assembly attachable to the lancer body assembly and comprising:
    an outer member, having a distal portion and a proximal portion, the distal portion having an exterior surface, an interior surface and an orifice, a portion of the outer member being rotatable with respect to the lancer body assembly; and
    an inner member, having a distal portion and a proximal portion, the distal portion having an interior surface, an exterior surface and an orifice;
    wherein the inner member is positioned relative to the outer member such that the lancet stylet protrudes from the orifice of the inner member and from the orifice of the outer member, and such that, when the outer member is rotated, the inner member moves relative to the body assembly, thereby adjusting the distance between the orifice of the inner member and the orifice of the outer member, to adjust the penetration depth of the lancet stylet; and
    wherein the outer member is prevented from axial motion relative to the body assembly.

\* \* \* \* \*